(12) United States Patent
Hagmann et al.

(10) Patent No.: US 6,420,418 B1
(45) Date of Patent: Jul. 16, 2002

(54) HETEROCYCLE AMIDES AS CELL ADHESION INHIBITORS

(75) Inventors: William K. Hagmann, Westfield; Stephen E. Delaszlo, Rumson; George Doherty, Princeton; Linda L. Chang, Wayne; Ginger X. Yang, Jersey City, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/638,074

(22) Filed: Aug. 14, 2000

Related U.S. Application Data

(60) Provisional application No. 60/149,042, filed on Aug. 16, 1999.

(51) Int. Cl.[7] .............................................. A61K 31/34
(52) U.S. Cl. ........................ 514/471; 514/470; 514/465; 549/322; 549/484
(58) Field of Search ................................. 514/471, 470, 514/465; 549/522, 484

(56) References Cited

U.S. PATENT DOCUMENTS

| | | |
|---|---|---|
| 5,334,730 A | 8/1994 | Langhals |
| 5,936,065 A | 8/1999 | Arrhenius et al. |
| 6,020,347 A | 2/2000 | Delaszlo et al. |
| 6,069,163 A | 5/2000 | Delaszlo |
| 6,096,773 A | 8/2000 | Scott et al. |

FOREIGN PATENT DOCUMENTS

| | | |
|---|---|---|
| WO | WO 98/53814 | 5/1998 |
| WO | WO 99/10312 | 3/1999 |
| WO | WO 99/36393 | 7/1999 |
| WO | WO 99/37618 | 7/1999 |

*Primary Examiner*—Amelia Owens
(74) *Attorney, Agent, or Firm*—Mollie M. Yang; David L. Rose

(57) ABSTRACT

Compounds of Formula I are antagonists of VLA-4 and/or α4β7, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, retinitis, rheumatoid arthritis, septic arthritis, stroke, tumor metastasis, uveititis, and type I diabetes.

22 Claims, No Drawings

HETEROCYCLE AMIDES AS CELL ADHESION INHIBITORS

CROSS REFERENCE TO RELATED APPLICATIONS

This application is based on, and claims priority from, U.S. Provisional Application No. 60/149,042, filed Aug. 16, 1999, which is hereby incorporated by reference in its entirety.

SUMMARY OF THE INVENTION

The compounds of the present invention are antagonists of the VLA-4 integrin ("very late antigen-4"; CD49d/CD29; or α4β1), the α4β7 integrin (LPAM-1 and α4βp), and/or the α9β1 integrin, thereby blocking the binding of VLA-4 to its various ligands, such as VCAM-1 and regions of fibronectin, α4β7 to its various ligands, such as MadCAM-1, VCAM-1 and fibronectin, and/or α9β1 to its various ligands, such as tenascin, osteopontin and VCAM-1. Thus, these antagonists are useful in inhibiting cell adhesion processes including cell activation, migration, proliferation and differentiation. These antagonists are useful in the treatment, prevention and suppression of diseases mediated by VLA4-, α4β7-, and/or α9β1-binding and cell adhesion and activation, such as AIDS-related dementia, allergic conjunctivitis, allergic rhinitis, Alzheimer's disease, aortic stenosis, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, myocarditis, organ transplantation, psoriasis, restenosis, retinitis, rheumatoid arthritis, septic arthritis, stroke, tumor metastasis, type I diabetes, vascular occlusion following angioplasty.

BACKGROUND OF THE INVENTION

The present invention relates to oxygen and sulfur heterocyclic amide derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selecting, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of a and b heterodimeric, transmembrane receptor molecules found in various combinations on nearly every mammalian cell type. (for reviews see: E. C. Butcher, *Cell*, 67, 1033 (1991); T. A. Springer, *Cell*, 76, 301 (1994); D. Cox et al., "The Pharmacology of the Integrins." *Medicinal Research Rev.* 14, 195 (1994) and V. W. Engleman et al., "Cell Adhesion Integrins as Pharmaceutical Targets." in *Ann. Repts. in Medicinal Chemistry*, Vol. 31, J. A. Bristol, Ed.; Acad. Press, NY, 1996, p. 191).

VLA-4 ("very late antigen-4"; CD49d/CD29; or α4β1) is an integrin expressed on all leukocytes, except platelets and mature neutrophils, including dendritic cells and macrophage-like cells and is a key mediator of the cell-cell and cell-matrix interactions of these cell types (see M. E. Hemler, "VLA Proteins in the Integrin Family: Structures, Functions, and Their Role on Leukocytes." *Ann. Rev. Immunol.* 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", *Immunol. Today*, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990. ) A role for VLA-4/CS-1 interactions in inflammatory conditions has been proposed (see M. J. Elices, "The integrin α4β1 (VLA-4) as a therapeutic target" in *Cell Adhesion and Human Disease*, Ciba Found. Symp., John Wiley & Sons, NY, 1995, p. 79).

α4β7(also referred to as LPAM-1 and α4βp) is an integrin expressed on leukocytes and is a key mediator of leukocyte trafficking and homing in the gastrointestinal tract (see C. M. Parker et al., *Proc. Natl. Acad. Sci. USA*, 89, 1924 (1992)). The ligands for α4β7 include mucosal addressing cell adhesion molecule-1 (MadCAM-1) and, upon activation of α4β7, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., *Nature*, 363, 461 (1993); A. Hamann et al., *J. Immunol.*, 152, 3282 (1994)). MadCAM-1 can be induced in vitro by proinflammatory stimuli (See E. E. Sikorski et al. *J. Immunol.*, 151, 5239 (1993)). MadCAM-1 is selectively expressed at sites of lymphocyte extravasation and specifically binds to the integrin, α4β7.

The α9β1 integrin is found on airway smooth muscle cells, non-intestinal epithelial cells (see Palmer et al.,*J. Cell Biol.*, 123, 1289 (1993)), and neutrophils, and,less so, on hepatocytes and basal keratinocytes (see Yokosaki et al., *J. Biol. Chem.*, 269,24144 (1994)). Neutrophils, in particular, are intimately involved in acute inflammatory responses. Attenuation of neutrophil involvement and/or activation would have the effect of lessening the inflammation. Thus, inhibition of α9β1 binding to its respective ligands would be expected to have a positive effect in the treatment of acute inflammatory conditions.

Neutralizing anti-α4 antibodies or blocking peptides that inhibit the interaction between VLA-4 and/or α4β7 and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against α4β1 integrin." *Nature*, 356, 63 (1993) and E. Keszthelyi et al., "Evidence for a prolonged role of α4 integrin throughout active experimental allergic encephalomyelitis." *Neurology*, 47, 1053 (1996)); ii) bronchial hyperresponsiveness in sheep and guinea pigs as models for the various phases of asthma (for example, see W. M. Abraham et al., "α4-Integrins mediate antigen-induced late bronchial responses and prolonged airway hyperresponsiveness in sheep." *J. Clin. Invest.* 93, 776 (1993) and A. A. Y. Milne and P. P. Piper, "Role of VLA-4 integrin in leucocyte recruitment and bronchial hyperresponsiveness in the guinea-pig." *Eur. J. Pharmacol.*, 282, 243 (1995)); iii) adjuvant-induced arthritis in rats as a model of inflammatory arthritis (see C. Barbadillo et al., "Anti-VLA-4 mAb prevents adjuvant arthritis in Lewis rats." *Arthr. Rheuma.* (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between α4-integrins and vascular cell adhesion molecule-l.", *J. Clin. Invest.*, 93, 1700 (1994), A. Jakubowski et al., "Vascular cell adhesion molecule-Ig fusion protein selectively targets activated α4-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Tranplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts." *J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-α4 integrin monoclonal antibody.", *J. Clin. Invest.*, 92, 372 (1993)); vii) contact hypersensitivity models as: a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin a-4 subunit inhibit the murine contact hypersensitivity response." *Eur. J. immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The α4β1/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan) against VLA-4 in clinical development for the treatment of "flares" associated with multiple sclerosis and a humanized monoclonal antibody (ACT-1®/LDP-02 LeukoSite) against α4β7 in clinical development for the treatment of inflammatory bowel disease. Several antagonists of VLA-4 and α4β7 have been described (D. Y. Jackson et al., "Potent α4β1 peptide antagonists as potential anti-inflammatory agents", *J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6, 2495 (1996); K. C. Lin et al., "Selective, tight-binding inhibitors of integrin α4β1 that inhibit allergic airway responses", *J. Med. Chem.*, 42, 920 (1999); U.S. Pat. No. 5,510,332, WO97/03094, WO97/02289, WO96/40781, WO96/22966, WO96/20216, WO96/01644, WO96/06108, WO95/15973). There are reports of nonpeptidyl inhibitors of the ligands for α4-integrins (WO99/36393, WO98/58902, WO96/31206); A. J. Soures et al., *Bioorg. Med. Chem. Lett.*, 8, 2297 (1998). There still remains a need for low molecular weight, specific inhibitors of VLA-4- and α4β7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

PCT Application No. WO99/10312 discloses compounds having activity as inhibitors of binding between VCAM-1 and cells expressing VLA-4, and having the formula:

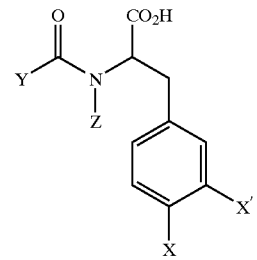

PCT Application No. WO99/36393 discloses inhibitors of α4-mediated cell adhesion having the formula:

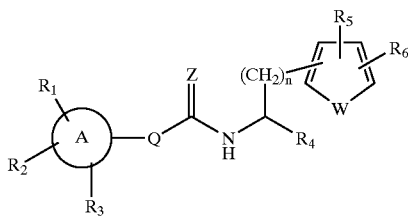

PCT Application No. WO99/37618 discloses inhibitors of α4 integrins having the formula:

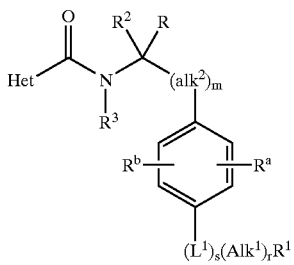

wherein Het is a heteroaromatic ring and R is carboxylic acid.

U.S. Pat. No. 5,334,730 discloses diasteromeric carboxylic acid amides of the formulae

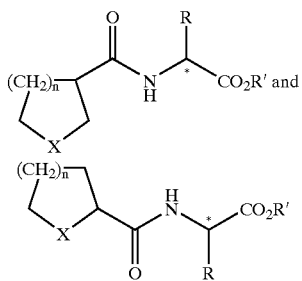

These compounds are useful for the separation of optically active isomers of the heterocyclic carboxylic acid. No biological or therapeutic activity is disclosed for these compounds.

DETAILED DESCRIPTION OF THE INVENTION

The present invention provides, in one aspect, a method for the prevention or treatment of diseases, disorders, conditions or symptoms mediated by cell adhesion in a mammal which comprises administering to said mammal an effective amount of a compound of Formula I:

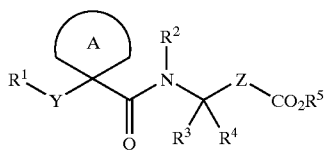

I or a pharmaceutically acceptable salt thereof wherein:

A is a 4- to 8-membered monocyclic saturated heterocyclic ling having one to two heteroatoms chosen from O, S and $S(O)_m$, optionally fused to an aryl group, wherein said heterocyclic ring and aryl group are optionally substituted with one to four substituents selected from a group independently selected from oxo, methylene and $R^b$;

Y is 1) a bond,
2) $C_{1-10}$alkylene,
3) $C_{2-10}$alkenylene,
4) $C_{2-10}$alkynylene,
  wherein said alkylene, alkenylene and alkynylene are each optionally substituted with one to four substituents selected from $R^a$, Z is 1) a bond, or
2) —$C(R^5)(R^6)$—

$R^1$ is 1) hydrogen,
2) Cy,
3) $OR^5$,
4) $OC(O)R^5$;
5) $OC(O)OR^5$,
6) $OC(O)NR^dR^e$,
7) $SR^5$,
8) $S(O)_mR^5$,
9) $SO_2NR^dR^e$,
10) $C(O)R^5$,
11) $C(O)OR^5$,
12) $C(O)NR^dR^e$,
13) $NR^dR^e$,
14) $NR^dC(O)R^5$,
15) $NR^dC(O)OR^5$,
16) $NR^dC(O)NR^dR^e$,
17) $NR^dSO_2R^5$;
  wherein Cy is optionally substituted with one to four substituents independently selected from $R^b$;

$R^2$ is
1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^3$ is
1) $C_{1-10}$alkyl,
2) $Ar^1$,
3) $C_{1-10}$alkyl-$Ar^1$,
4) $Ar^1$—$Ar^2$,
5) $C_{1-10}$alkyl-$Ar^1$—$Ar^2$,
  wherein the alkyl group is optionally substituted with one to four substituents selected from $R^a$, and $Ar^1$ and $Ar^2$ are optionally substituted with one to four substituents independently selected from $R^b$, $R^4$ is
1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^5$ is
1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
  wherein alkyl, alkenyl and alkynyl are optionally substituted with one to four substituents selected from $R^a$, and Cy is optionally substituted with one to four substituents independently selected from $R^b$;

$R^6$ is
1) hydrogen,
2) a group selected from $R^b$;

$R^a$ is
1) —$OR^d$,
2) $NR^dS(O)_mR^e$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N\text{-}OR^e)$,
22) $CF_3$,
23) —$OCF_3$,
24) $C_{3-8}$cycloalkyl, or
25) heterocyclyl;
  wherein cycloalkyl and heterocyclyl are optionally substituted with one to four groups independently selected from oxo and $R^c$;

$R^b$ is
1) a group selected from $R^a$,
2) $C_{1-10}$alkyl,
3) C2-10alkenyl,
4) C2-10alkynyl,
5) $Ar^1$,
6) $C_{1-10}$alky-$Ar^1$,
  wherein alkyl, alkenyl, alkynyl, and $Ar^1$ are optionally substituted with one to four substituents selected from a group independently selected from $R^a$;

$R^c$ is
1) halogen,
2) $NR^fR^g$,
3) $C(O)OR^f$,
4) $C_{1-4}$alkyl,
5) $C_{1-4}$alkoxy,
6) aryl,
7) aryl $C_{1-4}$alkyl,
8) hydroxy,
9) $CF_3$,
10) $OC(O)C_{1-4}$alkyl,
11) $OC(O)NR^fR^g$,
12) $NR^fC(O)R^g$,
13) $NR^fSO_2R^g$, or
14) aryloxy;
  $R^d$ and $R^e$ are independently selected from hydrogen, $C_{1-10}$alkyl,
$C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or
$R^d$ and $R^e$ together with the atom(s) to which they are attached form a heterocyclic ring of 4 to 7 members containing 0–2 additional heteroatoms independently selected from oxygen, sulfur and N—$R^h$;

$R^f$ and $R^g$ are independently selected from hydrogen, $C_{1-10}$alkyl, Cy and Cy—$C_{1-10}$alkyl; or
$R^f$ and $R^g$ together with the carbon to which they are attached form a ring of 5 to 7 members containing 0–2 heteroatoms independently selected from oxygen, sulfur and N—$R^h$;
$R^h$ is hydrogen, $C_{1-10}$alkyl, or $C(O)OC_{1-10}$alkyl;
Cy is selected from cycloalkyl, heterocyclyl and $Ar^1$;
$Ar^1$ and $Ar^2$ are independently selected from aryl and heteroaryl;
m is 1 or 2;
n is an integer from 1 to 10.

In one embodiment said disease or disorder is selected from asthma, allergic rhinitis, multiple sclerosis, atherosclerosis, and inflammatory bowel disease.

In another aspect the present invention provides a method for preventing the action of VLA-4 in a mammal which comprises administering to said mammal a therapeutically effective amount of a compound of formula I.

Another aspect of the present invention provides a pharmaceutical composition which comprises a compound of formula I and a pharmaceutically acceptable carrier.

Another aspect of the present invention provides novel compounds of formula I, with the proviso that when $R^1$—Y represents H, $R^4$ is H, and $R^3$ is (1) optionally substituted $C_{1-10}$ alkyl, (2) phenyl unsubstituted or substituted with methyl, hydroxy, or methoxy, or (3) benzyl unsubstituted or substituted with methyl, hydroxy, or benzyl, then $R^5$ is hydrogen, or a pharmaceutically acceptable salt thereof.

In one embodiment of compounds of formula I, A is 4- to 6-membered monocyclic saturated heterocyclic ring having one or two heteroatoms selected from O, S and $S(O)_m$, and optionally substituted with one to four groups independently selected from oxo and $R^b$. Examples of suitable saturated heterocyclic ring include oxetane, thietane, tetrahydrofuran, tetrahydrothiophene, tetrahydropyran, tetrahydrothiopyran, thioxane, dioxane. In another embodiment, A is aryl fused heterocyclic ring, and examples of which include dihydrobenzofuran, benzo-1,3-dioxolyl, and 1,2-dihydrothienyl. Examples of optional substituents for A include oxo, $C_{1-10}$alkyl, $C_{2-10}$alkenyl, $Ar^1$, $Ar^1$—$C_{1-10}$alkyl, $C_{1-10}$alkoxy, hydroxy, halogen, —$S(O)_2R^d$, —$S(O)_2NR^dR^e$, —$NR^dR^e$, —$O(CR^fR^g)_nNR^dR^e$, —$C(O)NR^dR^e$, wherein alkyl, alkenyl, alkoxy, $Ar^1$ are optionally substituted as provided under formula I. More particularly, suitable substituents for A include, but are not limited to, oxo, hydroxy, $NR^dR^e$ such as amino, pyrrolidinyl, piperidinyl and morpholinyl, aryl such as phenyl and methoxyphenyl, $C_{1-3}$alkyl-aryl such as benzyl, and $C_{-5}$alkyl optionally substituted with a group selected from $OC(O)NR^dR^e$, NHC(O) $R^e$, $NHSO2R^e$, and $OR^d$ such as methyl, carbamoyloxymethyl such as 1-pyrrolidinylcarbonyloxymethyl, acylaminomethyl such as benzoylamino, sulfonylaminomethyl such as benzenesulfonylaminomethyl, and hydroxymethyl. Examples of suitable A include tetrahydrofuran-2-yl, 5-oxo-tetrahydrofuran-2-yl, 4-methyl-tetrahydrofuran-2-yl, 4-methylenetetrahydrofuran-2-yl, 4-hydroxymethyl-tetrahydrofuran-2-yl, 4-(pyrrolidinecarbonylmethyl) tetrahydrofuran-2-yl, 4-[(benzoylamino)methyl]-tetrahydrofuran-2-yl, 4-[(benzenesulfonylamino)methyl] tetrahydrofuran-2-yl, 3-oxo-5-methyltetrahydrofuran-2-yl, 3-oxo-5-benzyltetrahydrofuran-2-yl, 3-oxo-5-phenyltetrahydrofuran-2-yl, 3-hydroxy-5-phenyltetrahydrofuran-2-yl, 5-methyl-3-[(4-methoxy) phenyl]tetrahydrofuran-2-yl, 5-methyl-3-aminotetrahydrofuran-2-yl, 4-(1-pyrrolidinyl)

tetrahydrofuran-2-yl, tetrahydrofuran-3-yl, 2,2-dimethyl-5-oxo-tetrahydrofuran-3-yl, 2-tetrahydropyranyl, 2-tetrahydrothienyl-1,1-dioxide, 5-methyl-2-tetrahydrothienyl-1,1-dioxide, 2-thietanyl-1,1-dioxide, 2-thioxanyl-1,1-dioxide, methylisobenzofuranone, 2-dihydrobenzofuranyl, 2-benzo-1,3-oxolo-2-yl.

In another embodiment, Y is a bond or $C_{1-5}$alkylene optionally substituted with one to two groups selected from $R^a$. Suitably, Y is a bond, methylene, ethylene, propylene, butylene, isopropylene, isobutylene, each optionally substituted with one to two groups selected from $R^a$, preferably hydroxy or C1–3alkoxy.

In another embodiment $R^1$ is H, Cy optionally substituted with one to four substituents selected from $R^b$, $OR^5$, $OC(O)R^5$, $NR^dR^e$, $C(O)NR^dR^e$, $C(O)OR^5$, $C(O)NR^dR^e$, $NR^dC(O)R^5$. Suitable substituents for Cy include halogen, alkyl, haloalkyl, alkoxy, amino, and carboxyl. Examples of suitable $R^1$ are H, phenyl, 4-fluorophenyl, 4-chlorophenyl, 4-bromophenyl, 4-trifluoromethylphenyl, 4-t-butylphenyl, 3-trifluoromethylphenyl, 3,5-bis(trifluoromethyl)phenyl, 3,4-dimethylphenyl, 2-thienyl, hydroxy, methoxy, acetoxy, amino, methylamino, morpholinocarbonyl, benzyloxycarbonyl, benzylaminocarbonyl, dimethylaminocarbonyl, dibenzylaminocarbonyl, pyrrolidinocarbonyl, piperazinocarbonyl, 4-methylpiperazinocarbonyl, ethylaminocarbonyl, acetylamino, N-methylacetylamino, cyclohexyl, 4-chloro-3-nitrophenhl, 3-nitrophenyl, 4-methoxyphenyl, 3,5-dimethoxyphenyl, benzoxazolyl, thiazolyl, 4-methylthiazolyl, and pyrrolidinyl.

In another embodiment, $R^3$ is $C_{1-5}$alkyl-$Ar^1$ or $C_{1-5}$alkyl-$Ar^1$—$Ar^2$, wherein $Ar^1$ and $Ar^2$ are optionally substituted with one to four groups independently selected from $R^b$. In a preferred subset $R^3$ is $C_{1-3}$alkyl-$Ar^1$—$Ar^2$ optionally substituted with one to four groups independently selected from $R^b$. More preferably $R^3$ is $CH_2$—$Ar^1$—$Ar^2$ wherein at least one Ar is a phenyl, and wherein $Ar^1$ and $Ar^2$ are optionally substituted with one or two groups selected from $R^b$. A particularly preferred group of $R^3$ is substituted biphenylmethyl wherein one of the substituent(s) is located at the 2'-position of the biphenyl ring. Suitable $R^b$ substituents for Ar are hydroxy, alkoxy, cycloalkoxy, cyano, amino, carbamyloxy, alkoxycarbonyl, carboxy, aminocarbonyl, alkoxy-alkoxy, and halogen. Examples of $R^3$ include phenyl, benzyl, phenethyl, biphenylmethyl, 4-(1-morpholinocarbonyloxy)phenylmethyl, 4-(5-[1,3-dimethyl-2,4-pyrimidinedione])phenylmethyl, 4-(2-tert-butyloxycarbonylethyl)phenylmethyl, 4-(ethoxyethyl)phenylmethyl, 4-(hydroxymethyl)phenylmethyl, 4-(methoxymethyl)phenylmethyl, 3-(t-butoxy)phenylmethyl, 3-(t-butoxycarbonylmethoxy)phenylmethyl, 4-(1-pyrrolidincarbonyloxymethyl)phenylmethyl, 3-(2-ethoxyethoxy)phenylmethyl, 3-(2-methoxyethoxy)phenylmethyl, 3-(1-pyrrolidinecarbonyloxy)phenylmethyl, 4-(4'-methoxyphenoxy)phenylmethyl, 4-(3'-methoxyphenoxy)phenylmethyl, 4-(2'-methoxyphenoxy)phenylmethyl, 4-(1-pyrid-2(1H)one)phenylmethyl, 4-(2,6-dichlorobenzamido)phenylmethyl, 4-(4-(2'-cyano)biphenylmethyl, 4-(2'-methoxy)biphenylmethyl, 4-(4'-fluoro)biphenylmethyl, 4-(2'-trifluoromethanesulfonyl) biphenylmethyl, 4-(2'-cyclopropoxy)biphenylmethyl, 4-(2', 6'-dimethoxy)biphenylmethyl, 4-(2',6'-diethoxy) biphenylmethyl, 4-(2'-benzyloxy)biphenylmethyl, 4-(2'-n-propoxy)biphenylmethyl, 4-(2'-cyano)biphenylmethyl, 4-(2'-n-propoxy-6'-methoxy)biphenylmethyl, 4-(2'-cyclopropylmethoxy-6'-methoxy)biphenylmethyl, 4-(2'-cyclobutylmethoxy-6'-methoxy)biphenylmethyl, 4-(2'-cyclohexylmethoxy-6'-methoxy)biphenylmethyl, 4-(2'-ethoxy-6'-methoxy)biphenylmethyl, 4-(2'-n-butoxy-6'-methoxy)biphenylmethyl, 4-(2',6'-dipropoxy) biphenylmethyl, 4-(2',6'-bis(cycloproxy))biphenylmethyl, 4-(2'-methoxy-5'-chloro)biphenylmethyl, 4-(2'-methoxy-3'-fluoro)biphenylmethyl, 4-(2'-fluoro-3'-methoxy) biphenylmethyl, 4-(2-thiazolyl)phenylmethyl, 4-(2,6-dimethoxy-4-pyrrolidinylmethylphenyl)phenylmethyl, 4-(2, 6-dimethoxy-4-piperazinylmethylphenyl)phenylmethyl, 4-(2,6-dimethoxy-4-(4-methylpiperazinyl)methylphenyl) phenylmethyl, 4-(2,6-dimethoxy-4-(1-triazolyl) methylphenyl)phenylmethyl, 4-(2,6-dimethoxy-4-morpholinylmethylphenyl)phenylmethyl, 4-(2,6-dimethoxy-4-aminomethylphenyl)phenylmethyl, 4-(2,6-dimethoxy-4-(piperazinylcarbonyloxymethyl)phenyl) phenylmethyl, 4-(2,6-dimethoxy-4-(pyrrolidinylcarbonyloxymethyl)phenyl)phenylmethyl, 4-(2,6-dimethoxy-4-(dimethylaminoqarbonyloxymethyl) phenyl)phenylmethyl, 4-(2,6-dimethoxy-4-hydroxylmethylphenyl)phenylmethyl, 4-(2,6-dimethoxy-4-methoxymethylphenyl)phenylmethyl.

In one preferred subset of compounds of formula I are compounds of formula Ia:

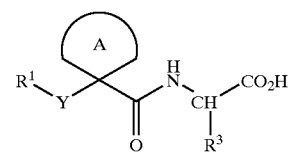

Ia or a pharmaceutically acceptable salt thereof, wherein

A is a 4- to 8-membered monocyclic saturated heterocyclic ring having one to two heteroatoms chosen from O, S and $S(O)_m$, optionally substituted with one to four substituents independently selected from oxo and $R^b$;

Y is
(1) a bond, or
(2) $C_{1-5}$alkylene optionally substituted with one to four groups independently selected from $R^a$;

$R^1$ is
(1) H,
(2) Cy optionally substituted with one to four substituents independently selected from $R^b$;
(3) $OR^5$,
(4) $OC(O)R^5$,
(4) $OC(O)NR^dR^e$,
(5) $NR^dR^e$,
(6) $NR^dC(O)R^5$,
(7) $C(O)R^5$,
(8) $C(O)OR^5$,
(9) $C(O)NR^dR^e$;

$R^3$ is
1) $C_{1-10}$alkyl,
2) $Ar^1$,
3) $C_{1-10}$alkyl-$Ar^1$,
4) $Ar^1$—$Ar^2$,
5) $C_{1-10}$alkyl-$Ar^1$—$Ar^2$,
wherein the alkyl group is optionally substituted with one to four substituents selected from $R^a$, and $Ar^1$ and $Ar^2$ are optionally substituted with one to four substituents independently selected from $R^b$.
$R^1$, $R^3$, $R^5$, $R^a$, $R^b$, $R^d$, $R^e$, $Ar^1$ and $Ar^2$ are as defined under formula I.

In one preferred subset of formula Ia, A is tetrahydrofuranyl or tetrahydrothienyl each optionally substituted with one or two groups independently selected from C1–5alkyl, CH2OC(O)NR$^d$R$^e$, CH2NR$^d$C(O)R$^e$, CH2NR$^d$SO2R$^e$, CH2OR$^d$, CH2—Ar$^1$ (where Ar$^1$ is optionally substituted with one to two groups selected from R$^a$), NR$^d$R$^e$, OR$^d$ and oxo, where R$^a$, R$^d$, R$^e$ and Ar$^1$ are as defined under formula I. More preferably A is tetrahydrofuranyl.

In another preferred subset of formula Ia, Y—R$^1$ is selected from hydrogen, C$_{1-5}$alkyl, phenyl optionally substituted with one to three groups selected from R$^a$, C$_{1-5}$alkylene-R$^1$ (where R$^1$ is hydroxy, C$_{1-5}$alkoxy, C$_{1-5}$alkanoyloxy, NR$^d$R$^e$, C(O)NR$^d$R$^e$, NR$^d$C(O)C$_{1-5}$alkyl, or phenyl optionally substituted with one to three groups selected from R$^b$), C(O)NR$^d$R$^e$, C(O)OR$^5$, C(O)R$^5$.

In another preferred subset of formula Ia, R$^3$ is CH2—Ar$^1$, wherein Ar$^1$ is optionally substituted with one to three groups selected from R$^b$ More preferably, R$^3$ is benzyl optionally substituted with one to three groups selected from halogen, OR$^d$, OC(O)NR$^d$R$^e$, NR$^d$C(O)R$^e$, C$_{1-5}$alkyl optionally substituted with OC(O)NR$^d$R$^e$, C(O)OC$_{1-5}$alkyl, hydroxy and C$_{1-5}$alkoxy,.

In another preferred subset of compounds of formula Ia are compounds of formula Ib:

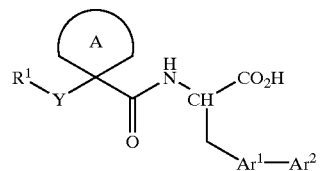

or a pharmaceutically acceptable salt thereof, wherein A, Y, R$^1$, Ar$^1$ and Ar$^2$ are as defined under formula Ia.

In one preferred subset of formula Ib, A is tetrahydrofuranyl or tetrahydrothienyl each optionally substituted with one or two groups independently selected from C$_{1-5}$alkyl, CH2OC(O)NR$^d$R$^e$, CH2NR$^d$C(O)R$^e$, CH2NR$^d$SO2R$^e$, CH2OR$^d$, CH2—Ar$^1$ (where Ar$^1$ is optionally substituted with one to two groups selected from R$^a$), NR$^d$R$^e$, OR$^d$ and oxo, where R$^a$, R$^d$, R$^e$ and Ar$^1$ are as defined under formula I. More preferably A is tetrahydrofuranyl.

In another preferred subset of formula Ib, Y—R$^1$ is selected from hydrogen, C$_{1-5}$alkyl, phenyl optionally substituted with one to three groups selected from R$^a$, C$_{1-5}$alkylene-R$^1$ (where R$^1$ is hydroxy, C$_{1-5}$alkoxy, C$_{1-5}$alkanoyloxy, NR$^d$R$^e$, C(O)NR$^d$R$^e$, NR$^d$C(O)C$_{1-5}$alkyl, or phenyl optionally substituted with one to three groups selected from R$^b$), C(O)NR$^d$R$^e$, C(O)OR$^5$, C(O)R$^5$.

In another preferred embodiment of formula Ib, Ar$^1$ is phenyl. More preferably Ar$^2$ is also phenyl, which is optionally substituted with one to three groups selected from R$^b$.

Examples of compounds of the present invention include:

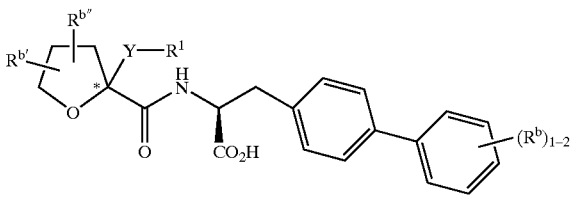

| R$^b$ | (*)/Y—R$^1$ | R$^{b'}$/R$^{b''}$ |
|---|---|---|
| 2-CN | (S) H | 5-oxo |
| 2-OCH$_3$ | (S) H | 5-oxo |
| 2-OCH$_3$ | CH$_2$Ph | H,H |
| 2-OCH$_3$ | CH$_2$CH$_2$Ph | H,H |
| 2-OCH$_3$ | Ph | H,H |
| 2-OCH$_3$ | CH$_3$ | H,H |
| CN | CH$_3$ | H,H |
| 2-CH$_3$O | H | H,H |
| 2-SO$_2$CF$_3$ | CH$_3$ | H,H |
| 2-O-cPr | CH$_3$ | H,H |
| 2-CH$_3$O | 4-F-Ph | H,H |
| 2-CH$_3$O | 2-thienyl | H,H |
| 2-CH$_3$O | 4-Cl-Ph | H,H |
| 2-CH$_3$O | 4-CF$_3$-Ph | H,H |
| 2-CH$_3$O | 4-Br-Ph | H,H |
| 2-CH$_3$O | 4-t-bu-Ph | H,H |
| 2-CH$_3$O | 3-CF$_3$-Ph | H,H |
| 2-CH$_3$O | 3,5-diCF$_3$-Ph | H,H |
| 2-CH$_3$O | 3,4-diCH$_3$-Ph | H,H |
| 2,6-diCH$_3$O | 4-Cl-Ph | H,H |
| 2,6-di(CH$_3$CH$_2$O) | (R) CH$_3$ | H,H |
| 2-PhCH$_2$O | (R) CH$_3$ | H,H |
| 2-CH$_3$CH$_2$CH$_2$O | (R) CH$_3$ | H,H |
| 2-CH$_3$O-6-n-C$_3$H$_7$O | (R) CH$_3$ | H,H |
| 2-CH$_3$O-6-(cPr—CH$_2$O) | (R) CH$_3$ | H,H |
| 2-CH$_3$O-6-(cBu-CH$_2$O) | (R) CH$_3$ | H,H |
| 2-CH$_3$O-6-(cHex-CH$_2$O) | (R) CH$_3$ | H,H |
| 2-CH$_3$O-6-CH$_3$CH$_2$O | (R) CH$_3$ | H,H |
| 2,6-bis(CH$_3$CH$_2$CH$_2$O) | (R) CH$_3$ | H,H |
| 2,6-bis(cPr-O) | (R) CH$_3$ | H,H |

-continued

| | | |
|---|---|---|
| 2-CH₃CH₂O-6-(n-C₄H₉O) | (R) CH₃ | H,H |
| 2,6-diCH₃O | CH₃ | H,4-CH₃ |
| 2,6-diCH₃O | CH₃ | 4-methylene |
| 2,6-diCH₃O | CH₃ | H,4- 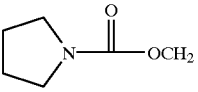 |
| 2,6-diCH₃O | CH₃ | H,4-PhC(O)NHCH₂ |
| 2,6-diCH₃O | CH₃ | H,4-PhSO₂NHCH₂ |
| 2,6-diCH₃O | CH₃ | H,4-CH₂OH |
| 2,6-diCH₃O | CH₃ | H,4- 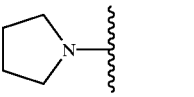 |
| 2,6-diCH₃O | CH₃ | H,4- 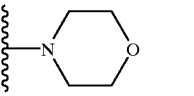 |
| 2,6-diCH₃O | CH₃ | 3-oxo, 5-CH₃ |
| 2,6-diCH₃O | CH₃ | 3-oxo, 5-CH₂Ph |
| 2,6-diCH₃O | CH₃ | 3-oxo, 5-Ph |
| 2,6-diCH₃O | CH₃ | 3-OH, 5-Ph |
| 2,6-diCH₃O | CH₃ | 5-CH₃, 3-(4-OCH₃)Ph |
| 2,6-diCH₃O | CH₃ | 5-CH₃, 3-NH₂ |
| 2,6-diCH₃O | CH₂CH₂OH | H,H |
| 2,6-diCH₃O | CH₂CH₂CH₂OH | H,H |
| 2,6-diCH₃O | CH₂CH₂OC(O)CH₃ | H,H |
| 2,6-diCH₃O | CH₂CH₂CH₂OC(O)CH₃ | H,H |
| 2,6-diCH₃O | CH₂CH₂OCH₃ | H,H |
| 2,6-diCH₃O | CH₂CH₂CH₂OCH₃ | H,H |
| 2,6-diCH₃O | (CH₂)₄OCH₃ | H,H |
| 2,6-diCH₃O | CH₂CH₂NH₂ | H,H |
| 2,6-diCH₃O | CH₂CH₂CH₂NH₂ | H,H |
| 2,6-diCH₃O | CH₂CH=CH₂ | H,H |
| 2,6-diCH₃O | (CH₂)₃CH₃ | H,H |
| 2,6-diCH₃O | CH(CH₃)₂ | H,H |
| 2,6-diCH₃O | CH₂CH(CH₃)₂ | H,H |
| 2,6-diCH₃O | CH₂CH₂NHCH₃ | H,H |
| 2,6-diCH₃O | 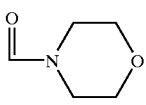 | H,H |
| 2-CH₃O | C(O)OCH₂Ph | H,H |
| 2-CH₃O | C(O)N(CH₂CH₃)₂ | H,H |
| 2-CH₃O | C(O)N(CH₂Ph)₂ | H,H |
| 2-CH₃O | 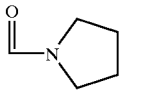 | H,H |
| 2-CH₃O | 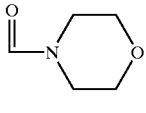 | H,H |
| 2-CH₃O | 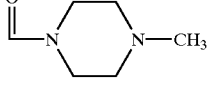 | H,H |
| 2,6-diCH₃O | CH(OH)CH(CH₃)₂ | H,H |
| 2,6-diCH₃O | CH(OCH₃)CH(CH₃)₂ | H,H |
| 2,6-diCH₃O | C(O)CH(CH₃)₂ | H,H |

-continued

| | | |
|---|---|---|
| 2,6-diCH$_3$O | CH$_2$CH$_2$CH$_2$NHCH$_3$ | H,H |
| 2,6-diCH$_3$O | CH$_2$CH$_2$CH$_2$N(CH$_3$)$_2$ | H,H |
| 2,6-diCH$_3$O | CH$_2$C(O)NHCH$_2$CH$_3$ | H,H |
| 2,6-diCH$_3$O | 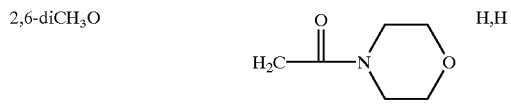 | H,H |
| 2,6-diCH$_3$O | (CH$_2$)$_3$NHC(O)CH$_3$ | H,H |
| 2,6-diCH$_3$O | (CH$_2$)$_3$N(CH$_3$)C(O)CH$_3$ | H,H |
| 2,6-diCH$_3$O | c-Hex | H,H |
| 2,6-diCH$_3$O | 3-NO$_2$-4-Cl-Ph | H,H |
| 2,6-diCH$_3$O | 3-NO$_2$-Ph | H,H |
| 2,6-diCH$_3$O | 4-OCH$_3$-Ph | H,H |
| 2,6-diCH$_3$O | 3,5-diOCH$_3$-Ph | H,H |
| 2,6-diCH$_3$O | 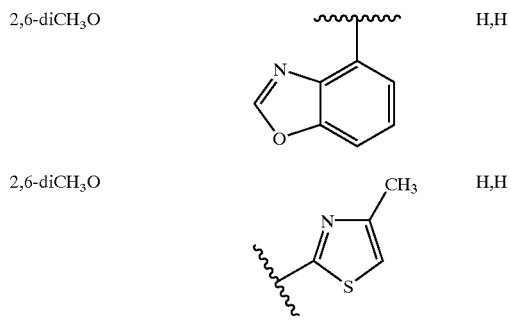 | H,H |
| 2,6-diCH$_3$O | 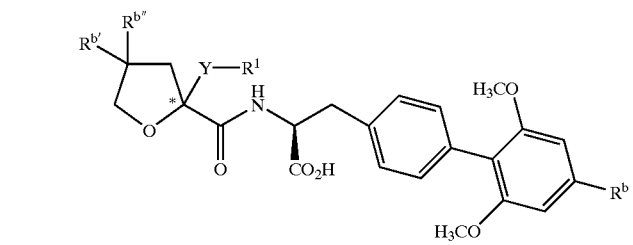 | H,H |

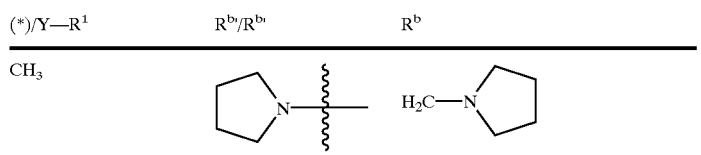

| (*)/Y—R$^1$ | R$^{b'}$/R$^{b''}$ | R$^b$ |
|---|---|---|
| CH$_3$ |  |  |
|  | H,H |  |
| (R)/CH$_3$ | H,H |  |
| (R)/CH$_3$ | H,H |  |
| (R)/CH$_3$ | H,H |  |
| (R)/CH$_3$ | H,H | 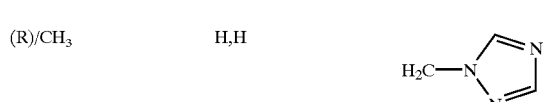 |

-continued
| | | |
|---|---|---|
| (R)/CH₃ | H,H | 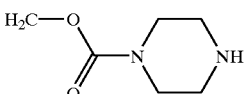 |
| (R)/CH₃ | H,H | 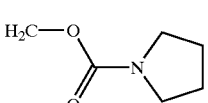 |
| (R)/CH₃ | H,H | 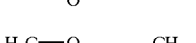 |
| (R)/CH₃ | H,H | 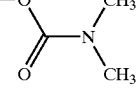 |
| (R)/CH₃ | H,H | 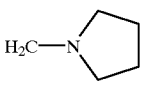 |
| (R)/CH₃ | H,H | 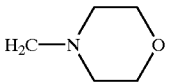 |
| (R)/CH₃ | H,H | CH₂NH₂ |
| 4-Cl-Ph | H,H | 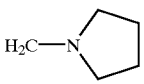 |
| 4-Cl-Ph | H,H | 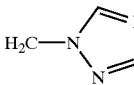 |
| 4-Cl-Ph | H,H | CH₂OH |
| 4-Cl-Ph | H,H | CH₂OCH₃ |
| 4-Cl-Ph | H,H | CH₂OC(O)N(CH₃)₂ |
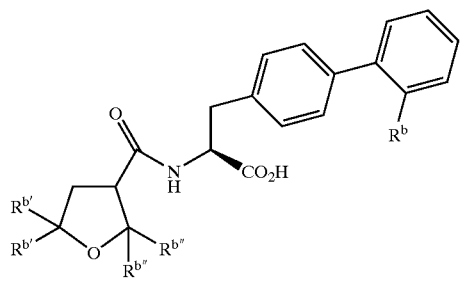
| $R^b$ | $R^{b'}/R^{b'}$ | $R^{b''}/R^{b''}$ |
|---|---|---|
| CN | H,H | H,H |
| OCH₃ | H,H | H,H |
| CN | O | CH₃,CH₃ |
| OCH₃ | O | CH₃,CH₃ |
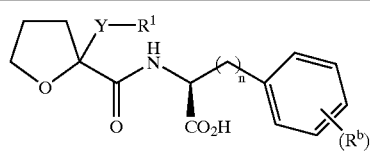
| n | $R^b$ | Y—$R^1$ |
|---|---|---|

-continued

| | | |
|---|---|---|
| 1 | 4-F | CH₃ |
| 1 | ![morpholine carbamate methyl] O-morpholine-C(O)-O-CH₂ | CH₃ |
| 1 | 1,3-diCH₃-5-CH₃-hexahydropyrimidine-4,6-dione | CH₃ |
| 1 | 2-thiazolyl | CH₃ |
| 1 | 4-(tBuO—C(O)—CH₂CH₂) | CH₃ |
| 0 | H | H |
| 1 | H | H |
| 2 | H | H |
| 1 | 4-(CH₂CH₂OCH₂CH₂O) | H |
| 1 | 4-OHCH₂ | CH₃ |
| 1 | 4-CH₃OCH₂ | CH₃ |
| 1 | 3-tBuO | CH₃ |
| 1 | pyrrolidine-N-C(O)-OCH₂ | CH₃ |
| 1 | 3-tBuOC(O)CH₂O | CH₃ |
| 1 | pyrrolidine-N-C(O)-O | CH₃ |
| 1 | 3-(CH₃CH₂OCH₂CH₂O) | CH₃ |
| 1 | 3-(CH₃OCH₂CH₂O) | CH₃ |
| 1 | 4-(4′-CH₃O-Ph-O) | H |
| 1 | 4-(3′-CH₃O-Ph-O) | H |
| 1 | 4-(2′-CH₃O-Ph-O) | H |
| 1 | 1-methyl-2-pyridon-yl | CH₃ |
| 1 | 4-(2′,6′-diCl-Ph-C(O)NH) | 4-Cl-Ph |
| 1 | 4-(1,3-diCH₃O-2-naphthyl) | CH₃ |

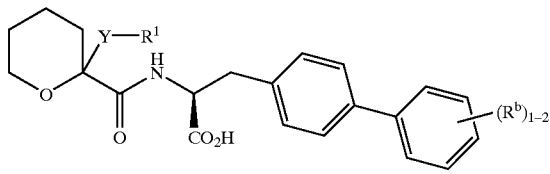

| Rᵇ | Y—R¹ |
|---|---|
| 2-CH₃O | H |
| 2-CH₃O | CH₃ |
| 2-CH₃O | PhCH₂ |
| 2-CH₃O | PhCH₂CH₂ |
| 5-Cl-2-CH₃O | CH₃ |
| 2,5-diCH₃O | CH₃ |

-continued
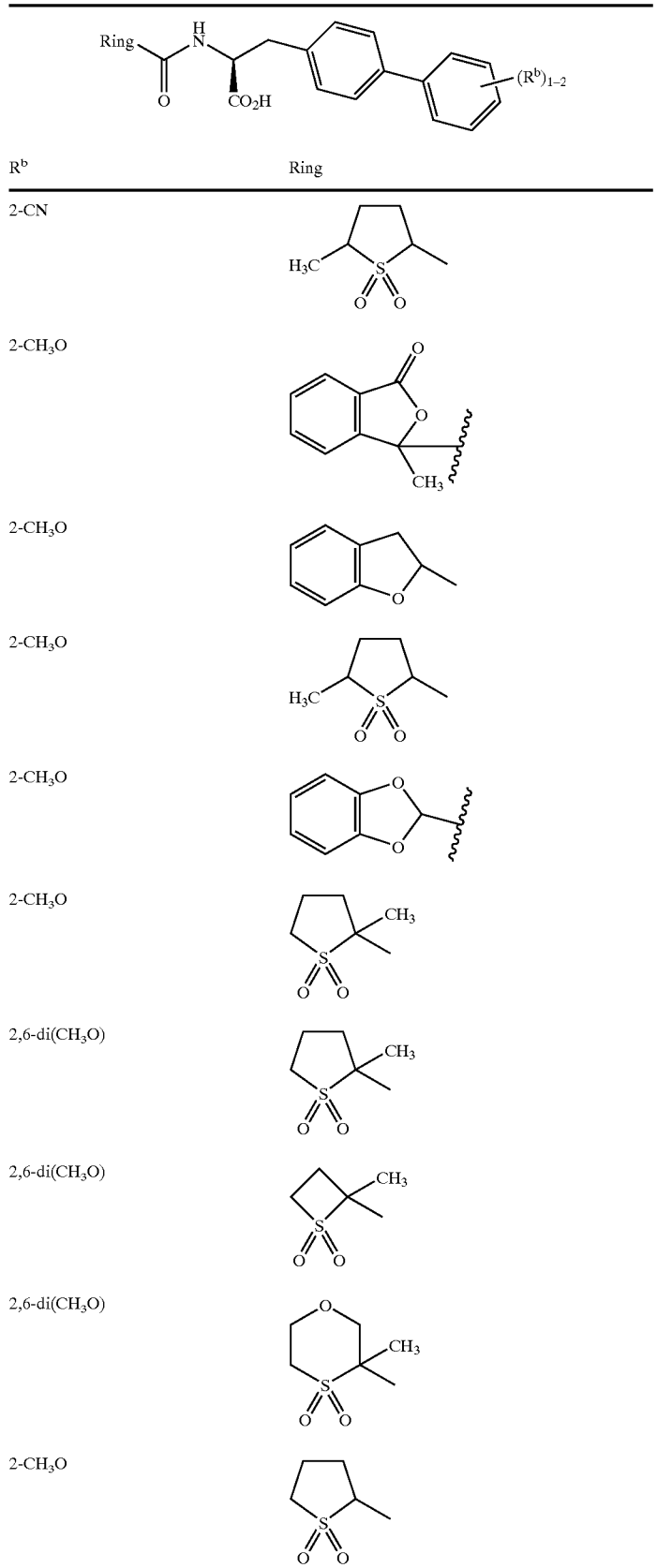

-continued
| 2,6-diOH | 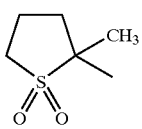 |
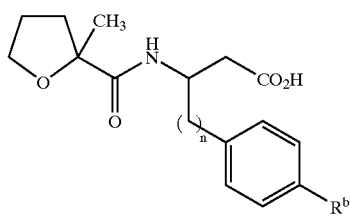
| n | Rb |
|---|---|
| 1 | H |
| 0 | H |
| 0 | 3'-F-2'-CH₃O-Ph |
| 0 | 2'-F-3'-CH₃O-Ph |
| 0 | CH₃O |
| 0 | CH₃CH₂OCH₂CH₂O |
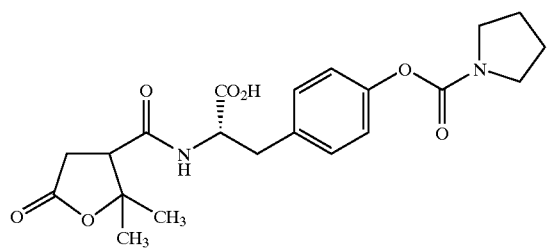
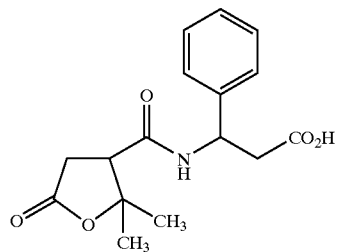
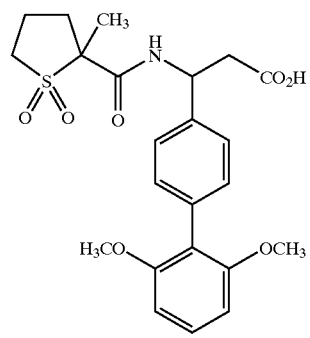

-continued

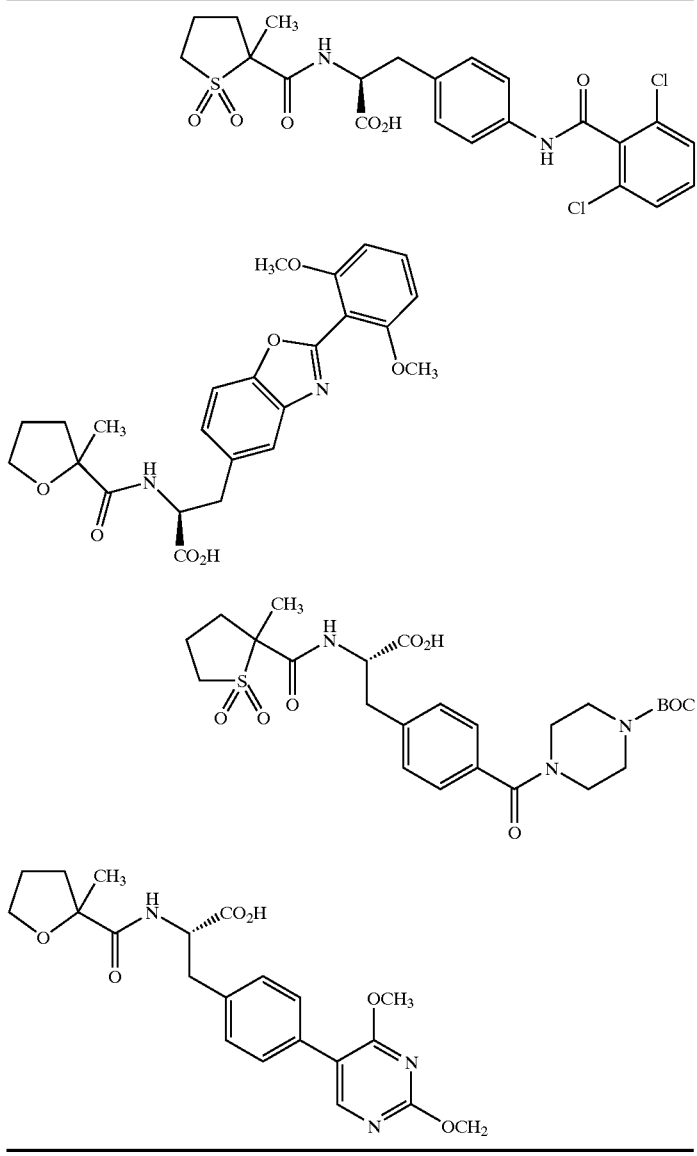

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkynyl include ethynyl, propargyl, 3-methyl-1-pentynyl, 2-heptynyl and the like.

Where an alkyl, alkenyl or alkynyl chain joins two other variables and is therefore bivalent, the terms alkylene, alkenylene and alkynylene are used.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term, also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha 4\beta 7$ integrin makes them useful for preventing or reversing the symptoms, disorders or diseases induced by the binding of VLA-4 and or $\alpha 4\beta\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) atherosclerosis, and (20) hepatitis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |

| | -continued |
| --- | --- |
| Benzalkonium chloride | 1.0 |
| Water for injection to a total volume of 1 mL | |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball (○). An N-Fmoc-protected amino acid derivative A (Fmoc=fluorenylmethoxycarbonyl) is loaded on to the appropriate hydroxyl-containing resin (the choice of resin being dependent on type of linker used, in this case Wang resin was utilized) using 1-ethyl-3-(3'-dimethylaminopropyl) carbodiimide (EDC) and 1-hydroxybenzotriazole (HOBt) in a solvent such as methylene chloride and teterahydrofuran or dimethylformamide (DMF) to give B. The Fmoc protecting group is removed with piperidine in DMF to yield free amine C. A carboxylic acid D is then coupled to the amine using a reagent such as 2-(1H-benzotriazole-1-yl)-1,1,3,3-tetramethyluronium hexafluorophosphate in the presence of HOBt and diisopropyl ethyl amine or any of the other well known amide coupling reagents under appropriate conditions: EDC, DCC or BOP (benzotriazole-1-yl-oxy-tris-(dimethylamino)-phosphoniumhexafluorophosphate) to give E. The final product is removed from the resin with strong acid (in this instance, trifluoroacetic acid (TFA in the presence of 5% water) to yield compounds of the present invention F.

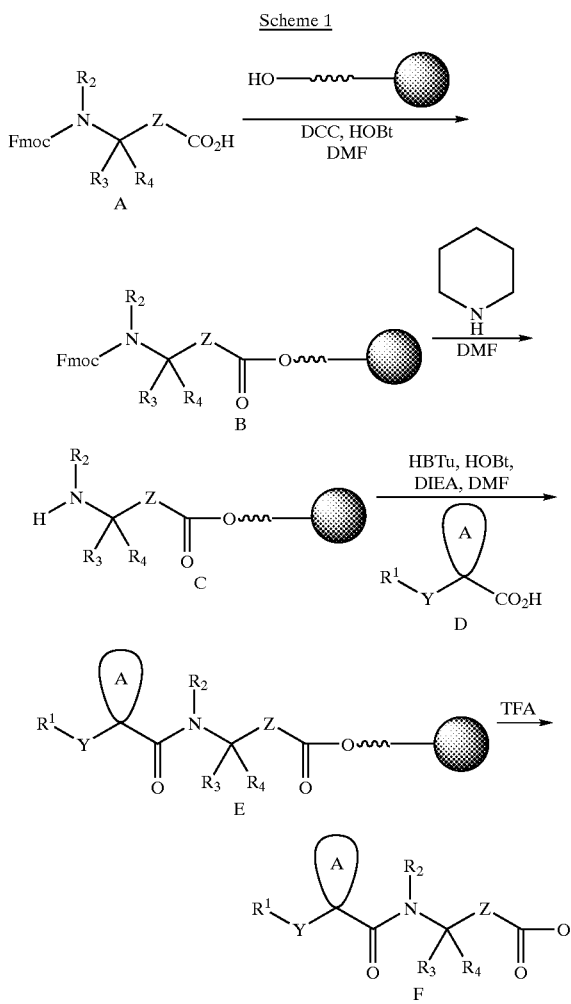

Scheme 1

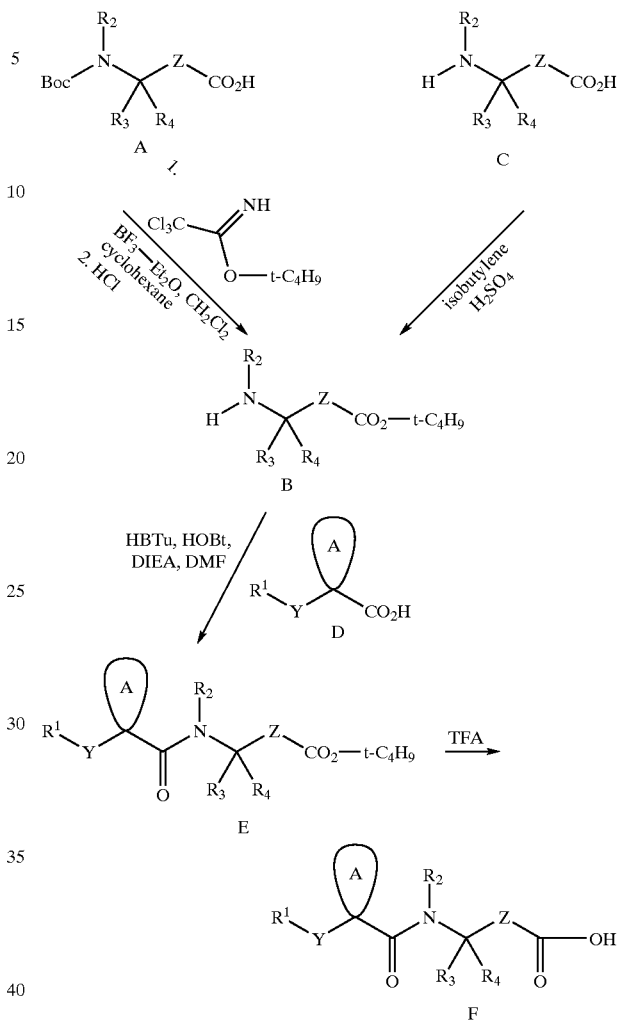

Scheme 2

Note: Methyl or ethyl esters may be used in place of t-butyl esters.
E to F by treatment with 1 equiv. NaOH or KOH.

In the second method (Scheme 2), standard solution phase synthetic methodology is outlined. Many amino acid derivatives are commercially available as the t-butyl or methyl esters and may be used directly in the synthesis outlined below. Amino acid t-butyl esters B may be prepared from amino acids C directly by treatment with isobutylene and sulfuric acid in diglyme or dioxane. Alternatively, N-Boc-protected amino acid derivative A (Boc=tert-butyloxycarbonyl) is treated with tert-butyl 2,2,2-trichloroacetimidate in the presence of boron trifluoride etherate followed by treatment with strong acid (HCl in ethyl acetate or sulfuric acid in t-butyl acetate) to remove the t-BOC group to yield tert-butyl ester B which is subsequently coupled to carboxylic acid D in the presence of 1-(3-dimethylaminopropyl)-3-ethylcarbodiimide hydrochloride (EDC), HOBt, and diisopropylethylamine (DIEA) in methylene chloride to yield amide E. The ester is then hydrolysed (in the case of t-butyl ester with 50% TFA in methylene chloride and for the methyl ester by treatment with 1N sodium hydroxide solution in methanol or dioxane) to provide compounds of the present invention F.

In a third method (Scheme 3), a late stage intermediate aryl bromide or iodide is coupled to an appropriately substituted aryl or heteroaryl boronic acid to give a subset of compounds of the present invention ($R^3$=biaryl-substituted-alkyl or heteroaryl-aryl-substituted-alkyl, $R^2$=hydrogen). For example, 4-iodo or 4-bromophenyl-derivative A is converted to the t-butyl ester B by treatment with isobutylene and sulfuric acid. Alternatively the N-Boc-4-iodo- or 4-bromo-phenyl-derivative C is reacted with tert-butyl 2,2,2-trichloroacetimidate in the presence of boron trifluoride etherate in methylene chloride-cyclohexane followed by treatment with strong acid (HCl in ethyl acetate or sulfuric acid in t-butyl acetate) to remove the t-BOC group to yield tert-butyl ester B which is subsequently coupled with C in the presence of (for example) EDC, HOBt and NMM to yield amide E. Substituted aryl or heteroaryl boronic acids are coupled to E in the presence of a palladium(0) reagent, such as tetrakis(triphenylphosphine)palladium under Suzuki conditions (N. Miyaura et al., *Synth. Commun.*, 1981, 11, 513–519), followed by removal of the tert-butyl ester using a strong acid (TFA) to yield the desired product F. If the aryl or heteroaryl boronic acid is not commercially available, but the corresponding bromide or iodide is, then the bromide or iodide can be converted into the desired boronic acid by treatment with an alkyllithium reagent in tetrahydrofuran at low temperature followed by addition of trimethyl or triisopropyl borate. Hydrolysis to the boronic acid can be effected by treatment of the intermediate with aqueous base and then acid.

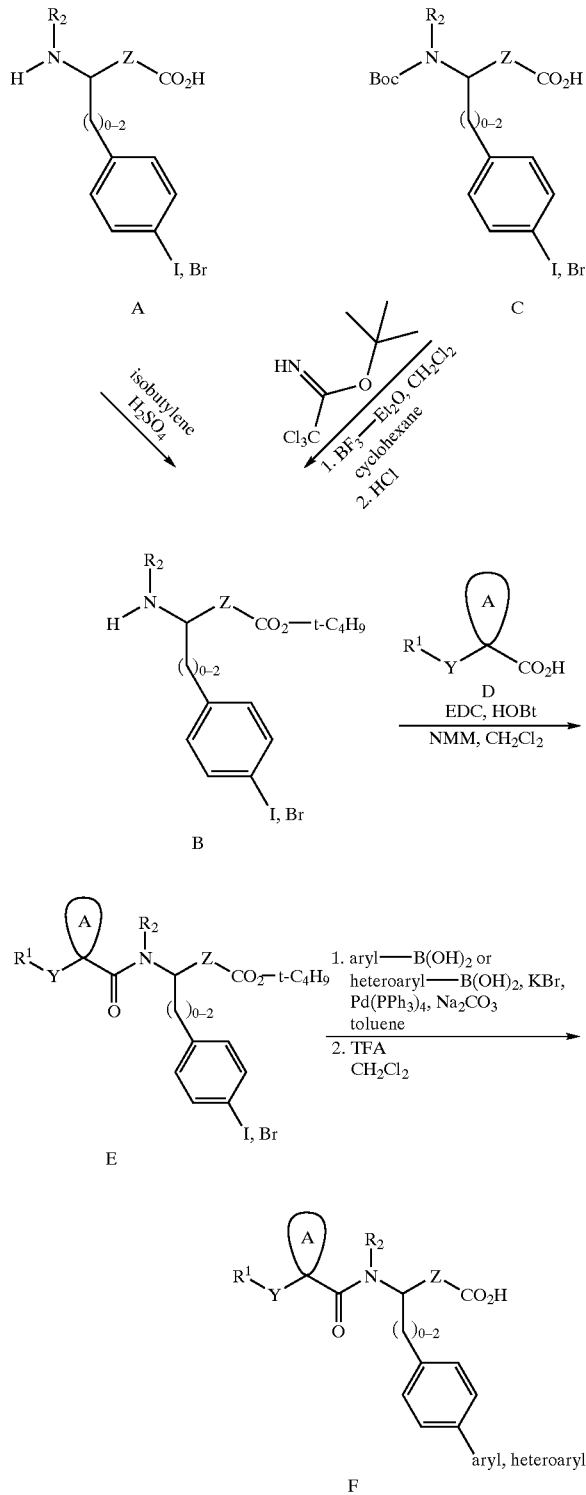

forming conditions (Scheme 4). (A. M. Echavarren and J. K. Stille, *J. Am. Chem. Soc.* 1987, 109, 5478–5486). The aryl bromide or iodide intermediate A is converted into its trialkyltin derivative B using hexamethylditin in the presence of a palladium(0) catalyst and lithium chloride and then reacted with an appropriately substituted aryl or heteroaryl bromide, iodide, or triflate in the presence of a palladium reagent, such as tetrakis(triphenylphosphine)-palladium(0) or tris(dibenzylideneacetone)dipalladium(0), in a suitable solvent, such as toluene, dioxane, DMF, or 1-methyl-2-pyrrolidinone, followed by the removal of the tert-butyl ester using strong acid (TFA) to yield the desired product C. Biphenyl amino acids suitable for attachment to resin (C where $R_1$ is fluorenylmethyloxy) may be prepared by this route as well. Superior coupling conversions and rates may be elicited by application of the method of Farina (*J. Org. Chem.* 5434, 1993)

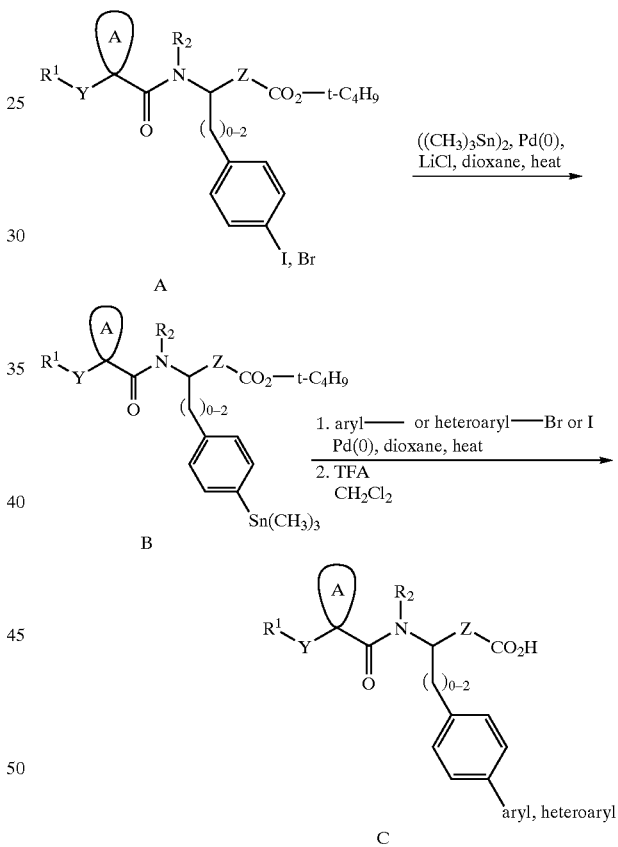

Alternatively, the aryl coupling reaction may be performed by application of Stille-type carbon—carbon bond Compounds wherein the middle ring is heteroaryl (G) may be prepared (Scheme 5) in a similar fashion starting from the appropriate heteroaryl bromide or iodide C using Suzuki-type conditions as depicted in Scheme 3 or from the corresponding heteroaryl trimethyltin using Stille-type conditions as depicted in Scheme 4. The requisite heteroaryl halides C may be prepared via conventional electrophilic halogenation of the N-Boc-heteroaryl-alanine tert-butyl ester intermediate B. B may be prepared from the known aliphatic iodo intermediate A in carbon—carbon bond formation using zinc/copper couple and palladium(II) (M. J. Dunn et al., *SYNLETT* 1993, 499–500).

Scheme 5

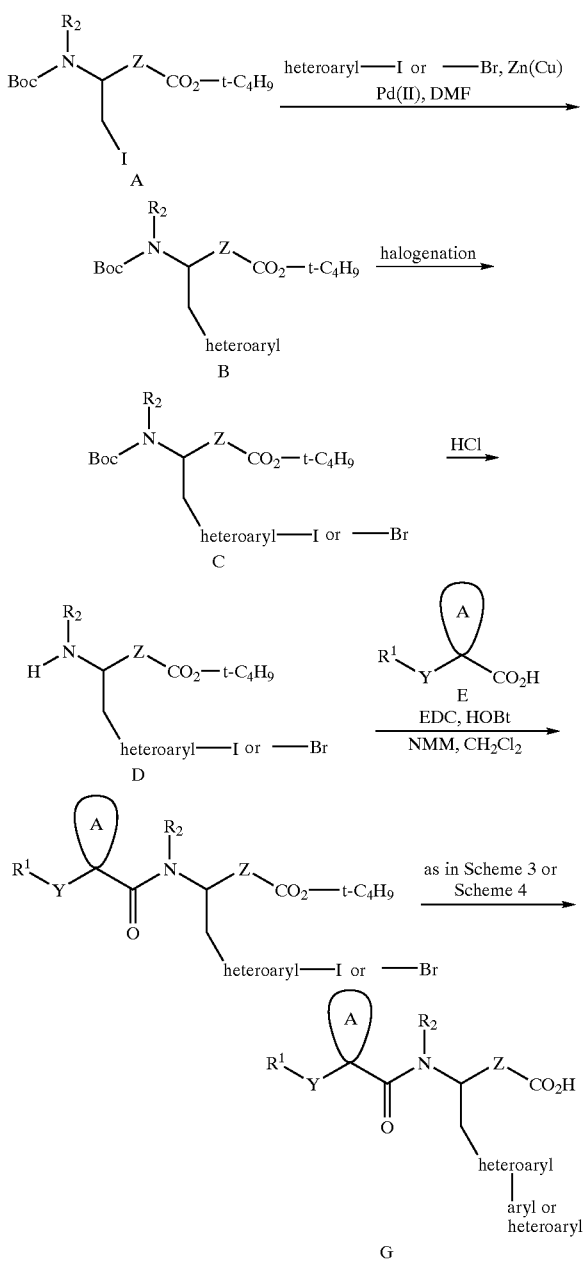

REFERENCE EXAMPLE 1

N-FMOC-(L)-4-(2'-Cyanophenyl)phenylalanine

Step A. N-FMOC-(L)-4-Iodophenylalanine, t-Butyl Ester.

To a solution of 15 g (51 mmol) of (L)4-iodophenylalanine in 100 ml of diglyme and 15 ml of concentrated $H_2SO_4$ was added 30 ml of condensed isobutylene. The vessel was agitated overnight and the crude product was diluted with 100 ml of ethyl acetate. The solution was added to excess sodium hydroxide solution while maintaining the temperature below 30° C. A white precipitate formed which dissolved upon addition of sodium hydroxide solution. The resulting mixture was filtered and the aqueous phase was extracted with ethyl acetate. The combined extracts were washed with brine and dried over anhydrous magnesium sulfate. The mixture was filtered and concentrated in vacuo to give a solution of the product in diglyme. The solution was diluted with 200 ml of ether and was treated with excess 1N HCl in ether with rapid stirring. The resulting precipitate was collected and dried in vacuo after washing with ether. A white solid (9.01 g) was collected of 4-iodo-phenylalanine t-butyl ester hydrochloride. To a suspension of 5.1 g (13.3 mmol) of the amine hydrochloride in 30 ml of methylene chloride was added 3.6 g (27 mmol) of diisopropyl ethyl amine followed by 3.43 g (0.013 g) of FMOCCl. The solution was stirred overnight at room temperature, washed with 1N HCl solution (3×50 ml), water (1×50 ml), saturated sodium carbonate solution (2×50 ml) and brine (1×50 ml). The solution was dried over $MgSO_4$, filtered and concentrated in vacuo to give 6.43 g of N-FMOC-(L)-4-iodophenylalanine, t-butyl ester as a white foam.

300 MHz $^1H$ NMR ($CDCl_3$): d 1.44 (s, 9 H); 3.05 (d, 2H);4.20–4.60 (m, 4 H); 5.30 (m, 1H); 6.90 (d, 2H), 7.30–7.80 (m, 12H).

Step B. N-FMOC-(L)-4-Trimethylstannyl-phenylalanine, tert-Butyl Ester.

In a dry 250 ml round bottom flask was added 6.20g (10.5 mmol) of the product of Step A, 0.48 g (115 mmol) LiCl and 0.6 g (0.52 mmol) of palladium tetrakistriphenylphosphine followed by 50 ml of dry dioxane. The mixture was stirred for 5 minutes. 5.2 g (15.8 mmol) of hexamethylditin was added and the reaction mixture was degassed and then heated at 90° C. The reaction mixture gave a black suspension after 15 minutes. Completion of the conversion was determined by TLC (10% EtOAc/hexanes; sm r.f.=0.3, product r.f.=0.4). The mixture was diluted with 100 ml of hexanes and stirred to give a precipitate. The suspension was filtered through celite and concentrated in vacuo to give a gum. The residue was purified by flash chromatography over silica gel eluting with 10% EtOAc/hexanes to give 5.02 g of the stannane (77% yield).

300 MHz $^1H$ NMR ($CDCl_3$): d 0.30 (s, 9 H); 1.45 (s, 9H); 3.20 (d, 2H), 4.20–4.60 (m, 4H); 5.29 (d, 1H); 7.12 (d, 2H); 7.22–7.45 (m, 6H); 7.59 (d, 2H), 7.75 (d, 2H).

Step C. N-FMOC-(L)-4-(2'-Cyanophenyl)phenylalanine, tert-Butyl Ester.

In a clean, dry round bottom flask fitted with a reflux condenser vented through a three way valve attached to a vacuum source and nitrogen gas was added 1.56 g (6.8 mmol) of 2-iodobenzonitrile, 0.117 (0.12 mmol) of tris (dibenzylidineacetone)-dipalladium (0), 0.8 g (19 mmol) of LiCl and 0.15 g (0.5 mmol) of triphenylarsine followed by 30 ml of N-methylpyrrolidinone (NMP). The mixture was degassed and stirred for 10 minutes at which time most of the catalyst mixture had dissolved. 3.9 g (6.21 mmol) of the product of Step B was added in 10 ml of NMP and the reaction was heated to 80° C. for 90 minutes. TLC (10% EtOAc/hexanes) indicated complete consumption of stannane (rf=0.4) and formation of the desired product (rf=0.1). The solution was cooled to room temperature and diluted with 50 ml of EtOAc. The solution was stirred with 20 ml of saturated KF for 20 minutes. The mixture was diluted with 200 ml of EtOAc and washed with water (6×75 ml), brine (1×50 ml) and was dried over $MgSO_4$. The mixture was filtered and concentrated in vacuo and the residue was purified by Biotage Flash chromatography over silica gel eluting with 20% EtOAc/hexanes to give 1.91 g (54% yield) of the title compound.

300 MHz 1H NMR ($CDCl_3$): d 1.45 (s, 9H); 3.19 (d, 2H); 4.20–4.68 (m, 4H); 5.40 (d, 1H); 7.25–7.55 (m, 12H); 7.65 (m, 2H), 7.80 (d, 2H).

Step D. N-FMOC-(L)-4-(2'-Cyanophenyl)phenylalanine.

2.4 g of the product of Step C was treated with 50 ml of a mixture of 50% trifluoroacetic acid in methylene chloride.

The reaction mixture was concentrated in vacuo. The residue was azeotropically dried by concentration from toluene to give the desired product as a foam.

300 MHz 1H NMR (CD$_3$OD): d 3.02 (dd, 1H); 3.30 (dd, 1H); 4.05–4.35 (m, 3H); 4.52 (m, 1H); 7.10–7.50 (m, 12H); 7.60 (m, 2H), 7.78 (d, 2H).

REFERENCE EXAMPLE 2

N-(FMOC)-(L)4-(2'-Methoxyphenyl)phenylalanine

Step A. N-(Boc)-(L)4-Iodo-phenylalanine, tert-Butyl Ester.

To a suspension of 7.5 g (0.019 m) of 4-iodophenylalanine t-butyl ester (Reference Example 1 Step A prior to treatment with HCl) in 100 ml of dichloromethane was added 2.52 g 0.019 m of diisopropyl ethyl amine followed by 4.14 g of ditertbutyldicarbonate. The reaction mixture was stirred overnight at room temperature, washed with 1N HCl (2×25 ml), water (2×25 ml), saturated NaHCO$_3$ (1×25 ml), brine (1×25 ml) and was dried over MgSO$_4$. The mixture was filtered and concentrated in vacuo to give the desired product as a gum 8.8 g (100% yield).

300 MHz $^1$H NMR (CDCl$_3$): δ 1.39 (s, 18H); 2.98 (AB, 2H); 4.4 (dd, 2H); 5.0 bd, 1H); 6.92 (d, 2H); 7.62 (d, 2H).

Step B. N-(Boc)-(L)-4-(2'-Methoxyphenyl)phenylalanine, tert-Butyl Ester.

7.97 g (0.018 m) of the product of Step A was dissolved in 160 ml of 2:1 toluene:ethanol. To this solution was added 2.99 g (0.0198 m) 2-methoxyphenylboronic acid, 0.69 g of tetrakistriphenylphosphine palladium (0) and 22.7 ml (0.45 m) of 2.0 M sodium carbonate in water. The reaction mixture was degassed three times and then heated at 90° C. for 90 minutes at which time the reaction mixture was black. The mixture was diluted with 300 ml of ethyl acetate, washed with water (3×150 ml) and brine (2×100 ml), and dried over MgSO$_4$. The mixture was filtered and concentrated in vacuo. The residue was purified by flash chromatography over silica gel eluting with 10% EtOAc/hexanes to give 6.89 g (88% yield) of the desired product as a white solid.

300 MHz 1H NMR (CDCl$_3$): δ 1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).

Step C. N-(FMOC)-(L)4-(2'-Methoxyphenyl)phenylalanine.

To a solution of 4.85 g (0.0113 m) of the product of Step B in 100 ml of t-butyl acetate was added 5.53 g (0.056 m) of concentrated sulfuric acid. The solution was stirred at room temperature for 2 hours and then carefully neutralized by addition of saturated aqueous NaHCO$_3$ solution. The solution was washed with NaHCO$_3$ solution, dried over NaSO$_4$, filtered and concentrated in vacuo. To a solution of 4.42 g of amine in 150 ml of methylene chloride was added at 0° C. 1.74 g (13.5 mmol) of diisopropylethyl amine followed by 3.48 g (13.5 mmol) of FMOCCl. The solution was stirred for 2 hours and washed with 1N HCl (3×50 ml), saturated NaHCO$_3$ solution (2×50 ml) and brine (1×50 ml). The mixture was filtered and concentrated in vacuo. The residue was purified by flash chromatography over silica gel eluting with a gradient of 10–25% EtOAc/hexanes to give 7.10 g (88% yield) of the desired product as a glass. The material was dissolved in 125 ml of 50% trifluoracetic acid/methylene chloride and stirred at room temperature for 2.5 hours. The solution was concentrated in vacuo and the residue was redissolved in toluene and concentrated in vacuo to give 7.01 g of the desired product. 96% pure by HPLC (254 nm).

300 MHz $^1$H NMR (CDCl$_3$): δ 3.20 (m, 2H); 3.76 (s, 3H); 4.21 (t, 1H); 4.41 (m, 4H); 4.76 (dd, 1H); 5.32 (d, 1H); 6.8–7.8 (m, 16H).

REFERENCE EXAMPLE 3

N-(FMOC)-(L)-4-(1-pyrrolidino-carbonyloxy) phenylalanine

Step A. N-(Boc)-(L)-Tyrosine tert-Butyl Ester.

To a solution of 9.82 g (0.041 m) of (L)-tyrosine, tert-butyl ester in 150 ml of methylene chloride and 20 ml of DMF was added 5.2 g (0.04 m) of triethyl amine followed by 9.03 g (0.04 m) of ditertbutyldicarbonate. The reaction mixture was stirred for 2 hours at room temperature and was then washed with 1 N HCl (3×50 ml), NaHCO$_3$ solution (1×50 ml) and brine (1×50 ml) and was dried over MgSO$_4$. The mixture was filtered and concentrated in vacuo to give 13.59 g (98% yield) of a white solid.

300 MHz $^1$H NMR (CDCl$_3$): 1.42 (s, 18H); 2.95 (d, 2H); 4.39 (dd, 1H); 5.01 (d, 1H); 6.15 (s, 1H); 6.70 (d, 2H); 7.00 d, 2H).

Step B. N-(Boc)-(L)-4-(1-Pyrrolidino-carbonyloxy) phenylalanine, tert-Butyl Ester.

To a solution of 8.18 g (0.024 m) of the product of Step A in a clean, dry flask dissolved in 100 ml of THF under a dry nitrogen atmosphere was added at 0° C. 25.5 ml (0.025 m) of a 1M solution of sodium hexamethyldisilazide in THF. The solution was stirred for 20 minutes. A solution of 3.2 g (0.024 m) of pyrrolidine carbamoyl chloride in 10 ml of THF was added. The reaction mixture was allowed to warm to room temperature and was stirred for 48 hours. The solution was diluted with 100 ml of ethyl acetate and was washed with 1N HCl (3×75 ml), saturated NaHCO$_3$ (1×75 ml), 1N NaOH (2×75 ml) and brine (1×75 ml) and was dried over MgSO$_4$. The mixture was filtered and concentrated in vacuo and the residue was recrystalized from ethyl acetate/hexanes to give 8.6 g of a white solid.

300 MHz 1H NMR (CDCl$_3$): δ 1.40 (s, 9H); 1.41 (s, 9H); 1.92 (m, 4H); 3.02 (d, 2H); 3.45 (t, 2H); 3.55 (t, 2H); 4.42 (dd, 1H); 4.99 (d, 1H); 7.05 (d, 211); 7.15 (d, 2H).

Step C. N-(FMOC)-(L)-4-(1-Pyrrolidino-carbonyloxy) phenylalanine.

The method of Reference Example 2 Step C was applied to 8.1 g (0.018 m) of the product of Step B to give 6.27 g of the title compound as a foam. 71% overall yield.

300 MHz 1H NMR (CDCl$_3$): δ 1.97 (bs, 4H); 3.12 (bd, 2H); 3.4–3.6 (2 bm, 4H); 4.20 (m, 1H); 4.30–4.50 (m, 2H); 4.69 m, 1H); 5.59 (t, 1H); 7.00–7.42 (m, 8H); 7.55 (bm, 2H); 7.77 (d, 2H).

REFERENCE EXAMPLE 4

(L)-4-(2'-Methoxyphenyl)phenylalanine, tert-Butyl Ester Hydrochloride

To a solution of 4.85 g (0.0113 m) of the product of Reference Example 2 Step B in 100 ml of t-butyl acetate was added 5.53 g (0.056 m) of concentrated sulfuric acid. The solution was stirred at room temperature for 2 hours and then carefully neutralised by addition of saturated aqueous NaHCO$_3$ solution. The solution was washed with NaHCO$_3$ solution, dried over NaSO$_4$, filtered and concentrated in vacuo. The residue was dissolved in 50 ml of ether and treated with anhydrous HCl gas with stirring to give a white precipitate. The solid was collected by filtration, washed with ether and dried in vacuo to give the desired product. 300 MHz $^1$H NMR (CD$_3$OD): 1.45 (s, 9H); 3.20 (d, 2H); 3.79 (s, 3H); 4.21 (t, 1H); 7.03 (m, 2H); 7.28 (m, 2H); 7.31 (d, 2H); 7.50 (d, 2H).

REFERENCE EXAMPLE 5

2-Methyl-2-tetrahydrofuroic Acid

To a solution of N,N-diisopropylamine (15 ml, 106 mmol) in THF (40 ml) at 0° C. was added n-BuLi (99 mmol, 1.6

M/Hex). After stirring the mixture for 30 min. DMPU (12 ml, 99 mmol) and tetrahydro-2-furoic acid (4.2 ml, 44 mmol) were added at 0° C. After 1 hr at 0° C., iodomethane (5.4 ml, 88 mmol) was added and the reaction mixture was allowed to warm to room temperature. After stirring overnight, the reaction mixture was partitioned between ethyl acetate and 1N HCl. The aqueous layer was extracted with ethyl acetate (2×500 ml) and chloroform (500 ml). The extracts were washed with brine, dried over $MgSO_4$, filtered, and concentrated. The residue was purified by silica gel chromatography with methylene chloride/methanol/acetic acid=97:3:0.5 to afford the desired product as an oil (2.5 g).

400 MHz $^1$H NMR ($CDCl_3$) δ 3.99 (m, 2H); 2.38 (m, 1H); 1.95 (m, 3H); 1.02 (s, 3H)

2-Benzyl-2-tetrahydrofuroic acid, 2-phenylethyl-2-tetrahydrofuroic acid, 2-methyl-2-tetrahydropyranoic acid, 2-benzyl-2-tetrahydropyranoic acid and 2-phenylethyl-2-tetrahydropyranoic acid were prepared by the alkylation procedures described for 2-methyl-2-tetrahydrofuroic acid in Reference Example 5 using commercially available alkyl- or aralkyl-halides and the corresponding carboxylic acid.

REFERENCE EXAMPLE 6

2-Tetrahydropyranoic Acid

To a vigorously stirred solution of tetrahydropyran-2-methanol (2.32 g, 40 mmol) in a mixture of $CH_3CN$ (20 ml), $CCl_4$ (20 ml) and water (10 ml) at 0° C. was added $NaIO_4$ (9.42 g, 44 mmol) and then $RuCl_3H_2O$ (414 mg, 2 mmol). After 20 min, the cooling bath was removed. After 40 min at room temperature, TLC showed reaction was complete. The reaction mixture was partitioned into ethyl acetate and ice-cold $Na_2S_2O_5$ solution. More $Na_2S_2O_5$ was added until all the brown material dissolved and a greenish mixture was obtained. The aqueous portion was extracted with more ethyl acetate and combined layer was washed with 10% $Na_2S_2O_5$, $H_2O$, brine, dried over $MgSO_4$, filtered and concentrated. The residue was purified by silica gel chromatography using methylene chloride/methanol/acetic acid= 95:5:0.5 to afford the product as an oil (1.5 g).

400 MHz $^1$H NMR ($CDCl_3$): δ 4.12 (m, 1H); 3.98 (m, 1H); 3.56 (m, 1H); 2.09 (m, 1H); 1.94 (m, 1H); 1.58 (m, 4H).

REFERENCE EXAMPLE 7

2-Phenyl-2-tetrahydrofuroic Acid

Step A. 2-Hydroxyl-2-phenyl-4-pentenoic Acid, Ethyl Ester.

The title compound was prepared according to a literature procedure (T. Akiyama, K. Ishikawa and S. Ozaki, *Chemistry letters* 1994, 627). To a solution of ethyl benzoylformate (2.5 g, 14.0 mmol) and allyl trimethylsilane (2.7 ml, 16.9 mmol) in 31 ml of methylene chloride (anhydrous) at −78° C. was added 1.6 ml of tin chloride (14.28 mmol) dropwise. The cooling bath was removed after the addition was complete. After the reaction mixture was stirred at room temperature for 5 min., TLC showed the reaction was complete. Triethylamine (3.5 ml) and water (150 ml) were added to quench the reaction. Extraction with ethyl acetate was complicated by the emulsion which was broken up by filtration through celite. The extracts were washed with brine, dried over $MgSO_4$, filtered, and concentrated. The residue was purified by silica gel chromatography with methylene chloride/hexane=2.5:97.5 to afford 2-hydroxyl-2-phenyl-4-pentenoic acid, ethyl ester as an oil (1.2 g). 400 MHz $^1$H NMR ($CDCl_3$): δ 7.59 (m, 2H); 7.29 (m, 3H); 5.79 (m, 1H); 5.13 (m, 2H); 4.23 (m, 2H); 2.96 (m, 1H); 2.74 (m, 1H); 1.26 (t, J=7.0 Hz, 3H).

Step B. 4-Isopropoxy-2-phenyl-2-tetrahydrofuroic Acid, Ethyl Ester.

To a 10 ml round bottom flask were placed $PdNO_2Cl(CH_3CN)_2$ (20 mg, 0.077 mmol) and $CuCl_2$ (20 mg, 0.308 mmol) and isopropyl alcohol (2.5 ml). The reaction vessel was purged with oxygen, fitted with an oxygen balloon and heated to 55° C. for 2 h. After cooling to 30° C., the homoallyl alcohol from Step A (356 mg, 1.54 mmol) was added in 5 ml of isopropyl alcohol and stirred overnight at 30° C. The catalyst was removed by filtration through $Al_2O_3$. The filtrate was concentrated and purified by preparative TLC using ethyl acetate/hexane=5:95 to give ethyl-4-isopropoxy-2-phenyl-2-tetrahydrofuroate as an oil (300 mg).

400 MHz 1H NMR ($CDCl_3$): δ 4.13 (m, 4H); 3.02 (m, 1H); 2.12 (m, 1H); 1.91 (m, 2H); 1.18 (m, 9H).

Step C. 2-Phenyl-2-tetrahydrofuroic Acid, Ethyl Ester.

To a solution of 4-isopropoxy-2-phenyl-2-tetrahydrofuroic acid, ethyl ester (189 mg, 0.68 mmol) in 4 ml of TFA was added triethylsilane (395 mg, 3.40 mmol). After heating at 70° C. for 4 h, the reaction mixture was poured into $NaHCO_3$ (saturated) and extracted with ethyl acetate. The extracts were washed with brine and dried over $MgSO_4$, filtered, and concentrated. The residue was purified by preparative TLC eluting with ethyl acetate/hexane=5:95 to give ethyl 2-phenyl-2-tetrahydrofuroate (170 mg).

400 Mhz $^1$H NMR ($CDCl_3$): δ 4.13 (q, J=7.5 Hz, 2H); 4.83 (m, 2H); 2.81 (m, 1H); 1.94 (m, 2H); 1.19 (t, J=7.5 Hz, 3H).

Step D. 2-Phenyl-2-tetrahydrofuroic Acid

To a solution of ethyl 2-phenyl-2-tetrahydrofuroate (170 mg, 0.77 mmol) in methanol (6 ml) was added 0.5N NaOH (1.5 ml, 0.75 mmol). After stirring at room temperature overnight, it was partitioned between dilute acetic acid and ethyl acetate. The aqueous layer was extracted with ethyl acetate and the combined organic layer was washed with brine and dried over $MgSO_4$, filtered and concentrated to afford the title compound as a white crystalline solid which was used without further purification. 400 MHz $^1$H NMR ($CD_3OD$): δ 7.54 (m, 2H); 7.34 (m, 3H); 4.07 (m, 2H); 2.79 (m, 1H); 2.18 (m, 1H); 1.98 (m, 2H).

REFERENCE EXAMPLE 8

2-(4-Fluorophenyl)-2-tetrahydrofuroic Acid

Step A. 4-Fluorobenzoyl Cyanide

This compound was prepared according to a literature procedure (M. M. Kayser et al., *J. Labelled Compd. Radiopharm.* 1987, 25, 301). CuCN (6 g, 67 mmol) and 4-fluorobenzoylchloride (8 ml, 67 mmol) were added to a sealed tube which was placed in an oil bath pre-heated to 140° C. The temperature was increased to 225° C. After 5 h, it was cooled, diluted with ethyl ether and filtered through a pad of celite. The filtrate was concentrated under reduced pressure and pumped to give a dark brown oil which was used in the subsequent hydrolysis step without further purification.

Step B. 4-Fluorophenyl Glyoxylic Acid

In a 250 ml round bottom flask were placed the crude 4-fluorobenzoyl cyanide (9 g, 67 mmol) and conc. HCl (46 ml). The mixture was stirred at room temperature. for 5 days. The resulting clear yellow solution was poured into 400 ml of ice water and extracted with ethyl acetate. The combined extracts were washed with water, dried over $MgSO_4$, concentrated under reduced pressure and pumped to give a yellow solid (8 g) which was used in the subsequent esterification step without further purification.

Step C. 4'-Fluorophenyl Glyoxylic Acid, Methyl Ester.

To a solution of 4-fluorophenyl glyoxylic acid (100 mg, 0.595 mmol) in ethyl ether (5 ml) was added trimethylsilyl diazomethane (2 M/hexane, 1 ml) at 0° C. TLC showed reaction was complete after 1 h. The ether was evaporated to leave a yellow oil. Chromatography with hexane/ether (95:5) gave methyl 4-fluorophenylglyoxalate as a pale yellow oil (75 mg). 500 MHz $^{13}$C NMR (CDCl$_3$): δ 184.11; 167.85; 165.79; 163.59; 133.04; 132.96; 128.97; 116.33; 116.16; 115.90; 115.72; 52.85.

Step D. 2-(4'-Fluorophenyl)-3-trimethylsilyl-2-tetrahydrofuroic Acid, Methyl Ester.

To a solution of allyl trimethyl silane (0.04 ml, 0.245 mmol) and methyl 4'-fluorophenylglyoxalete (40 mg, 0.204 mmol) in 1.5 ml of methylene chloride at −78° C. was added SnCl4 (0.224 ml, 0.224 mmol). The cooling bath was removed after the addition was complete. After 5 min at room temperature., the reaction was quenched by addition of triethylamine and water and extracted with ethyl acetate. The combined extracts were washed with brine, dried over MgSO$_4$, filtered and concentrated. The residue was purified by preparative TLC eluting with hexane/ethyl acetate=95:5 to give methyl-2-(4-fluorophenyl)-3-trimethylsilyl-2-tetrahydrofuroate (16 mg).

300 MHz $^1$H NMR (CDCl$_3$): δ 7.51 (m, 2H); 7.03 (m, 2H); 4.26 (t, 1H); 3.83 (dd, 1H); 3.72 (s, 3H); 2.38 (m, 2H); 1.31 (m, 1H); 0.00680 (s, 9H).

Step E. 2-(4-fluorophenyl)-2-tetrahydrofuroic Acid

To a solution of methyl-2-(4-fluorophenyl)-3-trimethylsilyl-2-tetrahydrofuroate (16 mg, 0.0541 mmol) in DMSO (0.5 ml) was added potassium t-butoxide (30 mg, 0.270 mmol). The resulting mixture was heated at 60° C. overnight. TLC showed reaction was complete. The reaction mixture was poured into HCl (1N) and extracted with ethyl acetate. The combined organic layer was dried over MgSO$_4$ and concentrated. The residue was purified by preparative TLC eluting with methylene chloride/methanol/acetic acid= 95:5:0.5 to give 2-(4-fluorophenyl)-2-tetrahydrofuroic acid (14 mg).

300 MHz $^1$H NMR (CDCl$_3$): δ 7.56 (m, 2H); 7.05 (m, 2H); 4.19 (m, 1H); 4.11 (m, 1H); 2.82 (m, 1H); 2.23 (m, 1H); 2.01 (m, 2H).

REFERENCE EXAMPLE 9

2-(2'-thienyl)-2-tetrahydrofuroic Acid

Step A. Thiophene-2-glyoxylic, Ethyl Ester.

Thiophene-2-glyoxylic acid (2 g, 12.8 mmol) was added to anhydrous ethanol (100 ml) which was saturated with HCl by bubbling HCl gas for 2 min. The resulting mixture was stirred at room temperature. overnight. TLC showed the reaction was complete. Solvent was removed and the residue was purified by chromatography over silica gel eluting with ethyl acetate/hexane 10:90 to give ethyl thiophene-2-glyoxylate (1.5 g).

Step B. 2-Hydroxy-2-(2-thienyl)-5-(tetrahydro-2H-pyranyloxy)-pentanoic Acid, Ethyl Ester.

Sec-BuLi (1.7 ml, 2.17 mmol, 1.3 M/cyclohexane) was added to a solution of 2-(3-bromopropoxy)tetrahydro-2H-pyran (254 mg, 1.09 mmol) in THF (6 ml) cooled to −50° C. After 30 min at −50° C., the reaction mixture was cooled to −78° C. and then transferred to a solution of ethyl thiophene-2-glyoxylate (200 mg, 1.09 mmol) in THF (6 ml) at −78° C. After stirring at −78° C. for 30 min, TLC showed reaction was complete. The reaction mixture was poured into NH$_4$Cl (saturated) and extracted with ethyl acetate. The extract was washed with water, brine, dried over MgSO$_4$ and concentrated. The residue was purified by silica gel chromatography using ethyl acetate/hexane 10:90 to afford the product as an oil (38 mg).

300 MHz $^1$H NMR (CDCl$_3$): δ 7.22 (dd, 1H); 7.18 (dd, 1H); 6.96 (dd, 1H); 4.57 (m, 1H); 4.28 (m, 2H); 3.79 (m, 2H); 3.43 (m, 2H); 2.19 (m, 2H); 1.85–1.52 (m, 8H); (t, 3H).

Step C. 2-(2'-Thienyl)-2-tetrahydrofuroic Acid, Ethyl Ester.

To a solution of 2-hydroxy-2-(2-thienyl)-5-(tetrahydro-2'H-pyranyloxy)-pentanoic acid, ethyl ester (38 mg, 0.116 mmol) in methylene chloride (1.5 ml) at −20° C. was added 2,6-lutidine and trimethylsilyl trifluoromethanesulfonate (0.023 ml, 0.128 mmol). The resulting solution was stirred at this temperature for 1 h. TLC showed reaction was incomplete. One more equiv of the reagents was added. TLC showed the reaction was complete after it was stirred for an additional 1 h. The reaction mixture was poured into HCl (0.5 N) and extracted with ethyl acetate. The extract was dried over MgSO$_4$, filtered and concentrated. The residue was purified by preparative TLC eluting with ethyl acetate/hexane 10:90 to 2-(2'-thienyl)-2-tetrahydrofuroic acid, ethyl ester (5 mg).

300 MHz $^1$H NMR (CDCl$_3$): δ 7.24 (dd, 1H); 7.08 (dd, 1H); 7.08 (dd, 1H); 6.96 (dd, 1H); 4.21 (q, 2H); 4.10 (m, 1H); 2.70 (m, 1H); 2.34 (m, 1H); 2.01 (m, 2H); 126 (t, 3H).

Step D. 2-(2'-thienyl)-2-tetrahydrofuroic Acid

To a solution of 2-(2'-thienyl)-2-tetrahydrofuroic acid, ethyl ester (5 mg, 0.0221 mmol) in methanol (0.5 ml) was added NaOH (0.066 ml, 0.0332 mmol, 0.5 N). After it was stirred at r. t. overnight, it was poured into water and acidified by adding glacial acedic acid dropwise until pH 4–5 was reached. The aqueous portion was extracted with ethyl acetate (2×50 ml). The extracts were dried over MgSO$_4$, filtered, and concentrated to give (2'-thienyl)-2-tetrahydrofuroic acid (3.5 mg) which was used in the subsequent reaction without further purification.

300 MHz $^1$H NMR (CDCl$_3$): δ 7.51 (m, 2H); 7.03 (m, 2H); 4.26 (t, 1H).

REFERENCE EXAMPLE 10

Resolution of 2-Methyl Tetrahydrofuran-2-carboxylic Acid

To a solution of racemic 2-methyl-2-tetrahydrofuranoic acid (50 g, 0.384 mole) in 75 mL of ethanol at −60° C. was added (S)-(−)-α-methylbenzylamine (0.384 mole, 50.5 mL of 98% pure material) dropwise via an addition funnel. Upon completion of the addition, the reaction mixture was stirred at −60° C. for another 30 minutes before 75 mL of cold acetone (−60° C.) was added. The precipitant was filtered over sintered glass (pore C) and the solids were washed with cold acetone (−60° C.). Some solid formed in the filtrate during the process. This was collected over sintered glass and washed as well with cold acetone. This process was repeated until no further material precipitated. Altogether, 88 g of a slightly reddish brown and tacky solid was obtained, wet with ethanol. All the funnels and adapters were carefully washed with methanol and the material collected, pumped down to dryness, redissolved in ethanol and added to the filtrate. Solvent was removed from this mixture until salt began to form. The salt was collected over sintered glass exhaustively as described above for the first batch. This provided 13 g more of the acid-amine salt.

The major batch obtained above (88 g) was dissolved in 240 mL hot (60–65° C.) ethanol and cooled to room temperature gradually. After 24 h, no crystals had formed. Crystallization was induced by gradual and careful cooling to 8° C. when fine needles began to form. This mixture, after filtration over sintered glass and washing with cold acetone (−60° C.), provided 10 g of a free-flowing salt. The filtrate obtained was put on the rotovap until crystal began to form in the flask. It was then allowed to crystallize at 6° C. This provided 3 g more of the salt. The filtrate was again placed on the rotovap but more ethanol was removed (so that more crystals were formed in the flask) before recrystallizing the mixture at 4–5° C. This was repeated and together obtained 30 g more of the salt after filtration and washing as described above. A total of 43 g of salt was obtained from the first recrystallization. This material was dissolved in 120 mL of hot ethanol and left standing at for 48 hr at room temperature. This provided very few needles. The flask was cooled slowly to 4° C. to induce more recrystallization. This mixture containing fine needles was filtered over sintered glass and washed with cold acetone (−60° C.). More needles formed in the filtrate after addition of the acetone. This was also collected over sintered glass and washed with cold acetone. The process was repeated until no more solid came out from the filtrate. The clear filtrate was put on the rotovap and solvents were removed until cloudiness formed in the flask. This was then cooled to 4° C. to coax out more crystals which was collected as described before. This process of crystallization was repeated until crystallization ceased. A total of 33 g of material was obtained from the second crystallization. This material was subjected to 85 mL of hot ethanol and recrystallized again. This time, a substantial amount of needles came out above room temperature. This was collected and the filtrate treated as described before for the previous recrystallizations to provide 29.8 g of a free-flowing material after the third recrystallization. This white powder was dissolved in 78 mL of hot ethanol for the fourth recrystallization. This time, needles came out at room temperature. The fine needles (15 g) were harvested and the filtrate treated as previously described, to provide a total of 27.6 g of a white powder after pumping. The needles were crushed before pumping as they had a tendency to impregnate ethanol. 40 mg of this material was treated with 0.5 mL of a 3.85 M ethyl acetate solution of hydrogen chloride (g) to liberate the acid. The amine salt was removed by trituration with ether followed by filtration over sintered glass. The acid thus obtained had the following optical activity: $[\alpha]^{20}_D = -9.49$ (c=0.78, MeOH), $[\alpha]^{20}_{578} = -10.38$ (c=0.78, MeOH). For use in subsequent reactions, the 2(R)-methyl tetrahydrofuran-2-carboxylic acid was liberated from the salt using a solution of hydrogen chloride(g) in ethyl acetate.

REFERENCE EXAMPLE 11

3(R)-amino-3-(4-biphenyl)propionic Acid, Methyl Ester

Step A. N-tert-Butoxycarbonyl-(S)4-hydroxyphenylglycine

To a solution of (S)-(4-hydroxyphenyl)glycine (Sigma Chemical) (6.5 g, 39 mmol) in dioxane/water (1:1, 120 mL) was added triethylamine (5,9 g, 8.2 mL, 58 mmol) and [2-(tert-butoxycarbonyloxyimnino)-2-phenylacetonitrile] (BOC-ON; 11 g, 45 mmol). After stirring overnight at room temperature, 300 mL of brine was added to the solution and the mixture was extracted with ether. (3×100 mL). The aqueous layer was acidified with HCl (pH=2) and extracted with 3×100 mL of ethyl acetate. The ethyl acetate layer was dried over MgSO$_4$, filtered and the solvent removed under reduced pressure. The residue was chromatographed with 98/2 to 95/5 methylene chloride/methanol. Recovered 12 g of crude product. The impurity was removed following esterification of the product in the next step.

400 MHz $^1$H NMR (CDCl$_3$): δ 1.37 (s, 9H), 5.1 (1H, br s), 6.7 (d, 2H, J=8 Hz), 7.15 (d, 2H, J=8 Hz).

Step B. N-tert-Butoxycarbonyl-(S)-4-hydroxyphenylglycine, Methyl Ester

In a 50 mL round bottomed flask was added a 1:1 mixture of benzene:methanol and N-tert-butoxycarbonyl-(S)-4-hydroxyphenylglycine (2.8 g, 11 mmol). The solution was cooled to 0° C. and a 2 M solution of trimethylsilyldiazomethane (Aldrich Chemical Co.) in hexane was added with vigorous stirring until a slight yellow color persisted. Then the reaction mixture solvents were removed under reduced pressure and the crude product was purified by flash chromatography (80/20 hexane/ethyl acetate) to give N-tert-butyloxycarbonyl-(S)-4-hydroxyphenylglycine, methyl ester (2.05 g, 7.3 mmol) (66% yield).

300 MHz $^1$H NMR (CDCl$_3$): δ 1.43 (s, 9H), 3.71 (s, 3H), 5.22 (br d, 1H), 5.57 (1H, br d), 5.80 (br s, 1H), (6.7 (d, 2H, J=8 Hz), 7.17 (d, 2H, J=8 Hz).

Step C. N-tert-Butoxycarbonyl-(S)-4-trifluoromethylsulfonyloxyphenylglycine, Methyl Ester To a 25 mL round bottom flask fitted with a stir bar and septum was added N-tert-butyloxycarbonyl-(S)-4-hydroxyphenylglycine, methyl ester (1.9 g, 6.8 mmol) and pyridine (2.8 mL, 33 mmol) in 12 mL of methylene chloride. The flask was purged with N$_2$, cooled to 0° and trifluoromethanesulfonic anhydride (1.38 mL, 7.8 mmol) was added dropwise over several minutes, keeping the temperature at or below 4° C. The solution was stirred for 1 h, then at room temperature for 4 h. The mixture was diluted with 20 mL of methylene chloride. The mixture was washed with 20 mL of 0.5 N sodium hydroxide, 1×20 mL of water and 2×20 mL of 10% citric acid. The organic layer was dried over anhydrous magnesium sulfate, filtered, and the solvent removed by rotoevaporation. Flash column chromatography on silica gel. eluted with 75/25 hexane/methylene chloride gave 2.3 g of the desired product (81% yield).

300 MHz $^1$H NMR (CDCl$_3$): δ 1.43 (s, 9H), 3.74 (s, 3H), 5.35 (1H, br d), 5.68 (br s, 1H), 7.27 (d, 2H, J=8 Hz), 7.47 (d, 2H, J=8 Hz).

Step D. N-tert-Butoxycarbonyl-(S)-(4-biphenyl)glycine.

To a 25 mL round bottom flask fitted with a stir bar and septum was added N-tert-butyloxycarbonyl-(S)-4-trifluoromethylsulfonyloxyphenylglycine, methyl ester (690 mg, 1.67 mmol), anhydrous potassium carbonate (348 mg, 2.6 mmol) and benzeneboronic acid (411 mg, 3.4 mmol) in 15 ml of toluene and 3 mL of ethanol. The mixture was degassed under nitrogen with three freeze-thaw cycles and tetrakis(triphenylphosphine) palladium (94 mg, 0.085 mmol) was added to the reaction mixture and the mixture was heated between 75–90° C. for 4 h. The solvent was removed under reduced pressure and the residue purified by flash column chromatography eluted with 85/15 hexane/ethyl acetate. Recovered 600 mg of the methyl ester (quantitative yield).

300 MHz $^1$H NMR (CDCl$_3$): δ 1.44 (s, 9H), 3.75 (s, 3H), 5.37 (1H, br d), 5.62 (br s, 1H), 7.36 (m, 1H), 7.45 (m, 4H), 7.57 (m, 4H).

The ester was hydrolyzed with 1.2 eq of potassium hydroxide in 10 mL of 4:1 ethanol: water (2 h). The solution was acidified with 2 N HCl (pH=2). The solvents were removed in vacuo and the free acid extracted with methylene chloride. 430 mg of the desired free acid was recovered (66% yield).

Step E. 3(S)-(4-Biphenyl)-3-(N-tert-butyloxycarbonyl) amino-1-diazo-propan-2-one.

To a 25 mL round bottom flask fitted with a stir bar and septum was added N-tert-butoxycarbonyl-(S)-4-biphenylglycine (430 mg, 1.31 mmol) in 10 mL of 2:1 methylene chloride: ether. The mixture was cooled to 0° C. and N-methyl-morpholine (159 μL, 1.44 mmol) was added, followed by dropwise addition of isobutylchloroformate (179 μL, 1.38 mmol). The mixture was stirred for 1 h at 0° C., then diazomethane in ether (excess, prepared from Diazald® by literature procedures) was added dropwise to the reaction mixture. The mixture was stirred for 1 h then quenched with saturated sodium bicarbonate. The mixture was extracted with ethyl acetate. (2×5 mL), washed with brine then dried over anhydrous magnesium sulfate. The mixture was filtered, the solvent removed under reduced pressure and the product isolated by flash column chromatography on silica gel eluted with 80/20 hexane/ethyl acetate to give 280 mg (0.78 mmol) of desired product (58% yield).

300 MHz 1H NMR (CDCl$_3$): δ 1.42 (s, 9H), 5.22 (bs, 1H), 5.29 (s, 1H), 5.9 (br s, 1H), 7.35–7.5 (m, 5H), 7.52–7.62 (m, 4H).

Step F. 3(R)-Amino-3-(4-biphenyl)propionic Acid, Methyl Ester

To a 25 mL round bottom flask fitted with a stir bar and septum was added 3(S)-(4-biphenyl)-3-(N-tert-butyloxycarbonyl)amino-1-diazo-propan-2-one (280 mg, 0.76 mmol), with 5 mL each of methanol and dioxane. The flask was cooled to 0° C. and 0.15 eq (34 mg, 0.038 mmol) of silver benzoate in 500 μL of triethylamine was added dropwise to the reaction mixture and the mixture allowed to stir at 25° C. for 1 h. The reaction was worked up with 10% ammonium hydroxide in saturated ammonium chloride (10 mL). Extract with ether (3×10 mL) and dry the organic layer over MgSO$_4$. Filter, reduce the volume and flash chromatograph with 85/15 hexane/ethyl acetate. Recovered 260 mg of product (98% yield). Take this material and dissolve it in 10 mL of 1 N hydrochloric acid in ethyl acetate. After stirring 2 h at room temperature, 180 mg of 3(R)-amino-(4-biphenyl)propionic acid, methyl ester hydrochloride was obtained.

300 MHz $^1$H NMR (CD$_3$OD): δ 2.90 (dd, 1H, J=18 Hz, J=6 Hz), 3.02 (dd, 1H, J=18 Hz, J=6 Hz), 3.66 (s, 3H), 5.9 (br s, 1H), 7.33–7.5 (m, 5H), 7.55–7.6 (m, 4H).

REFERENCE EXAMPLE 12

3(R)-Amino-3-(4-hydroxphenyl)propionic Acid, Methyl Ester, Acetic Acid Salt

Step A. 4-Benzyloxyphenyldiazoniumtetrafluoroborate.

In a 250 mL round bottomed flask fitted with a stir bar was added 4-benzyloxyaniline (8.7 g, 43.6 mmol), 150 mL of ethanol and 17 mL of 48% fluoroboric acid. Cool to 0° C. Then isoamyl nitrite (6,64 mL, 50 mol) was added dropwise over 15 minutes, keeping the solution temperature below 8° C. Stir 2 h at 0–4° C. The product precipitated out of solution. Diluted the reaction mixture with 100 mL ether and filter the reaction mixture. Wash the precipitate with 2×50 mL of ether. Recovered 10.3 g (79%) of product. Melting point=137° (dec), Lit.=140–142° (dec).

Step B. 4-Benzyloxycinnamic Acid, Methyl Ester

The following reaction was adapted from M. Beller and K. Kuhlein, *Synlett*, p 441 (1995). In a 50 mL round bottomed flask fitted with a stir bar and septum was added 4-benzyloxyphenyldiazoniumtetrafluoroborate (3.0 g, 10.2 mmol) and methyl acrylate (1.72 g, 0 mmol) in 15 mL of methanol. Subsequently, 10% palladium on carbon (250 mg, 0.2 mmol) was added to the mixture and it was heated at 55–60° C. until nitrogen gas evolution ceased (2 h) then overnight at 50° C. The reaction was cooled to room temperature, the catalyst filtered off and washed with methanol. The solvent is removed under reduced pressure and the residue purified by flash chromatography (90/10 hexane/ ethyl acetate) Recovered 2.0 g of the desired product (70% yield).

400 MHz $^1$H NMR (CDCl$_3$): δ 3.78 (s, 3H), 5.08 (s, 2H), 6.25 (d, 1H, J=17 Hz), 6.29 (d, 1H, J=9 Hz), 7.3–7.4 (m, 5H,), 7.45 (d, 2H, J=9 Hz), 7.62 (d, 1H, J=14 Hz).

Step C. 3-(4-benzyloxyphenyl)-3(R)-[benzyl-(1(S)-phenylethyl)-amino]-propionic Acid, Methyl Ester This procedure was adapted from S. G. Davies and O. Ichihara, *Tetrahedron: Asymmetry*, 2, p 183 (1991). In a 100 mL round bottom flask fitted with a stir bar and rubber septum is added (S)-(-)-N-benzyl-1-phenylethylamine (1.69 g, 8.0 mmol) in 60 mL of anhydrous tetrahydrofuran. Cooled to 0° C. and flushed with nitrogen. n-Butyl lithium (2.5N solution in hexane, 3.2 mL) was added dropwise, keeping the temperature below 4° C. for 15 minutes after final base addition. Then cooled to −78° C. and slowly added 4-benzyloxycinnamic acid, methyl ester (1.07 g, 4.0 mmol) in 15 ml of dry tetrahydrofuran at such a rate that the solution temperature remaines below −60° C. Stirred for 15 minutes, then quenched with saturated ammonium chloride (5 mL). Warmed to room temperature and added 10 mL of saturated brine. Extracted with 2×25 mL of ether, dried over anhydrous magnesium sulfate. Filtration and evaporation gave a mixture of the adduct and excess amine as a pale yellow oil. Flash column chromatography on silica gel eluted with 90/10 hexane/ethyl acetate gave the desired product (1.25 g, 2.62 mmol) (66% yield.

400 MHz $^1$H NMR (CDCl$_3$): δ 1.19 (d, 2H, J=7 Hz), 2.50 (dd, 1H, J=13 Hz, J=10 Hz), 2.64 (dd, 1H J=13 Hz, J=6 Hz), 3.44 (s, 3H), 3.62 (q, 2H, J=15 Hz), 3.97 (q, 1H, J=6 Hz), 4.36 (dd, 1H, J=9 Hz, J=6 Hz), 5.03 (S, 2H), 6.93 (d, 2H, J=9 Hz), 7.2–7.5 (m, 17 H).

Step D. 3(R)-Amino-3-(4-hydroxphenyl)propionic Acid, Methyl Ester, Acetic Acid Salt To a 250 mL medium pressure Parr hydrogenation bottle was added 25 mL of methanol, 1 mL of glacial acetic acid, 100 mg of 10% palladium hydroxide on carbon and 3-(4-benzyloxyphenyl)-3(R)-[benzyl-(1(S)-phenylethyl)-amino] propionic acid, methyl ester (1.25 g, 2.6 mmol). The flask was evacuated then pressurized to 50 psi H$_2$. and shaken until no more H$_2$ uptake was observed (4 h). Filter the solution through Celite, wash the pad with methanol (50 mL) and concentrate the filtrate under reduced pressure. Recovered 660 mg of product (theoretical) which was used without further purification.

REFERENCE EXAMPLE 13

4-Chloro-4'-trifluoromethyl-butyrophenone

Magnesium metal (0.6 g, 24.4 mmol) was placed into a 25 mL round bottomed flask and was vigorously stirred under nitrogen for 24 hours. To this activated magnesium was added 1 mL of tetrahydrofuran and 4-bromobenzotrifluoride (0.5 g, 2.2 mmol) and the reaction was sonicated for 30 seconds during which time a deep red color formed. The solution was cooled to 0° C. and 3-bromobenzotrifluoride (4.5 g, 20 mmol) in 9 mL of tetrahydrofuran was added dropwise. The reaction was allowed to warm to room temperature and stirred for 1.5 hours then added to a solution of 4-chlorobutyryl chloride (9.4 g, 66.6 mmol) in 50 mL of tetrahydrofuran at −78° C. The reaction was allowed to warm to room temperature and stirred for 1 hour. The reaction was washed with water (50 mL), saturated aqueous sodium chloride (50 mL), dried over MgSO$_4$ and concentrated in vacuo. The residue was purified by flash chromatography (Biotage) over silica gel eluting with hexane/ethyl acetate (50:1) to give 2.3 g of the title compound as an oil.
$^1$H NMR (500 MHz, CDCl$_3$): δ 8.08 (d, 2H, J=8.3 Hz); 7.74 (d, 2H, J=8.0 Hz); 3.69 (m, 2H); 3.21 (m, 2H); 2.25 (m, 2H).

The following compounds were prepared by the procedures described in Reference Example 13 substituting the appropriate aryl bromide, 4-chloro-3'-trifluoromethylbutyrophenone and 4-chloro-3',4'-bis (trifluoromethyl)-butyrophenone.

REFERENCE EXAMPLE 14

2-(4-Chlorophenyl)-2-tetrahydrofuroic Acid

Step A. 2-(4-Chlorophenyl)-2-cyanotetrahydrofuran

Potassium cyanide (1.87 g, 28.78 mmol) was added to a solution of 4-chloro-4'-chloro-butyrophenone (5.00 g, 23.03 mmol) in 25 mL of methanol. After stirring for 3 days at room temperature, the reaction was poured into water (50 mL) and extracted with methylene chloride (3×50 mL). The organic layers were combined, washed with saturated aqueous sodium chloride (50 mL), dried over $MgSO_4$ and concentrated in vacuo. The residue was purified by flash chromatography (Biotage) over silica gel eluting with hexane/ethyl acetate (30:1) to give 3.52 g of the title compound as an oil. $^1$H NMR (500 MHz, $CDCl_3$): δ 7.47 (m, 2H); 7.38 (m, 2H); 4.24 (m, 2H); 2.74 (m, 1H); 2.33 (m, 1H), 2.15 (m, 2H).

Step B. 2-(4-Chlorophenyl)-2-tetrahydrofuroic Acid.

Potassium hydroxide (4.7 g, 84.9 mmol) was added to a solution of 2-(4-chlorophenyl)-2-cyanotetrahydrofuran (3.53 g, 16.98 mmol) in 25 mL of ethylene glycol. The reaction was stirred at 195° C. for 2.5 hours. The reaction was cooled and extracted with 25 mL of methylene chloride, which was discarded. The aqueous layer was made acidic with concentrated HCl. and extracted with methylene chloride (3×25 mL). These organics were combined, washed with saturated aqueous sodium chloride (25 mL), dried over $MgSO_4$ and concentrated in vacuo. Recrystallization from hexanes yielded 2.87 g of the title compound as a white crystalline solid. $^1$H NMR (500 MHz, $CDCl_3$): δ 11.15 (bs, 1H), 7.50 (d, 2H, J=8.4 Hz); 7.30 (d, 2H, J=8.5 Hz); 4.13 (q, 1H, J=7.5 Hz); 4.05 (q, 1H, J=7.5 Hz); 2.79 (m, 1H); 2.20 (m, 1H), 1.99 (m, 1H); 1.95 (m, 1H). $^{13}$C NMR (125 MHz, $CDCl_3$): δ 177.1, 138.6, 133.8, 128.3, 126.9, 86.7, 69.3, 37.4, 25.3.

The following compounds were prepared by the procedures described in Reference Example 14 substituting the appropriate butyrophenone: 2-(4-bromophenyl)-2-tetrahydrofuroic acid, 2-(4-tert-butylphenyl)-2-tetrahydrofuroic acid, 2-(4-trifluoromethylphenyl)-2-tetrahydrofuroic acid, 2-(3-trifluoromethylphenyl)-2-tetrahydrofuroic acid, 2-(3,5-bis(trifluoromethyl)phenyl)-2-tetrahydrofuroic acid, 2-(3,4-dimethylphenyl)-2-tetrahydrofuroic acid, 2-cyclohexane-2-tetrahydrofuroic acid, 2-(3-nitrophenyl)-2-tetrahydrofuroic acid, and 2-(3-nitro-4-chlorophenyl)-2-tetrahydrofuroic acid.

REFERENCE EXAMPLE 15

2-Methyl-tetrahydrothiophene 1,1-Dioxide-2-carboxylic Acid

Step A. 2-Carbobenzyloxytetrahydrothiophene 1,1-Dioxide

Tetramethylene sulfone (2.00 g, 16.64 mmol) and benzyl chloroformate (3.12 g, 18.30 mmol) were dissolved in 50 mL of tetrahydrofuran and cooled to −78° C. Lithium bis(trimethylsilyl)amide (33.2 mL, 33.2 mmol, 1.0M in tetrahydrofuran) was added to the mixture dropwise. The reaction was stirred for 30 minutes at −78° C. then allowed to warm to room temperature and stirred for 30 minutes. The reaction was quenched with 1N HCl (50 mL) and extracted with methylene chloride (3×30 mL). The combined extracts were washed with saturated aqueous sodium chloride (50 mL), dried over $MgSO_4$ and concentrated in vacuo. The residue was purified by flash chromatography (Biotage) over silica gel eluting with hexane/ethyl acetate (3:1) to give 2.70 g of the title compound as a colorless oil. $^1$H NMR (500 MHz, $CDCl_3$): δ 7.20 (m, 5H); 5.29 (d, 1H, J=12.1 Hz); 5.23 (d, 1H, J=12.2 Hz); 3.95 (t, 1H, J=7.8 Hz); 3.12 (m, 2H); 2.85 (m, 1H); 2.36 (m, 2H); 2.16 (m, 1H). $^{13}$C NMR (125 MHz, $CDCl_3$): δ 165.4, 134.8, 128.58, 128.55, 128.45, 68.3, 64.7, 51.5, 26.0, 20.4.

Step B. 2-Carbobenzyloxy-2-methyltetrahydrothiophene 1,1-Dioxide

2-Carbobenzyloxytetrahydrothiophene 1,1-dioxide (2.70 g, 10.62 mmol) and iodomethane (0.7 mL, 11.2 mmol) were dissolved in 200 mL of tetrahydrofuran and cooled to −78° C. Lithium bis(trimethylsilyl)amide (11.2 mL, 1.2 mmol, 1.0M in tetrahydrofuran) was added to the mixture dropwise. The reaction was stirred for 1 hour at −78° C. then allowed to warm to room temperature and stirred for 1 hour. The reaction was quenched with 1N HCl (25 mL) and extracted with methylene chloride (3×25 mL). The combined extracts were washed with saturated aqueous sodium chloride (25 mL), dried over $MgSO_4$ and concentrated in vacuo. The residue was purified by flash chromatography (Biotage) over silica gel eluting with hexane/ethyl acetate (2:1) to give 2.14 g of the title compound as a pale yellow oil. $^1$H NMR (500 MHz, $CDCl_3$): δ 7.36 (m, 5H); 5.27 (d, 1H, J=12.4 Hz); 5.20 (d, 1H, J=12.4 Hz); 3.21 (td, 1H, J=13.2, 8.1 Hz); 3.11 (ddd, 1H, J=5.9, 8.0, 13.7 Hz)); 2.83 (dt, 1H, J=7.1, 13.8 Hz); 2.28 (m, 1H); 2.10 (m, 1H); 1.98 (m, 1H): 1.62 (s, 3H). $^{13}$C NMR (125 MHz, $CDCl_3$): δ 168.4, 135.0, 128.6, 128.4, 128.2, 68.2, 67.1, 50.7, 34.0, 18.8, 18.3.

Step C. 2-Methyltetrahydrothiophene 1,1-Dioxide-2-carboxylic Acid

2-Carbobenzyloxy-2-methyltetrahydrothiophene 1,1-dioxide (2.14 g, 7.98 mmol) and palladium on carbon (10%, 1 g) were dissolved in 20 mL of ethyl acetate. The reaction was placed under a balloon of hydrogen gas and stirred for 16 hours. The reaction was filtered and concentrated in vacuo to give 1.07 g of the title compound as a white solid. $^1$H NMR (500 MHz, $CD_3OD$): δ 3.2 (m, 2H); 2.77 (dt, 1H, J=7.3, 14.2 Hz); 2.22 (m, 1H); 2.10 (m, 1H); 1.98 (m, 1H): 1.56 (s, 3H). $^{13}$C NMR (125 MHz, $CD_3OD$): δ 171.2, 68.3, 51.6, 34.8, 19.5, 19.0.

The following compounds were prepared by the procedure described in Example 15 substituting the appropriate sulfone: 2-methylthietane 1,1-dioxide-2-carboxylic acid, 2-methyl-1,4-thioxane-1,1-dioxide-2-carboxylic acid.

REFERENCE EXAMPLE 16

2-Methyl-4-methyl-2-tetrahydrofuroic Acid

Step A. 2-Methyl-4-methylene-2-tetrahydrofuroic Acid, Methyl Ester

At 0° C., to a solution of R(+)-methyl lactate (4.16 g, 40 mmole) and 1,1-bis(chloromethyl)ethene (5.00 g, 40 mmole) in 100 mL of DMF was added NaH (2.64 g, 110 mmole) in several batches at such a rate as to avoid overreaction. After 10 min, the ice bath was removed and the reaction mixture was allowed to stir at room temperature overnight. It was diluted with ether and poured into a mixture of 80 mL saturated aqueous ammonium chloride and ice. The phases were separated. Further extractions of the aqueous phase with ether twice was followed by washing the combined organic layers with water, brine, and drying over anhydrous magnesium sulfate. Careful removal of volatiles provided 6 g of crude product as a mixture of the desired compound and the endo-double bond isomer. Due to its volatility, chromatographic separation was not attempted. Atmospheric pressure distillation (bp 60° C.) provided 0.8 g of desired product. The product readily decomposed under heat. TLC: Rf=0.5 in 4:1 hexane:ethyl acetate.

500 MHz $^1$H NMR ($CDCl_3$): δ 1.53(s, 3H), 2.52(dm, J=15 Hz, 1H),.2.98 (dm, J=15 Hz, 1H), 3.75(s, 3H), 4.47(br s, 2H), 4.93(m, 1H), 5.01(m, 1H).

Step B. 2-Methyl-4-methyl-2-tetrahydrofuroic Acid

To a solution of 2-methyl-4-methylene-2-tetrahydrofuroic acid, methyl ester (156 mg, 0.5 mmol, obtained from Step A) in 0.25 mL of methanol was added 6 mg of 10% platinum oxide and hydrogenated at room temperature for 2 h. TLC indicated disappearance of all starting material and formation of a single new spot. Since this compound is expected to be very volatile, it was not isolated but used as the crude mixture from hydrogenation in the next reaction where the product would be an acid and be much less volatile.

The above reaction mixture was treated with 1.5 mmole of sodium hydroxide (0.12 mL of 12.5N NaOH) and allowed to stir at room temperature for 6 h. TLC indicated that all starting material was gone. After removal of the volatiles, the residue was treated with excess hydrogen chloride in ethyl acetate. The excess acid was removed by a stream of nitrogen, and the residue was pumped, pumped with methanol 3 times (to get rid of water). This provided 50 mg of a white solid. The NMR suggested this to be two pairs of diastereomers in 1:2 ratio. TLC: Rf=0.2 in 10:1 dichloromethane:methanol 500 MHz $^1$H NMR (CDCl$_3$): δ 0.92, 1.03 (d, J=6.7 Hz, 3H), 1.42, 1.47(s, 3H), 1.75(dd, J=12.6, 1.8 Hz, 1H), 2.11 (dd, J=12.4, 7.1 Hz, 1H), 2.55 (m, 1H), 3.55, 3.75(t, J=8.3 Hz, 1H), 4.05, 4.16(t, J=8.0 Hz, 1H).

REFERENCE EXAMPLE 17

2-Methyl-4-methylene-2-tetrahydrofuroic Acid

Step A. 2-Methyl-4-methylene-2-tetrahydrofuroic Acid, tert-Butyl Ester

At 0° C., to a solution of R(+)-tert-butyl lactate (2.0 g, 13.7 mmole) and 1,1-bis(chloromethyl)ethene (1.71 g, 13.7 mmole) in 33 mL of DMF was added NaH (0.69 g, 29 mmole) all at once. After 10 min, the ice bath was removed and the reaction mixture was allowed to stir at room temperature overnight. It was poured into a mixture of ice and ether. The phases were separated. Further extractions of the aqueous phase with ether twice was followed by washing the combined organic layers with water, brine, and drying over anhydrous magnesium sulfate. Volatiles were removed at low temperature under reduced pressure and the crude product was flash chromatographed over silica gel (gradient elution using 60–10/1 petroleum ether/ether) to provide 1.05 g of the desired compound as a clear liquid (39%), homogeneous by TLC (Rf=0.65 in 4:1 hexane:ethyl acetate); Mass Spectrum: EI m/e 198 (M$^+$), 142 (M-tBu)$^+$.

500 MHz $^1$H NMR (CDCl$_3$): δ 1.45 (s, 9H), 1.47(s, 3H), 2.44(d, J=5.8 Hz, 1H), 2.90 (d, J=5.7 Hz, 1H), 4.45 (m, 2H), 4.89(m, 1H), 4.97 (m, 1H).

Step B 2-Methyl-4-methylene-2-tetrahydrofuroic Acid

At 0° C., to a solution of 2-methyl-4-methylene-2-tetrahydrofuroic acid, tert-butyl ester dissolved in 0.3 mL dichloromethane was added 461 mL of a 1:1 solution of trifluoroacetic acid and dichloromethane. After 20 min, the ice bath was removed and the reaction mixture allowed to stir at room temperature for 5 h. The excess trifluoroacetic acid was removed by a stream of nitrogen, and the residue coevaporated with dichloromethane 3 times. The crude product was chromatographed via silica gel (gradient elution 0–12% MeOH/CH2Cl2) to give 55 mg of the desired acid as a glass (77%). Mass Spectrum: EI m/e 142 (M)$^+$.

500 MHz $^1$H NMR (CDCl$_3$): δ 1.57 (s, 3H), 2.58(dm, J=16 Hz, 1H), 2.62 (dm, J=16 Hz, 1H), 4.51 (br s, 2H), 4.99(m, 1H), 5.06 (m, 1H).

REFERENCE EXAMPLE 18

2-Methyl-4-(pyrrolidine-1-carbonyloxymethyl)-2-tetrahydrofuroic Acid

Step A. 2-Methyl-4-hydroxymethyl-2-tetrahydrofuroic Acid, tert-butyl Ester

2-Methyl-4-methylene-2-tetrahydrofuroic acid, tert-butyl ester (200 mg, 1 mmole) was dissolved in 4 mL of tetrahydrofuran, cooled to 0° C., and boranetetrahydrofuran complex (2.5 mL of a 1.0 M solution in tetrahydrofuran) was added dropwise via a hypodermic syringe. The ice bath was removed and the reaction mixture was allowed to stir at room temperature for 1.5 h when TLC (1/1 hexane/ethyl acetate) indicated almost complete disappearance of the starting material. The mixture was cooled to 0° C. again and treated dropwise with 1 mL of 30% aqueous hydrogen peroxide. After being stirred for 2 h at room temperature, the reaction mixture was diluted with ether and washed with 5% sodium bicarbonate. The phases were separated and the aqueous phase was reextracted with ether twice. The organic layers were combined and washed with water and brine and dried over anhydrous sodium sulfate. The crude product obtained after filtration and removal of volatiles was chromatographed (gradient elution using 4-1/1 hexane/ethyl acetate) to provide 120 mg (56%) of two pairs of diastereomers, inseparable cleanly by column chromatography. TLC: Rf=0.15 (4:1 hexane:ethyl acetate)

500 MHz $^1$H NMR (CDCl$_3$): δ 1.45 (2s, 3H), 1.49, 1.50 (2s, 9H), 1.54, 1.94 (2dd, J=13.1, 9.2 Hz, 1H), 2.14, 2.47 (2dd, J=13, 6.2 Hz; 13, 8.2 Hz, 1H), 2.56 (m, 1H), 3.62 (m, 2H), 3.76, 3.80 (2dd, J=9.0, 7.4 Hz, 8.7, 5.5 Hz, 1H), 4.10(m, 1H).

Step B. 2-Methyl-4-(pyrrolidine-1-carbonyloxymethyl)-2-tetrahydrofuroic Acid, tert-Butyl Ester 2-Methyl-4-hydroxymethyl-2-tetrahydrofuroic acid, tert-butyl ester (60 mg, 0.277 mmol, from Step A) was solved in 0.5 mL of pyridine and p-nitrochloroformate (61.5 mg, 0.305 mmole) was added. After being stirred at room temperature for 5 h, pyrrolidine (0.042 mL, 0.5 mmole) was added all at once. The yellow reaction mixture was stirred at room temperature overnight. The reaction mixture was then diluted with ethyl acetate, washed with 5% citric acid, water, brine, and dried over anhydrous magnesium sulfate. The crude product obtained after filtration and removal of volatiles was flash chromatographed via silica gel (gradient elution using 40-10/1 hexane/ethyl acetate). This provided a fraction (43 mg) containing mainly the desired product. This was used without further purification in the next reaction. TLC: Rf=0.5 (4:1 hexane:ethyl acetate).

500 MHz $^1$H NMR (CDCl$_3$): δ 1.44 (s, 3H), 1.48, (2s, 9H), 1.96 (br m, 4H), 1.56, 2.0 (dd, J=13, 8.9 Hz, 12.8, 4.5 Hz, 1H), 2.10, 2.46 (2dd, J=13.1, 8.3 Hz; 13, 7.3 Hz, 1H), 2.8 (m, 1H), 3.35, 3.40 (2m, 4H), 3.72, 3.79 (2m, 1H), 4.0 (m, 1H), 4.10(m, 2H).

Step C. 2-Methyl-4-(pyrrolidine-1-carbonyloxymethyl)-2-tetrahydrofuroic Acid

2-Methyl-4-(pyrrolidine-1-carbonyloxymethyl)-2-tetrahydrofuroic acid, tert-butyl ester (from Step B) was hydrolyzed as described in Reference Example 17, Step B to provide the title compound in a 72% yield after chromatographic purification. TLC: Rf=0.2 (10:1 dichloromethane:methanol)

500 MHz 1H NMR (CDCl$_3$): δ 1.44, 1.48 (2s, 3H), 1.88 (br m, 4H), 1.63, 2.06 (dd, J=13.1, 8.3 Hz, 13.1, 9.0 Hz, 1H), 2.17, 2.52 (2dd, J=13, 8 Hz; 13, 7 Hz, 1H), 2.68 (m, 1H), 3.34 (m, 4H), 3.72(m, 1H), 3.98–4.10 (m, 3H).

REFERENCE EXAMPLE 19

2-Methyl-4-benzoylaminomethyl-2-tetrahydrofuroic Acid

Step A. 2-methyl-4-azidomethyl-2-tetrahydrofuroic Acid, tert-butyl Ester

2-Methyl-4-hydroxymethyl-2-tetrahydrofuroic acid, tert-Butyl Ester (400 mg, 1.85 mmol, from Reference Example 18, Step A) was dissolved in 7.5 mL of toluene, and triethylamine (1.85 mmol, 187 mg) was added dropwise. After cooling to 0° C., methanesulfonyl chloride (1.85 mmol, 212 mg) was added and stirring was continued for 20 min. Subsequently, tetra-n-butylammonium bromide (1.85 mmol, 596 mg) and excess aqueous sodium azide (15.7 mmol, 1.02 g, dissolved in 3.7 mL water) was added. The mixture was stirred at 60° C. for 8 h. TLC (4/1 hexane/ethyl acetate) indicated the formation of new spot and the disappearance of most of the starting material. After being cooled to room temperature, the reaction mixture was diluted with ether and citric acid was added to attain $pH_5$. The phases were separated and the aqueous phase was reextracted with ether twice. The organic layers were combined and washed with brine and dried ($MgSO_4$). The residue obtained after filtration and removal of most of the volatiles was flash chromatographed (silica gel, gradient elution 50-20/1 hexane/ethyl acetate) to provide 280 mg (63%) of the azide. TLC: Rf=0.8 (4:1 hexane:ethyl acetate) 500 MHz $^1$H NMR ($CDCl_3$): δ 1.45 (s, 3H), 1.49, 1.50 (2s, 9H), 1.55, 2.0 (2dd, J=12.8, 8.0 Hz, 13.1, 9.0 fHz, 1H), 2.12, 2.50 (dd, J=13.1, 6.4 Hz, 12.8, 8.0 Hz, 1H), 2.60 (m, 1H), 3.35 (m, 2H), 3.68, 3.73(2dd, J=8.7, 5.7 Hz, 8.7, 7.5 Hz, 1H), 4.10 (m, 1H).

Step B. 2-Methyl-4-aminomethyl-2-tetrahydrofuroic Acid, tert-Butyl Ester

At room temperature, 2-methyl-4-azidomethyl-2-tetrahydrofuroic Acid, tert-butyl ester (330 mg, 1.37 mmol, from Step A) was dissolved in tetrahydrofuran (2.75 mL) and triphenylphosphine (1.40 mmol, 367 mg) was added batchwise over 10 min. After being stirred at room temperature for 2 h, water (2.1mmol, 0.038 mL) was added dropwise via a hyperdermic syringe. Stirring was continued at room temperature for 24 h when TLC indicated disappearance of all starting material. The volatiles were removed and the crude product was flash chromatographed to provide 198 mg (67%) of the desired amine as a clear oil. TLC: Rf=0.1 (4:1 hexane:ethyl acetate).

500 MHz 1H NMR ($CDCl_3$): δ 1.40 (2s, 3H), 1.45(2s, 9H), 2.0 (m, 1H), 2.35 (m, 1H), 2.48 (m, 1H), 2.70 (m, 2H), 3.65(m, 1H), 4.10 (m, 1H).

Step C. 2-Methyl-4-benzoylaminomethyl-2-tetrahydrofuroic Acid, tert-Butyl Ester

At room temperature, to a solution of 2-methyl-4-aminomethyl-2-tetrahydrofuroic acid, tert-butyl ester (30 mg, 0.139 mmole) was added benzoyl chloride (0.167 mmol, 24 mg) and N-methylmorpholine (0.334 mmol, 34 mg). After being stirred at room temperature for 2.5d, volatiles were removed and the residue was flash chromatographed through silica gel. The title compound was obtained in quantitative yield (47 mg). TLC: Rf=0.45 (1:1 hexane: ethyl acetate); Mass Spectrum: ESI m/e 320 $(M+1)^+$.

500 MHz 1H NMR ($CDCl_3$): δ 1.44, 1.49 (2s, 3H), 1.46, 1.47 (2s, 9H), 1.58, 2.02 (2m, 1H), 2.16, 2.53 (dd, J=13.3, 6.4 Hz, 12.8, 8.0 Hz, 1H), 2.70 (m, 1H), 3.48 (m, 2H), 3.76(m, 1H), 4.06 (m, 1H), 6.5, 6.7 (2 br s, 1H), 7.45(m, 2H), 7.50(m, 1H), 7.78(m, 2H).

Step D. 2-methyl-4-benzoylaminomethyl-2-tetrahydrofuroic Acid

2-Methyl-4-benzoylaminomethyl-2-tetrahydrofuroic acid, tert-butyl ester was hydrolyzed according to the procedure of Reference Example 17, Step B to provide the title compound. TLC: Rf=0.3 (10:1 dichloromethane:methanol); Mass Spectrum: ESI m/e 264 $(M+1)^+$.

500 MHz $^1$H NMR ($CDCl_3$): δ 1.50, 1.56 (2s, 3H), 1.70, 2.15 (2m, 1H), 2.24, 2.62 (2m, 1H), 2.72 (m, 1H), 3.50 (m, 2H), 3.80(m, 1H), 4.12 (m, 1H), 6.8, 7.0 (2 br s, 1H), 7.42(m, 2H), 7.54(m, 1H), 7.76(m, 2H), 7,80 (br s, 1H).

REFERENCE EXAMPLE 20

2-methyl-4-benzenesulfonylaminomethyl-2-tetrahydrofuroic Acid

The title compound was prepared according to the procedures described in Reference Example 19, substituting benzene sulfonyl chloride for benzoyl chloride in Step C. Mass Spectrum: ESI m/e 300 $(M+1)^+$, 255 $(M—CO_2H)^+$.

REFERENCE EXAMPLE 21

2-Methyl-4-oxo-2-tetrahydrofuroic Acid

Step A. 2-Methyl-4-oxo-2-tetrahydrofuroic Acid, tert-Butyl Ester

A solution of 2-methyl-4-methylene-2-tetrahydrofuroic acid, tert-butyl ester (200 mg, 1 mmole) in 20 mL of 1:1 dichloromethane:methanol was treated with ozone until the ozololysis of the exocyclic methylene was complete. The ozonide was decomposed via dimethylsulfide. Removal of the volatiles provided 198 mg of an oil, homogeneous on TLC (4/1 hexane/ethyl acetate).

500 MHz $^1$H NMR ($CDCl_3$): δ 1.47, (s, 9H), 1.61 (s, 3H), 2.40(d, J=8.1 Hz, 1H), 2.80 (d, J=8.0 Hz, 1H), 4.12 (d, J=15 Hz, 2H).

Step B. 2-Methyl-4-oxo-2-tetrahydrofuroic Acid

2-Methyl-4-oxo-2-tetrahydrofuroic acid, tert-butyl ester (from Step A) was hydrolyzed according to the procedure of Reference Example 17, Step B to provide the title compound in 77% yield after chromatographic purification.

500 MHz $^1$H NMR ($CDCl_3$): δ 1.71 (s, 3H), 2.50(d, J=8.0 Hz, 1H), 2.93 (d, J=8.2 Hz, 1H), 4.18 (m, 2H), 7.25(br s, 1H).

REFERENCE EXAMPLE 22

3-(2-(2,6-Dichlorophenyl)-1,3-benzoxazol-5-yl) alanine, tert-Butyl Ester, Hydrochloride Salt Step A. Methyl 2-(2,6-Dichlorophenyl)-1,3-benzoxazole-5-carboxylate A solution of 2,6-dichlorobenzaldehyde (1.2 g, 6.8 mmol) and methyl 3-amino-4-hydroxybenzoate (1.0 g, 5.9 mmol) was refluxed in toluene (50 mL) overnight. The mixture was concentrated to dryness (rotary evaporator), and the residue was suspended in acetic acid (25 mL). The mixture was cooled by an ice-water bath, and was added-lead tetraacetate (3.2 g, 7.7 mmol). After stirring at room temperature for 4 h, the mixture was poured into ice water, and the product was extracted with ether (4×30 mL). The combined extracts were dried over $MgSO_4$, filtered and was concentrated. The residue was purified on a silica gel column eluting with 4:1 hexane/ethyl acetate to give the product (1.2 g, 60%).

Step B. 2-(2,6-Dichlorophenyl)-5-hydroxymethyl-1,3-benzoxazole

To a solution of the carboxylate of Step A (1.2 g, 3.9 mmol) in 30 mL of dry THF was added $LiAlH_4$ (0.34 g, 8.5 mmol) in one portion at −30 C After stirring for 3 h (bath temperature slowly rose to room temperature), the reaction mixture was carefully poured into brine and 2 M HCl. The product was extracted with ethyl acetate (3×30 mL). The combined extracts were dried over $MgSO_4$, filtered and concentrated to dryness to give the product, which was used immediately for the next step.

Step C. 5-Bromomethyl-2-(2,6-dichlorophenyl)-1,3-benzoxazole

To a suspension of N-bromosuccinimide (1.2 g, 6.7 mmol) in 10 mL of methylene chloride at −20 C was added dimethyl sulfide (0.50 mL, 6.7 mmol). After stirring at 0 C for 5 min, the reaction was cooled to −20 C and was added the alcohol obtained at Step B in 10 mL of methylene chloride. The bath was then removed, and the reaction was stirred at room temperature for 2 h, The reaction mixture was poured into water, and the product was extracted with ether (2×50 mL). The combined extracts were dried over $MgSO_4$, filtered and concentrated to dryness to give the crude bromide (1.3 g), which was used directly for the next step.

Step D. 3-(2-(2,6-Dichlorophenyl)-1,3-benzoxazol-5-yl)-N-diphenylmethylene)alanine, tert-Butyl Ester To a solution of the bromide of Step C (1.3 g, 3.7 mmol), t-butyl N-diphenylmethyleneglycinate (1.3 g, 4.4 mmol) and O(9)-allyl-N-9-anthracenylmethylcinchonidium bromide (0.24 g, 0.40 mmol) in 10 mL of methylene chloride at −78 C was added cesium hydroxide mono-hydrate (7.0 g, 41 mmol) (Corey, EJ; et al *J. Am.*

*Chem. Soc.* 1997, 119, 12414). The reaction was stirred for overnight at −50 C. The resulting mixture was poured into water, and the product was extracted with ether 3×50 mL). The combined extracts were dried over $MgSO_4$, filtered and concentrated. The residue was purified on a silica gel column eluting with 6:1 hexane/ethyl acetate to give the product (2.1 g, 95% from the ester over 3 steps).

$^1$H NMR (500 MHz, $CD_3OD$) δ 7.64–7.26 (14H, m), 7.22 (1H, dd, J=8.5, 1.5 Hz), 6.59 (1H, d, J=7.0 Hz), 4.22 (1H, dd, J=9.0, 4.5 Hz), 3.40 (1H, dd, J=13.5, 4.5 Hz), 3.26 (1H, dd, J=9.5, 4.5 Hz), 1.46 (9H, s).

Step E. 3-(2-(2,6-Dichlorophenyl)-1,3-benzoxazol-5-yl)alanine, tert-Butyl Ester, Hydrochloride Salt To a solution of the ester of Step D (2.1 g, 3.7 mmol) in 5 mL of THF was added acetic acid (5 mL) and water (5 mL) at room temperature. After stirring at room temperature for 2 h, the reaction mixture was poured into saturated sodium bicarbonate and saturated sodium carbonate (50 mL each), and the product was extracted with ethyl acetate (3×30 mL). The combined extracts were dried over $Na_2SO_4$, filtered and concentrated. The residue was purified on a silica gel column eluting with 4:1 hexane/ethyl acetate to 9:1:0.1:0.1 ethyl acetate/hexane/methanol/triethyl amine to give the product, which was converted to the corresponding hydrochloride salt by treatment with 1 M hydrogen chloride in ether (1.2 g, 75%).

$^1$H NMR (500 MHz, $CD_3OD$) δ 7.79 (1H, br s), 7.75 (1H, d, J=8.5 Hz), 7.64–7.60 (3H, m), 7.47 (1H, d, J=8.5 Hz), 4.28 (1H, t, J=8.0 Hz), 3.38 (1H, d, J=8.0 Hz), 1.41 (9H, s); LC-MS: calculated for $C_{20}H_{20}Cl_2N_2O_3$, 406; found m/e 407 (M+H$^+$).

REFERENCE EXAMPLE 23

2,5-Dimethyl-3-oxo-2-tetrahydrofuroic Acid

Step A. t-Butyl α-diazoacetoacetate

To a solution of t-butylacetate (11.9 g, 75 mmol) in 100 mL of anhydrous acetonitrile was added triethylamine (7.58 g). At 20° C., p-tolueneazide (prepared according to Org. Syn. Col. Vol. V. p 179) was added dropwise over 15 minutes. After being stirred at room temperature for 2.5 h, the volatiles were removed at 35° C. under reduced pressure and the residue was triturated with ether, washed with aqueous KOH (4.5 g KOH/50 mL water, then 0.75 g KOH/25 mL water), and water. The organic layer was dried over anhydrous sodium sulfate and the volatiles were removed until constant weight was obtained. This gave 13.7 g of a yellow liquid (quantitative) which was used in the next step without further purification, homogeneous by TLC (Rf=0.8 in 1/1 hexane/ethyl acetate). This procedure is based on Org. Syn. Col.Vol.V. p.179

NMR: 400 MHz $^1$H NMR ($CDCl_3$) δ 1.54 (s, 9H), 2.45 (s, 3H).

Step B. t-Butyl 2-diazo-3-oxo-5-hydroxyhexanoate

At −78° C., to a solution of t-butyl α-diazoacetoacetate (0.400 g, 2.17 mmol, obtained from Step A) in 50 mL of dichloromethane was added triethylamine dropwise, followed by dichlorophenylborane (2.64 mmol). The yellow reaction mixture was stirred at −78° C. for 3 h. Acetaldehyde (0.3 mL) was added dropwise and stirring was continued for 2 h at −78° C. After quenching the reaction at −78° C. with 30 mL of a 1/1 methanol/pH 7 buffer, the temperature was raised to 0° C. followed by addition of 7 mL of a 1/1 methanol/$H_2O_2$ (13% aq) solution. Half an hour later, phases were separated, the aqueous layer was reextracted with dichloromethane twice and the combined organic layers was washed with saturated aqueous sodium bicarbonate and 1M aq. NaOH. The aqueous layer was back extracted with dichloromethane. The organic layers were combined and dried over anhydrous sodium sulfate. The crude product obtained after filtration and removal of volatiles was purified via flash chromatography over silica gel, eluting with 40–5/1 mixtures of hexane/ethyl acetate. This provided 350 mg of the desired compound as a clear oil (71%), homogeneous by TLC (Rf=0.35, 4/1 hexane/ethyl acetate);

NMR: 400 MHz $^1$H NMR ($CDCl_3$) δ 1.25 (d, J=7.5 Hz, 3H), 1.54 (s, 9H), 2.88(dd, J=17.4, 9.2 Hz, 1H), 3.10 (dd, J=17.5, 2.1 Hz, 1H), 4.28 (m, 1H).

Step C. 5-Methyl-3-keto-2-tetrahydrofuroic Acid, t-Butyl Ester

Rhodium(II) acetate dimer (66 mg) was taken up in 7.5 mL of benzene and heated to 90° C. for 15 min. To this hot solution was added dropwise a solution of t-butyl 2-diazo-3-oxo-5-hydroxyhexanoate (from Step B) in 15 mL of dichloroethane. The reaction was completed ten minutes after completion of addition. After being cooled to room temperature, the reaction mixture was filtered over a pad of celite and the crude material obtained after removal of volatiles was passed through a miniBiotage 40 column and eluted using 10/1 hexane/ethyl acetate. This provided 503 mg (82.3%) of the desired material as a white glassy solid, homogenous by TLC (Rf=0.40, 4/1 hexane/ethyl acetate) but is a 3:1 mixture of the 2 pairs of diastereomers as shown by NMR;

NMR: 500 MHz $^1$H NMR ($CDCl_3$) δ 1.47, 1.53 (2d, J=6.0 Hz, 3H), 1.49, 1.50 (2s, 9H), 2.21, 2.28 (2dd, J=18, 10 Hz, 1H) 2.64 (dd, J=18, 6 Hz, 1H), 4.32, 4.48 (2s, 1H), 4.41, 4.75(m, 1H).

Step D. 2,5-Dimethyl-3-oxo-2-tetrahydrofuroic Acid, t-Butyl Ester

5-Methyl-3-keto-2-tetrahydrofuroic acid, t-butyl ester (790 mg, 3.95 mmol, from Step C) was dissovled in 1.2 mL of acetonitrile and placed in a sealed tube with a stirring bar. Anhydrous potassium carbonate (552 mg, 4 mmole) was added followed by iodomethane. The mixture was stirred at 90° C. for 24 h. After being cooled to room temperature and filtered through sintered glass, the residue was washed with copious amounts of acetonitrile and the volatiles were removed under reduced pressure. The crude product was chromatographed using a Biotage short column and gradient elution (100–20/1 hexane/ethyl acetate). This provided 694 mg (83%) of the desired product as an oil, homogenous by TLC (Rf=0.5 in 4/1 hexane/ethyl acetate). NMR shows this to be a 3:1 distereomeric pair mixture.

NMR: 400 MHz 1H NMR ($CDCl_3$) δ 1.47, 1.44 (2d, J=6.0 Hz, 3H), 1.41, 1.44(2s, 3H), 1.47(s, 9H), 2.16, 2.39 (2dd, J=18, 10 Hz, 1H), 2.63, 2.69 (2dd, J=18, 6 Hz, 1H), 4.41, 4.60 (m, 1H).

Step E. 2,5-Dimethyl-3-oxo-2-tetrahydrofuroic Acid

2-Methyl-3-oxo-2-tetrahydrofuroic acid, t-butyl ester (100 mg, 0.5 mmol) was treated with 1/1 trifluoroacetic acid/dichloromethane at 0° C. The reaction mixture was stirred at room temperature until all starting material had disappeared by TLC. The excess trifluoroacetic acid was removed via a stream of nitrogen and the residue was coevaporated with dichloromethane and purified via a silica gel SepPak plug. This 30 provided 49 mg of the desired product (68%), homogeneous by TLC (Rf=0.1 in 4/1 hexane/ethyl acetate).

NMR: 500 MHz $^1$H NMR (CDCl$_3$) δ 1.47, 1.51 (2d, J=6.2 Hz, 3H), 1.50, 1.54 (2s, 3H), 2.24, 2.41 (2dd, J=18, 9.8 Hz, 1H), 2.73 (dd, J=18, 6 Hz, 1H), 4.46, 4.60 (m, 1H) The following compounds were prepared by the procedure described in Reference Example 23 using the appropriate aldehyde: 2-benzyl-5-methyl-3-oxo-2-tetrahydrofuroic acid, 5-Methyl-3-oxo-2-phenyl-2-tetrahydrofuroic acid.

REFERENCE EXAMPLE 24

2,5-Dimethyl-3-hydroxy-2-tetrahydrofuroic Acid

Step A. 2,5-Dimethyl-3-hydroxy-2-tetrahydrofuroic Acid, t-Butyl Ester 2,5-Dimethyl-3-oxo-2-tetrahydrofuroic acid, t-butyl ester (50 mg, 0.35 mmol, from Reference Example 23, Step D) was dissolved in anhydrous methanol (4 mL) and cooled to 0° C. Sodium borohydride (0.39 mmol, 15 mg) was added all at once and the reaction mixture was stirred for another 20 minutes at 0° C. After acetone (0.2 mL) was added to quench the reaction mixture, saturated aqueous ammonium chloride (8 mL) was added and the reaction mixture was stirred at for 10 minutes 0° C. followed by at room temperature for 30 minutes. Methylene chloride was added to extract the organic material. The aqueous phase was re-extracted twice with dichloromethane. The organic layers were combined and washed with brine and dried over anhydrous sodium sulfate. This provided 53 mg of the title compound (70%), homogeneous by TLC (Rf=0.15 in 4/1 hexane/ethyl acetate).

NMR: 500 MHz $^1$H NMR (CDCl$_3$) δ 1.28, 1.31, 1.34 (3d, J=7 Hz, 3H), 1.40, 1.41, 1.49 (s, 3H), 1.46, 1.50 (s, 9H), 1.55–1.80 (m, 1H), 2.30–2.43 (m, 1H), 3.0 (m, 1H), 4.21, 4.42 (2m, 1H), 4.39, 4.43 (2m, 1H).

Step B. 2,5-Dimethyl-3-hydroxy-2-tetrahydrofuroic Acid

The title compound was prepared according to the procedure of Reference Example 23, Step E. After chromatographic separation, 2 fractions were obtained. One of these (Diastereomer 1) is a single pair of compounds, the other one (Diastereomer 2) contains 2 pairs of diastereomers; each homogeneous by TLC (1/1 hexane/ethyl acetate).

Diastereomer Pair 1: NMR: 500 MHz $^1$H NMR (CD$_3$OD) δ 1.27 (m, 1H), 1.34 (3d, J=7.2 Hz, 3H), 1.38 (s, 3H), 1.71 (m, 1H), 2.39 (m, 1H), 4.17 (m, 1H), 4.26(m, 1H). Diastereomer Pairs 2: NMR: 500 MHz $^1$H NMR (CD$_3$OD) δ 1.28, 1.34 (3d, J=6.2 Hz, 3H), 1.38 (s, 3H), 1.52, 1.70 (m, 1H), 2.35, 2.42 (m, 1H), 4.10–4.37 (m, 1H), 4.47(m, 1H),

REFERENCE EXAMPLE 25

2,5-Dimethyl-3-methoxycarbonylmethyl-2-tetrahydrofuroic Acid

Step A. 2,5-Dimethyl-3-methoxycarbonylmethylene-2-tetrahydrofuroic Acid, t-Butyl Ester 2,5-Dimethyl-3-oxo-2-tetrahydrofuroic acid, t-butyl ester (64 mg, from Reference Example 23, Step D) was dissolved in anhydrous methanol (1 mL) and cooled to −78° C. Potassium bis(trimethylsilyl)amide 0.66 mL) was added dropwise over 10 minutes. After being stirred at 78° C. for 15 minutes, trimethyl phosphonoacetate (65 mg, dissolved in 1.5 mL tetrahydrofuran) was added dropwise over 25 minutes. Upon completion of addition, the cold bath was removed and the mixture was allowed to stir at room temperature for 3 h when TLC (4/1 hexane/ethyl acetate) showed formation of a new spot. At 0° C., the reaction was quenched by addition of 1.5 mL of saturated aqueous ammonium chloride and the product was extracted with ethyl acetate twice, washed with saturated sodium chloride and dried over anhydrous magnesium sulfate. The crude product obtained after filtration and removal of volatiles was flash chromatographed over silica get, using gradient elution (50–10/1 hexane/ethyl acetate) to give 31 mg of the desired compound, homogeneous by TLC (Rf=0.5 in 4/1 hexane/ethyl acetate). The NMR showed that all the diastereomers are present in this sample.

NMR: 500 MHz $^1$H NMR (CDCl$_3$) δ 1.31, 1.39 (2d, J=7 Hz, 3H), 1.45, 1.47 (2s, 9H), 1.51, 1.56 (2s, 3H), 2.35–2.70 (m, 1H), 2.80–3.50(m, 1H), 3.68, 3.74(2s, 3H), 4.25(m, 1H), 5.9 (m, 1H).

Step B. 2,5-Dimethyl-3-methoxycarbonylmethyl-2-tetrahydrofuroic Acid, t-Butyl Ester 2,5-Dimethyl-3-methoxycarbonylmethylene-2-tetrahydrofuroic acid, t-butyl ester (28 mg, obtained from Step A) was dissolved in 0.25 mL of ethyl acetate and 0.25 mL of methanol. This mixture was hydrogenated under a balloon of hydrogen at room temperature for 1.25 h. The reaction mixture was filtered over a pad of celite, and the crude product obtained after removal of volatiles was purified via a silica gel SepPak, providing 21 mg of the desired compound cleanly (75% yield), homogeneous by TLC (Rf= 0.2 in 10/1 hexane/ethyl acetate)

NMR: 500 MHz $^1$H NMR (CDCl$_3$) δ 1.36(2d, J=7.2 Hz, 3H), 1.44 (s, 3H), 1.42 (m, 1H), 1.49 (s, 9H), 2.35–2.52 (m, 1H), 2.48–2.60(m, 1H), 3.70(s, 3H), 4.25(m, 1H).

Step C. 2.5-Dimethyl-3-methoxycarbonylmethyl-2-tetrahydrofuroic Acid

The title compound was obtained from 2,5-Dimethyl-3-methoxycarbonylmethyl-2-tetrahydrofuroic acid, t-butyl ester (Step B) according to the procedure of Example 122 Step B. The crude product was purified by a silica gel SepPak, homogeneous by TLC (Rf=0.2 in 1/1 hexane/ethyl acetate);

NMR: 500 MHz $^1$H NMR (CDCl$_3$) δ 1.33(m, 1H), 1.39 (d, J=7.3 Hz, 3H), 1.53(s, 3H), 2.28 (m, 1H), 2.35(m, 1H), 2.65 (m, 1H), 2.75 (m, 1H), 3.70(s, 3H), 4.28(m, 1H).

REFERENCE EXAMPLE 26

(L)-4-(2',6'-(Dimethoxyphenyl)phenylalanine, tert-Butyl Ester Hydrochloride

Step A. N-(BOC)-4-[(Trifluoromethylsulfonyl)oxy]-(L)-phenylalanine, tert-Butyl Ester.

To a solution of N-(BOC)-(L)-tyrosine, tert-butyl ester (18.5 g, 55 mmol) in 150 mL of dry methylene chloride was added pyridine (17.4 g, 220 mmol) followed at 0° C. by the dropwise addition of neat triflic anhydride (18.6 g , 66 mmol). The reaction mixture was stirred at 0° C. and monitored by TLC. After 4 hours, the mixture was diluted with 200 mL of methylene chloride and was washed successively with 1N HCl (3×100 mL), saturated sodium bicarbonate (2×100 mL) and brine (1×50 mL). The solution was dried over anhydrous MgSO$_4$, filtered and concentrated in vacuo to give N-(BOC)4-[(trifluoromethylsulfonyl)oxy]-(L)-phenylalanine, tert-butyl ester as an oil which was used without further purification.

Step B. N-(BOC)-(L)-4-(2',6'-(Dimethoxyphenyl) phenylalanine, tert-Butyl Ester, Hydrochloride.

N-(BOC)4-[(trifluoromethylsulfonyl)oxy]-(L)-phenylalanine, tert-butyl ester (Step A) was dissolved in a mixture of 125 mL of toluene and 61 mL of ethanol. To this solution was added 2,6-dimethoxyboronic acid (11.3 g, 62 mmol) and palladium tetrakistriphenylphosphine (2.5 g). The solution was treated with of potassium carbonate (18.3 g, 133 mmol) dissolved in 30 mL of water. The mixture was heated to reflux over 4 hours, cooled to room temperature, and then diluted with 200 mL of ethyl acetate. The solution was washed with water (3×75 mL) and brine (1×75 mL) and was dried over anhydrous MgSO$_4$. The mixture was filtered and concentrated in vacuo and the residue was purified by flash column chromatography on silica gel eluted with a gradient of 5–20% EtOAc in hexanes to provide 14.7 g of N-(BOC)-(L)-4-(2',6'-(dimethoxyphenyl)phenylalanine, tert-butyl ester, hydrochloride as a white solid.

Step C. (L)-4-(2',6'-(Dimethoxyphenyl)phenylalanine, tert-Butyl Ester Hydrochloride.

N-(BOC)-(L)-4-(2',6'-(Dimethoxyphenyl)phenylalanine, tert-butyl ester, hydrochloride (Step B) was dissolved in 350 mL of tert-butyl acetate at 0° C. and was treated with 8.3 mL of concentrated sulfuric acid. The cold bath was removed and after one hour TLC indicated only starting material was present. The reaction mixture was cooled in an ice bath once more and treated with 3.4 mL of concentrated sulfuric acid. The reaction was monitored by TLC. After consumption of the starting material the reaction mixture was diluted with 300 mL of ethyl acetate and was washed with 3×100 mL of 1N NaOH followed by brine (1×100 mL). The solution was dried over anhydrous MgSO$_4$. Filtered and was concentrated in vacuo to provide 8.9 g of (L)-4-(2',6'-(dimethoxyphenyl) phenylalanine, tert-butyl ester hydrochloride.

500 MHz 1H NMR (CD$_3$OD): δ 1.45 (s, 9H), 3.20 (d, 2H); 3.69 (s, 6H); 4.20 (t, 1H); 6.72 (d, 2H), 7.15 (m, 5H).

REFERENCE EXAMPLE 27

2-(4-methoxyphenyl)-2-tetrahydrofuroic Acid

Step A. 5-Chloro-2-(4-methoxyphenyl)-heptanoic Acid, Methyl Ester.

To a solution of 4-methoxymandelic acid methyl ester (1.1 g, 5.7 mmol) in 10 ml of THF was added lithium hexamethyldisilazane (12.5 ml, 1M in THF). The reaction was stirred at −78° C. for 1.5 h, allowed to briefly warm to 0° C., then cooled to −78° C. 1-Bromo-3-chloropropane (1 g, 6.3 mmol) in 1 ml of THF was added to the solution and it was allowed to warm to room temperature. After stirring for 30 minutes, the reaction was quenched with water (25 ml) and the product extracted into ethyl acetate (50 ml). The organic layer was dried with magnesium sulfate, concentrated in vacuo then chromatographed over silica gel eluting with hexane/ethyl acetate (3:1) to 0.26 g of the product as a colorless oil.

500 MHz $^1$H NMR (CDCl$_3$): 7.49 (d, J=8.9 Hz, 2H), 6.88 (d, J=9 Hz, 2H), 3.80 (s, 3H), 3.79 (s, 3H), 3.54 (m, 2H), 2.22 (m, 2H), 1.8 (M, 2H).

Step B. 2-(4-Methoxyphenyl)-2-tetrahydrofuroic Acid, Methyl Ester

To a solution of 5-chloro-2-(4-methoxyphenyl)-heptanoic acid methyl ester (0.26 g, 0.96 mmol) in 5 ml of DMF at 0° C. was added sodium hydride (0.6 g, 1.4 mmol). The reaction was stirred for 1 h at this temperature then quenched with 10 ml of water. The product was extracted into ethyl acetate (3×15 ml), washed with brine (20 ml), dried with magnesium sulfate and concentrated in vacuo to give a yellow oil. Silica gel chromatography eluting with hexane/ ethyl acetate (4:1) gave 0.063 g of the title compound as a colorless oil.

500 MHz 1H NMR (CDCl$_3$): 7.44 (d, J=8.9 Hz, 2H), 6.87 (d, J=8.6 Hz, 2H), 4.05 (m, 2H), 3.80 (s, 3H), 3.70 (s, 3H), 2.78 (m, 1H), 2.18 (m, 1H), 1.95 (m, 2H).

Step C. 2-(4-methoxyphenyl)-2-tetrahydrofuroic Acid

To a solution of 2-(4-methoxyphenyl)-2-tetrahydrofuran Methyl Ester in 1 ml of methanol was added 5 drops of a 1N NaOH solution. After three hours, the reaction was quenched with 1 ml of 1N HCl and the product extracted into ethyl acetate (4×1 ml). The organics were dried with magnesium sulfate and concentrated to give the title compound as a yellow solid (0.565 g).

REFERENCE EXAMPLE 28

2-(3,5-Dimethoxyphenyl)-2-tetrahydrofuroic Acid 2-(3,5-Dimethoxyphenyl)-2-tetrahydrofuroic acid was prepared according to the procedures described in Reference Example 27 substituting 3,5-dimethoxymandelic acid, methyl ester for 4-methoxymandelic acid, methyl ester in Step A.

REFERENCE EXAMPLE 29

2-(2-benzoxazole)-2-tetrahydrofuroic Acid, Methyl Ester

Step A. N-2-hydroxyphenyl-2-tetrahydrofuroic Acetamide

To a solution of 2-tetrahydrofuroic acid (2.2 g, 19.2 mmol) and 2-aminophenol (1.0 g, 9.2 mmol) in 25 ml of methylene chloride was added PyBop (10.5 g, 22.9 mmol) and DIPEA (4.1 ml, 22.9 mmol). The reaction was stirred at room temperature for 20 h then diluted with ethyl acetate (50 ml). The organic layer was washed with water (50 ml), brine (50 ml) and dried with magnesium sulfate, concentrated in vacuo then chromatographed over silica gel eluting with hexane/ethyl acetate (6:4) to give 3.1 g of an oil. This oil was dissolved in 25 ml of toluene, treated with toluene sulfonic acid (1.9 g, 10.0 mmol) and heated to 75° C. for 1 hr. The reaction was diluted with ethyl acetate (50 ml), dried with magnesium sulfate and concentrated to give a white solid 1.0 g.

500 MHz $^1$H NMR (CDCl$_3$): 9.18 (s, 1H), 8.7 (s, 1H), 7.12 (m, 1H), 7.04 (m, 2H), 6.86 (m, 1H), 4.54 (m, 1H), 4.08 (m, 1H), 3.98 (m, 1H), 2.39, (m, 1H), 2.18 (m, 1H), 1.97 (m, 2H).

Step B. 2-(2-benzoxazole)-2-tetrahydrofuran

To a solution of N-2-hydroxyphenyl-2-tetrahydrofuroic acetamide (1.0 g, 5.0 mmol) and triphenylphosphine (1.95 g, 7.5 mmol) in 10 ml of THF was added DEAD (01.2 ml, 7.5 mmol). The reaction was stirred for 18 h at room temperature, diluted with ethyl acetate (50 ml), washed with water (50 ml), brine (50 ml), dried with magnesium sulfate, concentrated then chromatographed over silica gel eluting with hexane/ethyl acetate (2:1) to give 0.3 1 g of a colorless oil. 500 MHz $^1$H NMR (CDCl$_3$): 7.7 (m, 1H), 7.5 (m, 1H), 7.3 (m, 2H), 5.2 (m, 1H), 4.1 (m, 1H), 4.0 (m, 1H), 2.4 (m, 2H), 2.15 (m, 1H), 2.05 (m, 1H).

Step C. 2-benzoxazole-2-tetrahydrofuroic Acid, Methyl Ester

To a solution of 2-benzoxazole-2-tetrahydrofuran (0.23 g, 1.19 mmol) in 2 ml of THF at −78° C. was added methyl chloroformate (0.14 ml, 1.78 mmol) followed by LiHMDS (1.8 ml, 1M in THF). The reaction was stirred for 1 h at −78° C. then quenched with 10 ml of water. The product was extracted into ethyl acetate (20 ml), washed with brine (10 ml), dried with magnesium sulfate, concentrated then chromatographed over silica gel eluting with hexane/ethyl acetate (3:1) to give 0.19 g of a colorless oil. 500 MHz $^1$H NMR (CDCl$_3$): 7.75 (m, 1H), 7.54 (m, 1H), 7.36 (m, 2H), 4.22 (m, 1H), 4.25 (m, 1H), 3.8 (s, 3H), 3.08 (m, 1H), 2.62 (m, 1H), 2.16 (m, 2H).

REFERENCE EXAMPLE 30

2-(4-methyl-2-thiazole)-2-tetrahydrofuroic Acid

Step A. 2-[(2-oxo-1-propyl)aminocarbonyl)]-2-tetrahydrofuroic Acid, tert-Butyl Ester.

To a solution of 2-carboxy-tetrahydrofuroic acid, tert-butyl ester (0.15 g, 0.069 mmol) and 1-amino-2-propanol (0.57 g, 0.076 mmol) was added PyBop (0.40 g, 0.076 mmol) and DIPEA (0.20 ml, 1.04 mmol). The reaction was stirred at room temperature for 17 h, concentrated in vacuo then chromatographed over silica gel eluting with hexane/ethyl acetate (3:1) to give 0.22 g of an oil. 0.24 g of this oil was oxidized to the corresponding ketone by treatment with cat. TPAP in the presence of excess NMO in methylene chloride for 1 hr. Filtration through silica gel eluted with hexane/ethyl acetate (1:1) resulted in 0.19 g of the title compound as a colorless oil. 500 MHz $^1$H NMR (CDCl$_3$): 4.0–4.25 (m, 4H), 2.6 (m, 1H), 2.3 (m, 1H), 2.21 (s, 3H), 2.05 (m, 1H), 1.95 (m, 1H), 1.45 (s, 9H).

Step B. 2-(4-Methyl-2-thiazole)-2-tetrahydrofuroic Acid.

To a solution of (0.21 g, 0.079 mmol) in 0.25 ml toluene was added Lawesson's Reagent (0.38 g, 0.095 mmol) and the reaction was heated to 100° C. for 1 h. The reaction was concentrated then chromatographed over silica gel eluting with hexane/ethyl acetate (5:1) to give and oil. This oil was treated with trifluoroacetic acid in methylene chloride followed by silica gel chromatography eluting with methylene chloride/methanol/acetic acid (97:3:0.5) to give an oil (0.005 g). 500 MHz $^1$H NMR (CDCl$_3$): 7.85 (s, 1H), 4.1–4.2 (m, 2H), 2.65 (m, 1H), 2.45 (m, 1H), 2.2 (m, 1H), 2.1 (s, 3H), 2.0 (m, 1H).

REFERENCE EXAMPLE 31

(L)-4-((2',6'-dichloro)benzamido)-phenylalanine, Methyl Ester Hydrochloride

Step A. N-(BOC)-(L)-4-((2',6'-dichloro)benzamido)-phenylalanine, Methyl Ester.

N$_{(\alpha)}$-(BOC)-(L)-4-(FMOC-amino)-phenylalanine, methyl ester (9.62 g, 18.6 mmol) was dissolved in 15 mL of DMF and treated with diethylamine(11.6 mL, 112 mmol). The reaction mixture was stirred at room temperature for two hours, then concentrated in vacuo to give an viscous oil. This residue was dissolved in CH$_2$Cl$_2$ (50 mL) then treated with diisopropylethylamine (5.16 mL, 27.9 mmol) and 2,6-dichlorobenzoyl chloride (2.93 mL, 20.4 mmol). The reaction mixture was stirred overnight at room temperature and then quenched with H$_2$O (40 mL). The layers were separated and the aqueous layer was extracted with CH$_2$Cl$_2$ (2×40 mL). The combined organic layers were combined and washed with brine (1×200 mL) then dried over anhydrous MgSO$_4$. The mixture was filtered and concentrated in vacuo, then the residue was purified by flash column chromatography eluted with 50% EtOAc in hexane to give N-(BOC)-(L)-4-((2',6'-dichloro)benzamido)-phenylalanine, methyl ester (7.3 g).

500 MHz $^1$H NMR (CDCl$_3$): 1.44 (s, 9H); 3.12 (m, 2H); 3.75 (s, 3H); 4.61 (m, 1H); 5.00 (d, 1H); 7.15 (d, 2H); 7.32 (m, 3H); 7.59 (d, 2H).

Step B (L)-4-((2',6'-dichloro)benzamido)-phenylalanine, Methyl Ester Hydrochloride.

N-(BOC)-(L)-4-((2',6'-dichloro)benzamido)-phenylalanine, methyl ester (2.50 g, 5.35 mmol) was dissolved in dioxane (5 mL) and treated with HCl in EtOAc (18.4 mL of 2.9 N). The mixture was stirred overnight at room temperature, then concentrated in vacuo to give a quantitative yield of (L)-4-((2',6'-dichloro)-benzamido) phenylalanine, methyl ester hydrochloride.

500 MHz $^1$H NMR (CD$_3$OD): 3.17 (m, 1H); 3.28 (m, 1H); 3.84 (s, 3H); 4.33 (m, 1H); 7.28 (d, 2H); 7.46 (m, 3H); 7.68 (d, 2H).

REFERENCE EXAMPLE 32

4-(4-(tert-Butoxycarbonyl)-piperazinecarbonyl)-phenylalanine, Methyl Ester

Step A. N-(Fmoc)-(L)-4-tert-Butoxycarbonyl-phenylalanine, Methyl Ester

To a solution of N-(9-fluorenylmethoxycarbonyl)-(L)-4-tert-butoxycarbonyl-phenylalanine (4.6 g, 9.4 mmol) in methylene chloride and methanol (50 mL each) at 0 C was added TMSCHN$_2$ until a yellow color persisted (2 M, 15 mL, 14 mmol). After stirring at room temperature for 30 min, the mixture was concentrated to give the title compound (5.0 g) and was used without further purification.

Step B. N-(Fmoc)-(L)-4-Carboxy-phenylalanine, α-Methyl Ester

To a solution of N-(Fmoc)-(L)-4-tert-butoxycarbonyl-phenylalanine, α-methyl ester (5.0 g, 10 mmol) in 100 mL of methylene chloride was added trifluoroacetic acid (38 mL, 0.50 mol) mL at 0° C. After stirring at room temperature overnight, the mixture was concentrated to give the title compound (4.4 g) and was used without further purification.

LC-MS: calculated for C$_{26}$H$_{23}$NO$_6$, 445; found m/e 446 (M+H$^+$).

Step C. N-(Fmoc)-(L)4-((4-N-tert-Butoxycarbonyl) piperazinyl-1-carbonyl)phenylalanine, α-Methyl Ester To a solution of N-(Fmoc)-(L)-4-carboxy-phenylalanine, α-methyl ester (3.4 g, 7.6 mmol) and N-tert-butoxycarbonylpiperazine (1.4 g, 7.6 mmol) in 50 mL of methylene chloride at 0° C. was added diisopropylethyl amine (2.7 mL, 15 mmol) and tris(pyrrolindinyl) phosphonium hexafluorophosphate (PyBOP, 4.2 mg, 8.0 mmol). After stirring at room temperature for 2 hr, TLC indicated complete consumption of the starting material. The reaction mixture was then concentrated, and the residue was purified on a silica gel column eluting with 1:4 acetone/hexane to give the title compound (4.0 g, 84%). LC-MS: calculated for C$_{35}$H$_{39}$N$_3$O$_7$, 613; found m/e 614 (M+H$^+$).

Step D. (L)-4-((4-N-tert-Butoxycarbonyl)piperazinyl-1-carbonyl)phenylalanine, α-Methyl Ester To a solution of N-(Fmoc)-(L)4-((4-N-tert-butoxycarbonyl) piperazinyl-1-carbonyl)-phenylalanine, α-methyl ester (4.0 g, 6.5 mmol) in methylene chloride (40 mL) was added diethyl amine (13 mL, 0.13 mol). After stirring at room temperature overnight, the reaction mixture was concentrated, and the residue was purified on a silica gel column eluting with methylene chloride to 1:20 methanol/methylene chloride to give the title compound (2.2 g, 89%). LC-MS: calculated for C$_{20}$H$_{29}$N$_3$O$_5$, 391; found m/e 392 (M+H$^+$).

REFERENCE EXAMPLE 33

3,5-Dimethoxy-4-((tert-butyldiphenylsilyl) oxymethyl)phenylboronic Acid

Step A. 3,5-Dimethoxybenzyl(tert-butyldiphenyl)silyly Ether

To 4.0 g (23.7 mmol) of 3,5-dimethoxybenzyl alcohol in 50 mL of DMF, 6.2 mL of tert-butyldiphenylsilyl chloride and 3.2 g (47.5 mmol) of imidazole were added. The reaction mixture was stirred overnight at 40° C. The mixture was concentrated in vacuo to give a residue. The residue was purified by flash column chromatography on silica gel eluted with hexanes and 20% hexanes/ethyl acetate to afford a quantitative yield of the desired product. MS m/e=407.28 (M+H$^+$).

Step B. 3,5-Dimethoxy-4-((tert-butyldiphenylsilyl) oxymethyl)phenylboronic Acid

To 9.3 g (22.8 mmol) of 3,5-dimethoxybenzyl(tert-butyldiphenyl)silyl ether in 25 mL of THF cooled to −78° C., 16 mL of butyllithium (2.5 M in hexanes) was added. The mixture was stirred at −78° C. for an hour, then warmed to room temperature and stirred for an hour. This mixture was cooled again to −78° C. and 6.5 mL (57.1 mmol) of trimethyl borate was added. The mixture was warmed to room temperature and stirred for four hours. The mixture was quenched with 10 mL of water and continued to stir for a half hour. This mixture was acidified with acetic acid to pH 4. The mixture was extracted with ethyl acetate (3×). The organic layer was dried over anhydrous $MgSO_4$. The mixture was filtered and concentrated in vacuo and the residue was purified by flash chromatography on silica gel eluted with 25% hexanes/ethyl acetate to give 3.7 g of the desired product. MS m/e=;451.41 $(M+H^+)$.

REFERENCE EXAMPLE 34

N-(2(R)-Methyl-2-tetrahydrofuroyl)-(L)-4-(2,6-dimethoxy-4-(bromomethyl)phenyl)phenylalanine, Methyl Ester Step A. N-(2(R)-Methyl-2-tetrahydrofuroyl)-(L)-(4-(2,6-dimethoxy-4-tert-butyldiphenylsilyloxymethyl)phenyl) phenylalanine, Methyl Ester N-(2(R)-Methyl-2-tetrahydrofuroyl)-(L)-4-iodophenylalanine, methyl ester (from Example 111, Step B) was coupled with 3,5-dimethoxy-4-((tert-butyldiphenylsilyloxymethyl)phenylboronic acid (from Reference Example 33, Step B) mediated by tetrakis-triphenylphosphine palladium(0) as described in Reference Example 2, Step B to provide 2.01 g of the desired product after flash column chromatography on silica gel eluted with 50% hexanes/ethyl acetate. MS m/e=696.36 $(M+H^+)$.

Step B. N-(2(R)-Methyl-2-tetrahydrofuroyl)-(L)-(4-(2,6-dimethoxy-4-hydroxymethyl)phenyl)phenylalanine, Methyl Ester To 1.98 g (2.84 mmol) of N-(2(R)-methyl-2-tetrahydrofuroyl)-(L)-4-(2,6-dimethoxy-4-(tert-butyldiphenylsilyloxymethyl)phenyl)phenylalanine, methyl ester in 15 mL of THF cooled to 0° C., 3.12 mL (3.12 mmol) of tetrabutylammonium fluoride (1.0 M in THF) was added. The mixture was stirred at 0° C. for two hours. The mixture was concentrated in vacuo and the residue was purified by flash column chromatography on silica gel eluted with 50% hexanes/ethyl acetate to give 1.27 g of the desired product. MS m/e=458.3² $(M+H^+)$.

Step C. N-(2(R-Methyl-2-tetrahydrofuroyl)-(L)-(4-(2,6-dimethoxy-4-bromomethyl)phenyl)phenylalanine, Methyl Ester To 2.52 g (5.97 mmol) of dibromotriphenylphosphine dissolved in 15 mL of $CH_2Cl_2$, a solution of 911 mg of N-(2(R)-methyl-2-tetrahydrofuroyl)-(L)-(4-(2,6-dimethoxy-4-hydroxymethyl)phenyl)phenylalanine, methyl ester was added. The reaction mixture was stirred overnight. The mixture was concentrated in vacuo and the residue was purified by flash column chromatography on silica gel eluted with 2:1 hexanes/ethyl acetate to give 692 mg of the desired product. MS m/e=522.1 $(M+H^+)$.

EXAMPLE 1

General Procedure for the Solid-phase Synthesis of Compounds of Formula 1

Described below is the method used for preparing N-FMOC-(L)-4-(2'-cyanophenyl)phenylalanine resin and its subsequent use in the solid phase preparation of compounds of the present invention. The procedure may be applied to other amino acids such as those described in Reference Examples 2 and 3 to provide the appropriate resins. Some commercially available N-FMOC-amino acid resins were also utilized. All reactions were carried out in polyethylene syringes fitted with frits (Applied Separations) and capped with adaptors (Varian) and teflon stopcocks (Jones Chromatography). Agitation of the vessels was performed by rotation on a tube rotator.

Step A. Loading of N-FMOC-(L)-4-(2'-Cyanophenyl) phenyl onto Resin.

5.0 g (4.75 mmol based on 0.95 mmol/g capacity) of Wang resin (Bachem) was suspended in 60 ml of 50% $THF/CH_2Cl_2$ (sufficient to ensure semi-fluid state) and treated with 4.64 g (9.5 mmol) N-FMOC-(L)-4-(2'-cyanophenyl)phenylalanine, 1.81 g (9.5 mmol) of EDC and 0.63 g (4.7 mmol) of DMAP. The mixture was agitated for 2.5 hours and filtered through the integral frit. The resin was washed twice with 50% $THF/CH_2Cl_2$ (50 ml) and the reaction was repeated as above. The mixture was filtered though the integral frit and washed: $THF/CH_2Cl_2$ (3×50 ml), $CH_2Cl_2$ (2×50 ml), MeOH (2×50 ml), $CH_2Cl_2$ (50 ml), MeOH (50 ml), $CH_2Cl_2$ (2×50 ml) and ether (2×50 ml). The resin was dried in vacuo to give 7.20 g of the desired product.

Loading was evaluated by treating 50 mg of the resin in a 2 ml polyethylene syringe with 95% $TFA/H_2O$ (3×2 ml for 10 minutes). The combined filtrates were concentrated in vacuo and the residue was weighed and analysed by HPLC, NMR. The loading of the resin from Step A was 0.78 mmol/g and the recovered amino acid was >90% pure by HPLC (210 nM).

Step B. Deprotection of the FMOC Group.

30 mg (0.028 mmol based on 0.95 mmol/g loading) of the resin from Step A was placed in a 2 ml polyethylene frit fitted syringe. The syringe outlet was capped by a teflon stopcock. The resin was treated with 2 ml (3×10 min) of 20% piperidine in DMF. Following the final treatment the resin was washed with DMF (3×2 ml).

Step C. Coupling to Carboxylic Acids.

The resin from Step B (in the same reaction vessel) was treated with a solution made up in 1.5 ml of DMF of: 0.112 mmol of the carboxylic acid, 0.112 mmol of HBTU, 0.112 mmol of $HOBt.H_2O$ and 0.14 mmol of diisopropylethylamine. The vessel was capped with an adaptor and teflon stopcock and rotated overnight. The reaction mixture was filtered and the resin was washed with DMF (3×2 ml) followed by $CH_2Cl_2$ (2×2 ml). A 1 mg aliquot of the resin was submitted to the Kaiser test to confirm that all primary amine had been acylated. If the conversion was complete the resin was washed: DMF (3×2 ml), $CH_2Cl_2$ (2×2 ml), MeOH (2×2 ml), $CH_2Cl_2$ (2 ml), MeOH (2 ml), $CH_2Cl_2$ (3×2 ml). If the resin was not completely acylated the reaction was repeated.

Step D. Cleavage of the Product from the Resin.

The resin (in the original vessel) was treated with 95% $TFA/H_2O$ (3×1.5 ml) and the resulting filtrates were collected in a previously tared 13 mm×100 mm test tube. The filtrate was concentrated in vacuo in a rotory concentrator. The residue was dissolved in approximately 3 ml of 30% $CH_3CN/H_2O$ and aliquots were removed for HPLC and MS analysis. The solution was then lyophilized to provide the desired product. Criteria for assay included >80 % purity by HPLC and structure was confirmed by mass spectrum.

The following compounds were prepared by the procedures described above using the appropriate carboxylic acid and amino acid derivatives:

| Ex. No. | Name | MS* |
|---|---|---|
| 1 | N-((S)-5-oxo-2-tetrahydrofuroyl)-(L)-4-(2'-cyano-phenyl)phenylalanine | 396 |
| 2 | N-((S)-5-oxo-2-tetrahydrofuroyl)-(L)-4-(2'-methoxy-phenyl)phenylalanine | 384 |
| 3 | N-(3-tetrahydrofuroyl)-(L)-4-(2'-cyanophenyl)phenyl-alanine | 365 |

-continued

| Ex. No. | Name | MS* |
|---|---|---|
| 4 | N-(3-tetrahydrofuroyl)-(L)-4-(2'-methoxyphenyl)-phenylalanine | 370 |
| 5 | N-(2,2-dimethyl-5-oxo-3-tetrahydrofuroyl)-(L)-4-(2'-cyanophenyl)phenylalanine | 424 |
| 6 | N-(2,2-dimethyl-5-oxo-3-tetrahydrofuroyl)-(L)-4-(2'-methoxyphenyl)phenylalanine | 429 |
| 7 | N-(2,2-dimethyl-5-oxo-3-tetrahydrofuroyl)-(L)-4-(1-pyrrolidino-carbonyloxy)phenylalanine | 419 |
| 8 | N-(1,1-dioxo-5-methyl-tetrahydro-2-thienoyl)-(L)-4-(2'-cyanophenyl)phenylalanine | 427 |
| 9 | N-(1-methyl-3-oxo-isobenzofuroyl)-(L)-4-(2"-methoxyphenyl)phenylalanine | 463 |
| 10 | N-(dihydro-2-benzofuroyl)-(L)-4-(2"-methoxyphenyl)-phenylalanine | 418 |
| 11 | N-(2,2-dimethyl-5-oxo-3-tetrahydrofuroyl)-3(R,S)-amino-3-phenyl-propionic acid | 306 |
| 12 | N-(1,1-dioxo-5(R,S)-methyl-2(R,S)-tetrahydrothienoyl)-(L)-4-(2'-methoxyphenyl)phenylalanine | |
| 13 | N-(2-benzyl-2-tetrahydrofuroyl)-(L)-4-(2'-methoxy-phenyl)phenylalanine (Isomer A) | 460; 477 |
| 14 | N-(2-benzyl-2-tetrahydrofuroyl)-(L)-4-(2'-methoxy-phenyl)phenylalanine (Isomer B) | 460; 477 |
| 15 | N-(2-phenylethyl)-2-tetrahydrofuroyl)-(L)-4-(2'-methoxyphenyl)phenylalanine (Isomer A) | 474; 491 |
| 16 | N-(2-phenylethyl)-2-tetrahydrofuroyl)-(L)-4-(2'-methoxyphenyl)phenylalanine (Isomer B) | 474; 491 |
| 17 | N-(2-tetrahydropyranoyl)-(L)-4-(2'-methoxyphenyl)-phenylalanine (Isomer A) | 384; 401 |
| 18 | N-(2-tetrahydropyranoyl)-(L)-4-(2'-methoxyphenyl)-phenylalanine (Isomer B) | 384; 401 |
| 19 | N-(2-methyl-2-tetrahydropyranoyl)-(L)-4-(2'-methoxy-phenyl)phenylalanine (Isomer A) | 398; 415 |
| 20 | N-(2-methyl-2-tetrahydropyranoyl)-(L)-4-(2'-methoxy-phenyl)phenylalanine (Isomer B) | 398; 415 |
| 21 | N-(2-benzyl-2-tetrahydropyranoyl)-(L)-4-(2'-methoxy-phenyl)phenylalanine (Isomer A) | 475; 491 |
| 22 | N-(2-benzyl-2-tetrahydropyranoyl)-(L)-4-(2'-methoxy-phenyl)phenylalanine (Isomer B) | 475; 491 |
| 23 | N-(2-(2-phenylethyl)-2-tetrahydropyranoyl)-(L)-4-(2'-methoxyphenyl)phenylalanine (Isomer A) | 474; 491 |
| 24 | N-(2-(2-phenylethyl)-2-tetrahydropyranoyl)-(L)-4-(2'-methoxyphenyl)phenylalanine (Isomer B) | 474; 491 |
| 25 | N-(2-phenyl-2-tetrahydrofuroyl)-(L)-4-(2'-methoxy-phenyl)phenylalanine (Isomer A) | 446; 463 |
| 26 | N-(2-phenyl-2-tetrahydrofuroyl)-(L)-4-(2'-methoxy-phenyl)phenylalanine (Isomer B) | 446; 463 |

*m/e, (M+) or (M + H+) or (M + NH4+).

EXAMPLE 27

N-(Benzo-1,3-dioxolo-2-carbonyl)-(L)-4-(2'-methoxyphenyl)phenylalanine

Step A. Benzo-1,3-dioxole-2-carboxylic Acid, Ethyl Ester.

To a solution of 6.12 g (0.09 mol) of sodium ethoxide (33.6 ml of 21% wt in EtOH) in 30 ml of ethanol at 0° C. was added 5.0 g (0.045 mol) of catechol followed by 7.13 g of ethyl 2,2-dichloroacetate. The solution was heated to reflux for 6 hours and then stored at 0° C. over 48 hours. The reaction mixture was concentrated in vacuo and the residue was taken up in 100 ml of ether and 100 ml of saturated NaHCO$_3$ solution. The phases were separated and the aqueous phase was extracted with ether (3×50 ml). The combined ethereal phases were washed with brine and dried over MgSO$_4$. The mixture was filtered and concentrated in vacuo and the residue was purified by flash chromatography (Biotage) over silica gel eluting with 10% EtOAc/hexanes to give 1.59 g of an oil.

Selected NMR: 300 MHz $^1$H NMR (CDCl$_3$) δ 1.32 (t, 3H); 4.31 (q, 2H); 6.30 (s, 1H); 6.89 (m, 4H).

Step B. Benzo-1,3-dioxolo-2-carboxylic Acid.

0.38 g (1.96 mmol) of the product of Step A was dissolved in 10 ml of dioxane and treated with 3.9 ml (3.9 mmol) of 1N NaOH solution. The solution was stirred overnight and then acidified with 2N HCl to pH 2.0. The mixture was extracted with ethyl acetate (3×15 ml). The combined organic phase was washed with brine and was dried over MgSO$_4$. The mixture was filtered and concentrated in vacuo to give 0.38 g of a white solid.

Selected NMR: 300 MHz $^1$H NMR (CDCl$_3$): 6.33 (s, 1H); 6.89 (m, 4H).

Step C. N-(Benzo-1,3-dioxolo-2-carbonyl)-(L)-4-(2'-methoxyphenyl)phenylalanine.

0.024 g (0.14 mmol) of the product of Step B was coupled with (L)4-(2'-methoxyphenyl)phenylalanine, tert-butyl ester and following purification (preparatory thin layer chromatography over silica gel eluting with 25% EtOAc/hexanes) was treated with TFA/CH$_2$Cl$_2$ The crude product was purified by preparatory thin layer chromatography over silica gel eluting with 10% MeOH/CH$_2$Cl$_2$ 1% HOAc to give the desired product.

Selected NMR: 300 MHz $^1$H NMR (CD$_3$OD) signals: 3.09 and 3.26 (ABddd, 2H); 3.75 (s, 3H); 4.70 (dd, 1H); 6.30 (s, 1H); 6.89 (m, 4H); 6.95–7.32 (m, 8H); FABMS: Calc. C$_{24}$H$_{31}$NO$_6$; 419; Obs.: 420.

EXAMPLES 28 AND 29

N-(2(R and S)-Methyl-2-tetrahydrofuroyl)-(L)4-(2'-methoxyphenyl)phenylalanine

Step A. N-(2-Methyl-2-tetrahydrofuroyl)-(L)-4-(2'-methoxyphenyl)phenylalanine, Methyl Ester.

To a solution of 2-methyl-2-tetrahydrofuroic acid (100 mg, 0.769 mmol), hydrochloride salt of 2'-(methoxyphenyl) phenylalanine, methyl ester (247 mg, 0.769 mmol) and PyBOP (440 mg, 0.846 mmol) in methylene chloride (12 ml) cooled to 0° C. was added N,N-diisopropylethylamine (298 mg, 2.31 mmol). The cooling bath was removed after the addition. After stirring overnight at room temperature, TLC showed reaction complete. The mixture was diluted with ethyl acetate, and successively washed with 1N HCl, NaHCO$_3$, brine, dried over MgSO$_4$, filtered and concentrated. The residue was purified by preparative TLC using ethyl acetate/hexane=1:1 to afford the title compound (221 mg).400 MHz $^1$H NMR (CDCl$_3$): δ 7.45 (m, 2H); 7.27 (m, 2H); 7.13 (m, 2H); 6.97 (m, 2H); 4.84 (m, 1H); 3.85 (m, 1H); 3.77 (s, 6H); 3.74 (s, 3H); 3.72 (s, 3H); 3.21 (m, 1H); 3.07 (m, 1H); 2.33 (m, 1/2H); 2.18 (m, 1/2H); 1.75 (m, 2H); 1.55 (m, 1H); 1.38 (s, 3H), 1.33 (s, 3H).

Step B. N-(2(R and S)-Methyl-2-tetrahydrofuroyl)-L)-4-(2'-methoxyphenyl)phenylalanine To a solution of N-(2-methyl-2-tetrahydrofuroyl)-(L)-4-(2'-methoxyphenyl)phenylalanine, methyl ester (221 mg, 0.556 mmol) in 5 ml of methanol was added 0.5 M NaOH (1.7 ml, 0.834 mmol). After stirring at room temperature overnight, the reaction was partitioned between dilute acetic acid and ethyl acetate. The aqueous layer was extracted with ethyl acetate and the combined organic layer was washed with brine, dried over MgSO$_4$, filtered, and concentrated. The residue was purified by preparative TLC using methylene chloride/methanol/acetic acid=97.5:2.5:0.25. The plate was developed a total of 6 times to afford the title compound as two diastereomers (116 mg and 97 mg).
less polar diastereomer:
400 MHz $^1$H NMR (CDCl$_3$): δ 7.45 (m, 2H); 7.27 (m, 3H); 6.97 (m, 3H); 4.79 (m, 1H); 3.80 (m, 2H); 3.77 (s, 3H); 3.28 (m, 1H); 3.17 (m, 1H); 2.32 (m, 1H); 1.79 (m, 3H); 1.33 (s, 3H).

polar diastereomer:

400 MHz $^1$H NMR (CDCl$_3$): δ 7.45 (m, 2H); 7.27 (m, 3H); 6.97 (m, 3H); 4.79 (m, 1H); 3.77 (m, 4H); 3.52 (m, 1H); 3.39 (m, 1H); 3.11 (m, 1H); 2.15 (m, 1H); 1.71 (m, 2H); 1.40 (m, 4H).

| Ex. No. | Name | MS* |
|---|---|---|
| 30 | N-(2-methyl-2-tetrahydrofuroyl)-(L)-4-(2'-cyanophenyl)phenylalanine (Isomer A) | 396 |
| 31 | N-(2-methyl-2-tetrahydrofuroyl)-(L)-4-(2'-cyanophenyl)phenylalanine (Isomer B) | 396 |
| 32 | N-(2-tetrahydrofuroyl)-(L)-4-(2'-methoxyphenyl)-phenylalanine (Isomer A) | 370 |
| 33 | N-(2-tetrahydrofuroyl)-(L)-4-(2'-methoxyphenyl)-phenylalanine (Isomer B) | 370 |
| 34 | N-(2-methyl-2-tetrahydrofuroyl)-(L)-4-fluorophenylalanine | 296 |
| 35 | N-(2-methyl-2-tetrahydrofuroyl)-(L)-4-(2'-trifluoromethylsulfonylphenyl)phenylalanine (Isomer A) | 486 |
| 36 | N-(2-methyl-2-tetrahydrofuroyl)-(L)-4-(2'-trifluoromethylsulfonylphenyl)phenylalanine (Isomer B) | 486 |
| 37 | N-(2-tetrahydrofuroyl)-(L)-4-(1-morpholinocarbonyloxy)phenylalanine (Isomer A) | 424 |
| 38 | N-(2-methyl-2-tetrahydrofuroyl)-(L)-4-(1-morpholinocarbonyloxy)phenylalanine (Isomer B) | 424 |
| 39 | N-(2-methyl-2-tetrahydrofuroyl)-(L)-4-(5-[1,3-dimethyl-2,4-pyrimidinedione])phenylalanine | 416; 433 |
| 40 | N-(2-methyl-2-tetrahydrofuroyl)-(L)-4-(2-thiazolyl)phenylalanine | 360 |
| 41 | N-(2-methyl-2-tetrahydrofuroyl)-(L)-4-(2-tert-butytoxylcarbonylethyl)phenylalanine (Isomer A) | 350 (M-tBu + H$^+$) |
| 42 | N-(2-methyl-2-tetrahydrofuroyl)-(L)-4-(2-tert-butyloxylcarbonylethyl)phenylalanine (Isomer B) | 350 (M-tBu + H$^+$) |
| 43 | N-(2-methyl-2-tetrahydrofuroyl)-(L)-4-(2'-cyclopropyloxyphenyl)phenylalanine (Isomer A) | 410 |
| 44 | N-(2-methyl-2-tetrahydrofuroyl)-(L)-4-(2'-cyclopropyloxyphenyl)phenylalanine (Isomer B) | 410 |
| 45 | N-(2-methyl-2-tetrahydropyranoyl)-(L)-4-(5'-chloro-2'-methoxyphenyl)phenylalanine | 418 |
| 46 | N-(2-methyl-2-tetrahydropyranoyl)-(L)-4-(2',5'-dimethoxyphenyl)phenylalanine | 414 |
| 47 | N-(2-tetrahydrofuroyl)-(L)-2-phenyl-glycine (Isomer A) | 249 |
| 48 | N-(2-tetrahydrofuroyl)-(L)-2-phenyl-glycine (Isomer B) | 249 |
| 49 | N-(2-tetrahydrofuroyl)-(L)-phenylalanine (Isomer A) | 264 |
| 50 | N-(2-tetrahydrofuroyl)-(L)-phenylalanine (Isomer B) | 264 |
| 51 | N-(2-tetrahydrofuroyl)-(L)-homophenylalanine (Isomer A) | 173 (M-C$_8$H$_9$) |
| 52 | N-(2-tetrahydrofuroyl)-(L)-homophenylalanine (Isomer B) | 173 (M-C$_8$H$_9$) |
| 53 | N-(2-tetrahydrofuroyl)-(L)-O-(2-ethoxyethyl)-tyrosine | 352 |
| 54 | N-(2-(4'-fluorophenyl)-2-tetrahydrofuroyl)-(L)-4-(2'-methoxyphenyl)phenylalanine (Isomer A) | 464 |
| 55 | N-(2-(4'-fluorophenyl)-2-tetrahydrofuroyl)-(L)-4-(2'-methoxyphenyl)phenylalanine (Isomer B) | 464 |
| 56 | N-(2-(2'-thienyl)-2-tetrahydrofuroyl)-(L)-4-(2'-methoxyphenyl)phenylalanine (Isomer A) | 452 |
| 57 | N-(2-(2'-thienyl)-2-tetrahydrofuroyl)-(L)-4-(2'-methoxyphenyl)phenylalanine (Isomer B) | 452 |
| 58 | N-(2-methyl-2-tetrahydrofuroyl)-(L)-4-(hydroxymethyl)phenylalanine | 308.1 |
| 59 | N-(2-methyl 2-tetrahydrofuroyl)-(L)-4-(methoxymethyl)phenylalanine | 322.0 |
| 60 | N-(2-methyl-2-tetrahydrofuroyl)-(L)-3-(tert-butoxy)phenylalanine | 350.1 |
| 61 | N-(2-methyl-2-tetrahydrofuroyl)-(L)-4-(1-pyrrolidinocarbonyloxy-methyl)phenylalanine | 405.1 |
| 62 | N-(2-methyl-2-tetrahydrofuroyl)-(L)-3-(tert-butoxycarbonyl-methoxy)phenylalanine (Isomer A) | 408.1 |
| 63 | N-(2-methyl-2-tetrahydrofuroyl)-(L)-3-(tert-butoxycarbonyl-methoxy)phenylalanine (Isomer B) | 408.2 |
| 64 | N-(2(R,S)-methyl-2-tetrahydrofuroyl)-(L)-3-(1-pyrrolidino-carbonyloxy)phenylalanine | 391.2 |
| 65 | N-(2-methyl-2-tetrahydrofuroyl)-(L)-3-(2-ethoxyethoxy)phenylalanine (Isomer A) | 366.1 |

-continued

| Ex. No. | Name | MS* |
|---|---|---|
| 66 | N-(2-methyl-2-tetrahydrofuroyl)-(L)-3-(2-ethoxyethoxy)phenylalanine (Isomer B) | 366.1 |
| 67 | N-(2-methyl-2-tetrahydrofuroyl)-(L)-3-(2-methoxyethoxy)phenylalanine (Isomer A) | 352.1 |
| 68 | N-(2-methyl-2-tetrahydrofuroyl)-(L)-3-(2-methoxyethoxy)phenylalanine (Isomer B) | 352.1 |
| 69 | N-(2-methyl-2-tetrahydrofuroyl)-3(R)-amino-3-benzyl-propionic acid | 277.9 |
| 70 | N-(2-methyl-2-tetrahydrofuroyl)-3(R)-amino-3-phenylpropionic acid | 291.3 |
| 71 | N-(2-methyl-2-tetrahydrofuroyl)-3(R,S)-amino-3-(4-(3'-fluoro-2'methoxyphenyl)phenyl)-propionic acid | 401 |
| 72 | N-(2-methyl-2-tetrahydrofuroyl)-3(R,S)-amino-3-(4-(2'-fluoro-3'methoxyphenyl)phenyl)-propionic acid | 325 |
| 73 | N-(2-methyl-2-tetrahydrofuroyl)-3(R,S)-amino-3-(4-methoxyphenyl)-propionic acid | |
| 74 | N-(2-methyl-2-tetrahydrofuroyl)-3(R,S)-amino-3-(4-(2-ethoxy)ethoxyphenyl)-propionic acid | |
| 75 | N-(2-(4'-chlorophenyl)-2-tetrahydrofuroyl)-(L)-4-(2'-methoxyphenyl)phenylalanine (Isomer A) | 480.2 |
| 76 | N-(2-(4'-chlorophenyl)-2-tetrahydrofuroyl)-(L)-4-(2'-methoxyphenyl)phenylalanine (Isomer B) | 480.2 |
| 77 | N-(2-(4'-trifluoromethylphenyl)-2-tetrahydrofuroyl)-(L)-4-(2'-methoxyphenyl)phenylalanine (Isomer A) | 514.2 |
| 78 | N-(2-(4'-trifluoromethylphenyl)-2-tetrahydrofuroyl)-(L)-4-(2'-methoxyphenyl)phenylalanine (Isomer B) | 514.2 |
| 79 | N-(2-(4'-bromophenyl)-2-tetrahydrofuroyl)-(L)-4-(2'-methoxyphenyl)phenylalanine (Isomer A) | 524.1 |
| 80 | N-(2-(4'-bromophenyl)-2-tetrahydrofuroyl)-(L)-4-(2'-methoxyphenyl)phenylalanine (Isomer B) | 524.1 |
| 81 | N-(2-(4'-tert-butylphenyl)-2-tetrahydrofuroyl)-(L)-4-(2'-methoxyphenyl)phenylalanine (Isomer A) | 502.2 |
| 82 | N-(2-(4'-tert-butylphenyl)-2-tetrahydrofuroyl)-(L)-4-(2'-methoxyphenyl)phenylalanine (Isomer B) | 502.3 |
| 83 | N-(2-(3'-trifluoromethylphenyl)-2-tetrahydrofuroyl)-(L)-4-(2'-methoxyphenyl)phenylalanine (Isomer A) | 514.2 |
| 84 | N-(2-(3'-trifluoromethylphenyl)-2-tetrahydrofuroyl)-(L)-4-(2'-methoxyphenyl)phenylalanine (Isomer B) | 514.2 |
| 85 | N-(2-(3',5'-bis(trifluoromethyl)phenyl)-2-tetrahydrofuroyl)-(L)-4-(2'-methoxyphenyl)phenylalanine (Isomer A) | 582.2 |
| 86 | N-(2-(3',5'-bis(trifluoromethyl)phenyl)-2-tetrahydrofuroyl)-(L)-4-(2'-methoxyphenyl)phenylalanine (Isomer B) | 582.1 |
| 87 | N-(2-(3',4'-dimethylphenyl)-2-tetrahydrofuroyl)-(L)-4-(2'-methoxyphenyl)phenylalanine (Isomer A) | 474.3 |
| 88 | N-(2-(3',4'-dimethylphenyl)-2-tetrahydrofuroyl)-(L)-4-(2'-methoxyphenyl)phenylalanine (Isomer B) | 574.2 |
| 89 | N-(2-(4'-chlorophenyl)-2-tetrahydrofuroyl)-(L)-4-(2',6'-dimethoxyphenyl)phenylalanine (Isomer A) | 510.07 |
| 90 | N-(2-(4'-chlorophenyl)-2-tetrahydrofuroyl)-(L)-4-(2',6'-dimethoxyphenyl)phenylalanine (Isomer B) | 510.07 |
| 91 | N-(2-(4'-chlorophenyl)-2-tetrahydrofuroyl)-(L)-4-(N-(2',6'-dichlorobenzoyl)amino)phenylalanine | 561.38 |
| 92 | N-(2-methyl-2-tetrahydrothienoyl-1,1-dioxide)-(L)-4-(2'-methoxyphenyl)phenylalanine | 431; 386 |
| 93 | N-(2-methyl-2-tetrahydrothienoyl 1,1-dioxide)-(L)-4-(2',6'-dimethoxyphenyl)phenylalanine | 461; 416 |
| 94 | N-(2-methyl-2-thietanoyl 1,1-dioxide)-(L)-4-(2',6'-dimethoxyphenyl)phenylalanine | 448 |
| 95 | N-(2-methyl-2-(1,4-thioxanoyl 1,1-dioxide))-(L)-4-(2',6'-dimethoxyphenyl)phenylalanine | 478 |
| 96 | N-(2-tetrahydrothienoyl 1,1-dioxide)-(L)-4-(2'-methoxyphenyl)phenylalanine | 418.02 |
| 97 | N-(2-methyl-2-tetrahydrothienoyl 1,1-dioxide)-3(R)-amino-3-(2',6'-dimethoxy-4-biphenyl)propanoic acid | 462.11 |
| 98 | N-(2-methyl-2-tetrahydrothienoyl 1,1-dioxide)-(L)-4-(N-(2',6'-dichlorobenzoyl)amino)phenylalanine | 513.3 |

*m/e, (M$^+$) or (M + H$^+$) or (M + NH$_4^+$) or (M − CO$_2$H).

EXAMPLE 99

N-(2-Tetrahydrofuroyl)-(L)-O-(4'-methoxyphenyl) tyrosine

Step A. N-(2-Tetrahydrofuroyl)-(L)-tyrosine, tert-Butyl Ester.

2-Tetrahydrofuroic acid was activated as the pentafluorophenyl ester using a standard procedure with DCC and pentafluorophenol. The crude activated ester (5 g, 17.24 mmol) was then treated with tyrosine t-butyl ester (4.2 g, 17.72 mmol) and diisopropylethyl amine (9 ml, 52 mmol) in dioxane/methylene chloride (70 ml/70 ml) at 0° C. overnight. Solvent was removed under reduced pressure. The residue was dissolved in methylene chloride and extracted repeatedly with NaHCO$_3$ (saturated). The organic layer was dried over MgSO4, filtered and concentrated. A portion of the residue (1.1 g) was purified by silica gel chromatography with ethyl acetate/hexanes=20:80, 30:70, 40:60 to afford the desired product as an oil (710 mg).

300 MHz $^1$H NMR (CDCl$_3$): δ 7.13 (bd, 1H); 7.01 (dd, 2H); 6.70 (dd, 2H); 4.75 (m, 1H); 4.31 (m, 1H); 3.94–3.76 (m, 2H); 3.10 (m, 1H); 2.90 (m, 1H); 2.28–2.02 (m, 2H); 1.88–1.74 (m, 2H); 1.46 (s, 9H); 1.43 (s, 9H).

Step B. N-(2-Tetrahydrofuroyl)-(L)-O-(4'-methoxyphenyl) tyrosine, tert-Butyl Ester.

This compound was prepared according to a literature procedure ((D. A. Evans et al., *Tet. Lett.*, 1998, 39, 2937). A glass vial was charged with N-(2-tetrahydrofuroyl)-(L)-tyrosine, t-butyl ester (29 mg, 0.0866 mmol), Cu(Ac)$_2$ (15 mg, 0/0866mmol), 4-methoxyphenyl boronic acid (16 mg, 0.104 mmol), powdered 4 Å molecular sieves (10 mg), methylene chloride (0.9 ml) and pyridine (0.035 ml, 0.433 mmol) in that order. After stirring the green heterogeneous mixture for 18 hr at ambient temperature and atmospheric pressure, TLC showed the reaction was complete. The reaction mixture was filtered through a pad of celite with methylene chloride and concentrated. The residue was purified by preparative TLC using methylene chloride/ethyl acetate=9:1 to give the desired product (16 mg).

300 MHz $^1$H NMR (CDCl$_3$): δ 7.08 (m, 3H); 6.94 (m, 2H); 6.85 (m, 3H); 4.71 (m, 1H); 4.35 (m, 1H); 3.92–3.76 (m, 2H); 3.80 (s, 3H); 2.22 (m, 1H); 2.12–1.60 (m, 3H); 1.44 (s, 9H); 1.41 (s, 9H).

Step C. N-(2-Tetrahydrofuroyl)-(L)-O-(4'-methoxyphenyl) tyrosine.

N-(2-Tetrahydrofuroyl)-(L)-O-(4'-methoxyphenyl) tyrosine, t-butyl ester was treated with TFA as described in Reference Example 2 step C and the residue was purified by preparative TLC over silica gel using methylene chloride/methanol/acetic acid=97.5:2.5:0.25 to give two diastereomers (4 mg, and 3 mg).

less polar diastereomer:

500 MHz $^1$H NMR (CD$_3$OD): δ 7.32 (m, 2H); 6.90 (m, 4H); 6.80 (m, 2H); 4.22 (m, 1H); 3.93 (m, 1H); 3.82 (m, 1H); 3.77 (s, 3H); 3.31 (m, 1H); 3.22 (m, 1H); 3.05 (m, 1H); 2.18 (m, 1H); 1.85 (m, 3H).

more polar diastereomer:

500 MHz $^1$H NMR (CD$_3$OD): δ 7.08 (m, 1H); 6.94 (m, 2H); 6.88 (m, 4H); 4.36 (m, 1H); 3.80 (s, 3H); 3.75 (m, 2H); 3.50 (s, 1H); 3.28 (m, 1H); 3.05 (m, 1H); 2.18 (m, 1H); 1.82 (m, 2H); 1.62 (m, 1H).

The following compounds were prepared according to the procedures described in Example 99 substituting the appropriate boronic acid derivative in Step B.

| Ex. No. | Name | MS* |
|---|---|---|
| 100 | N-(2-tetrahydrofuroyl)-(L)-O-(3'-methoxyphenyl)tyrosine (Isomer A) | 386 |
| 101 | N-(2-tetrahydrofuroyl)-(L)-O-(3'-methoxyphenyl)tyrosine (Isomer B) | 386 |
| 102 | N-(2-tetrahydrofuroyl)-(L)-O-(2'-methoxyphenyl)tyrosine (Isomer A) | 386 |
| 103 | N-(2-tetrahydrofuroyl)-(L)-O-(2'-methoxyphenyl)tyrosine (Isomer B) | 386 |

*m/e, (M$^+$) or (M + H$^+$) or (M + NH$_4^+$).

EXAMPLE 104

N-(2-Methyl-2-tetrahydrofuroyl)-(L)-4-(1-pyrid-2 (1H)one)-phenylalanine

Step A. N-BOC-(L)-4-Iodophenylalanine, tert-Butyl Ester.

To a suspension of N-BOC-(L)-(4)-iodophenylalanine (5.0 g, 12.8 mmol) in dichloromethane (35 mL) and cyclohexane (70 mL) was added tert-butyl-2,2,2-trichloroacetimidate (2.4 mL, 13.4 mmol; 1.05 equiv) and boron trifluoride etherate (0.24 mL, 1.9 mmol; 0.15 equiv). The reaction mixture was stirred for 1 hr and another portion of acetimidate and BF$_3$ was added to complete the esterification. After 1.5 hr at ambient temperature, saturated NaHCO$_3$ was added and stirring was continued for 0.5 h. The layers were separated and the aqueous layer was extracted with dichloromethane (2x). The combined organic layer was washed with brine, dried (Na$_2$SO$_4$), filtered, and concentrated to provide crude ester (5.8 g). Purification by flash chromatography on silica gel (5% ethyl acetate. 95% hexanes) afforded a viscous oil (5.2 g, 91% yield) which crystallized upon standing.

$^1$H NMR (400 MHz, CDCl$_3$): δ 7.60 (d, 2H, J=11 Hz), 6.91 (d, 2H, J=11 Hz), 4.99 (d, 1H, J=10 Hz), 4.41 (q, 1H, J=10 Hz) 2.99 (m, 2H), 1.42 (s, 9H), 1.41 (s, 9H).

Step B. N-(9-(Phenylfluorenyl))-(L)-4-iodophenylalanine, tert-Butyl Ester.

To a solution of N-BOC-(L)-4-iodophenylalanine, tert-butyl ester (1.0 g, 2.24 mmol) in tert-butyl acetate (5 mL) at 0° C. was added conc. sulfuric acid (0.62 mL, 11.2 mmol; 5.0 equiv). After 5 min at ambient temperature, the reaction mixture was neutralized until the pH became basic and extracted with ethyl acetate (3x). The combined organic layer was washed with brine, dried (anhydrous magnesium sulfate), filtered, and concentrated to furnish the desired amino-ester (0.7 g, 90% yield) which was used in the next step without purification. Thus, the aminoester (0.55 g, 1.58 mmol) in acetonitrile (5 mL) was treated with triethylamine (0.46 mL, 3.3 mmol; 2.1 equiv) and 9-bromo-9-phenylfluorene (0.61 g, 1.9 mmol; 1.2 equiv). To the resulting solution was added lead nitrate (0.32 g, 0.95 mmol; 0.6 equiv) and stirring was continued for 48 h. After removal of acetonitrile, the residue was partitioned between ethyl acetate (100 mL) and 5% aqueous sodium bicarbonate (100 mL). The organic layer was washed with water and brine, dried (anhydrous magnesium sulfate), filtered, and concentrated to afford crude product which was purified by flash chromatography on silica gel (2.5% ethyl acetate, 97.5% hexanes). Yield: 0.66 g (71%) of a colorless oil which crystallized upon standing.

$^1$H NMR (400 MHz, CDCl$_3$): δ 7.62 (m, 4H), 7.54 (d, 2H, J=11 Hz), 7.33–7.13 (m, 9H), 6.95 (t, 1H), 6.81 (d, 2H, J=11 Hz), 6.68 (d, 1H) 2.98 (brs, 1H) 2.63–250 (m, 3H), 1.11 (s, 9H).

Step C. N-(9-(Phenylfluorenyl))-(L)-4-(1-pyrid-2(1H)one) phenylalanine, tert-Butyl Ester.

A mixture of N-(9-(phenylfluorenyl))-(L)-4-iodophenylalanine, tert-butyl ester (0.12 g, 0.2 mmol), 2-hydroxypyridine (27 mg, 0.29 mmol; 1.4 equiv), cesium carbonate (95 mg, 0.29 mmol; 1.4 equiv), and copper iodide (48 mg, 0.24 mmol; 1.2 equiv) in anhydrous dimethylformamide (1.0 mL) was stirred in a thick wall, screw cap vial equipped with a teflon seal at 150° C. for 8 hr under an argon atmosphere. Ethyl acetate and 1:1 mixture of saturated ammonium chloride and 10% ammonium hydroxide solution were added and stirring was continued for 0.5 h. The organic layer was separated and the aqueous layer was extracted with ethyl acetate (2×). The combined organic layer was washed with water and brine, dried (anhydrous magnesium sulfate), filtered, and concentrated to give a yellow oil (100 mg) which was purified by preparative TLC (50% ethyl acetate, 50% hexanes). Yield: 75 mg (68%) of an off-white solid.

$^1$H NMR (500 MHz, CDCl$_3$): δ 7.67 (m, 2H), 7.42–7.16 (m, 15H), 7.10 (td, 1H, J=7.5, 1.0 Hz), 6.86 (d, 1H, J=7.5 Hz), 6.67 (d, 1H, J=9.5 Hz), 6.24 (td, 1H, J=1.0 Hz), 3.09 (brs, 1H), 2.80–2.70 (m, 3H), 1.16 (s, 9H). $^{13}$C NMR (125 MHz, CDCl$_3$): δ 174.66, 163.69, 149.38, 149.23, 145.08, 141.18, 140.15, 139.97, 139.57, 138.97, 138.31, 131.10, 128.46, 128.36, 128.22, 128.03, 127.30, 126.47, 126.40, 126.17, 125.60, 122.18, 119.91, 81.13, 73.27, 57.92, 41.94, 28.12.

Step D. (L)-4-(1-pyrid-2(1H)one)-phenylalanine, Trifluoroacetate Salt.

To a solution of N-(9-(phenylfluorenyl))-(L)-(4)-(1-pyrid-2(1H)one)-phenylalanine, tert-butyl ester (70 mg, 0.13 mmol) in dichloromethane (1.0 mL) at 0° C. was added anisole (0.14 mL, 1.3 mmol; 10 equiv) and trifluoroacetic acid (0.75 mL, 9.75 mmol; 75 equiv). The reaction mixture was stirred at ambient temperature for 4 hr and then concentrated and azeotroped with toluene. The residue was triturated with anhydrous ether resulting in a white precipitate which was isolated by decanting the liquid, washing with a small quantity of ether, and drying under high vacuum. Yield: 40 mg (73%).

$^1$H NMR (400 MHz, CD$_3$OD): δ 7.65 (m, 2H), 7.48 (d, 2H, J=7.9 Hz), 7.38 (d, 2H, J=7.9 Hz), 6.65 (d, 1H, J=8.9 Hz), 6.51 (td, 1H, J=6.8, 1.0 Hz), 4.15 (brs, 1H), 3.45 (m, 1H), 3.16 (m, 1H).

Step E. (L)-4-(1-Pyrid-2(1H)one)-phenylalanine, Methyl Ester Hydrochloride.

To a solution of (L)-4-(1-pyrid-2(1H)one)-phenylalanine, trifluoroacetate salt (35 mg, 0.082 mmol) in methanol (0.8 mL) at 0° C., was added thionyl chloride (60 mL, 0.82 mmol; 10 equiv) dropwise. The cooling bath was removed and the reaction mixture was heated at 80° C. for 3.5 h, cooled to ambient temperature, and concentrated in vacuo to afford an off-white solid (25 mg, 98% yield) which was used in the next step without purification.

$^1$H NMR (400 MHz, CD$_3$OD): δ 7.78 (m, 2H), 7.46 (m, 4H), 6.79 (d, 1H), 6.68 (brt, 1H), 4.42 (br, 1H), 3.85 (s, 3H), 3.42 (m, 1H), 3.27 (m, 1H).

Step F. N-(2-Methyl-2-tetrahydrofuroyl)-(L)-4-(1-pyrid-2(1H)one)-phenylalanine, Methyl Ester.

To a suspension of (L)-4-(1-pyrid-2(1H)one)-phenylalanine, methyl ester HCl salt (14 mg, 0.045 mmol) in a mixture of dichloromethane and tetrahydrofuran (1:1, 0.8 mL) was added diisopropylethylamine (24 mL, 0.14 mmol; 3.1 equiv), 2-methyl-2-tetrahydrofuroic acid (6.5 mg, 0.05 mmol; 1.1 equiv), and benzotriazol-1-yloxytripyrrolidino-phosphonium hexafluorophosphate (26 mg, 0.05 mmol; 1.1 equiv) at 0° C. The resulting yellow-orange solution was stirred at ambient temperature for 15 h. The solvents were removed by rotary evaporation and the residue was taken in chloroform and washed with 1N HCl and saturated NaHCO$_3$. The aqueous layers were extracted with chloroform (3×) and the combined organic layer was washed with brine, dried (MgSO$_4$), filtered, and concentrated to give a yellow oil (16.5 mg, 95% crude yield). Purification by preparative TLC (90% ethyl acetate, 10% hexanes) yielded coupled material (12 mg, 70%) as a mixture of two diastereomers.

$^1$H NMR (400 MHz, CDCl$_3$): δ 7.36 (m, 1H), 7.31–7.16 (m, 6H), 6.62 (m, 1H), 6.21 (m, 1H), 4.84 (m, 1H), 3.86 (m, 1.5H), 3,74 (s, 1.5H), 3.73 (s, 1.5H), 3.67 (m, 0.5H), 3.24 (m, 1H), 3.08 (m, 1H), 2.31 (m, 0.5H), 2.17 (m, 0.5H), 1.90–1.65 (m, 3H), 1.38 (s, 1.5H), 1.33 (s, 1.5H).

Step G. N-(2-Methyl-2-tetrahydrofuroyl)-(L)-4-(1-pyrid-2(1H)one)-phenylalanine.

To a solution of N-(2-methyl-2-tetrahydrofuroyl)-(L)-4-(1-pyrid-2(1H)one)-phenylalanine, methyl ester (8.5 mg, 0.022 mmol) in methanol (0.8 mL) was added 0.5M sodium hydroxide (90 mL, 0.044 mmol; 2.0 equiv). The reaction mixture was stirred overnight (12 h) at ambient temperature, concentrated, acidified with cold 1N HCl, and extracted with chloroform (5×). The combined organic layer was washed with brine, dried (MgSO$_4$), filtered, and concentrated in vacuo to provide an off-white solid (7 mg, 86% yield) as a mixture of two diastereomers.

$^1$H NMR (400 MHz, CDCl$_3$): δ 7.44 (m, 1H), 7.39–7.25 (m, 5H), 6.70 (m, 1H), 6.30 (m, 1H), 4.81 (m, 1H), 4.06 (br, 2H), 3.85 (m, 1.5H), 3.65 (m, 0.5H), 3.25 (m, 1H), 3.12 (m, 1H), 2.31 (m, 0.5H), 2.20 (m, 0.5H), 1.90–1.60 (m, 3H), 1.39 (s, 1.5H), 1.35 (m, 1.5H); MS: m/e 371 (M+H); 388 (M+H+NH$_3$).

EXAMPLE 105

N-(2,4-Dimethyl-2-tetrahydrofuroyl)-(L)-4-(2',6'-dimethoxyphenyl)phenylalanine

Step A. N-(2,4-Dimethyl-2-tetrahydrofuroyl)-L-4-(2',6'-dimethoxyphenyl)phenylalanine, Methyl Ester The title compound was obtained by coupling of 2,4-dimethyl-2-tetrahydrofuroic acid (Reference Example 16) and hydrochloride salt of 2',6'-dimethoxyphenyl)phenylalanine, methyl ester (obtained from coupling of N-(Boc)-(L)-4-iodo-phenylalanine methyl ester and 2,6-dimethoxy boronic acid according to the procedure of Reference Example 2, Step B and subsequent removal of the (Boc) group by hydrogen chloride in ethyl acetate) according to the procedure of Example 28 and 29, Step A. Two pairs of diastereomers were obtained after chromatographic purification (gradient elution, using 10-3/1 hexane/ethyl acetate) to provide a total yield of 50%.

Diastereomers A: 500 MHz $^1$H NMR (CDCl$_3$): δ 1.00, 1.01 (2d, J=6.4 Ha, 6.7 Hz, 3H), 1.33, 1.37 (2s, 3H), 1.90, 2.05 (2 dd, J=18, 8.2 Hz, 12.9, 7.7 Hz, 1H), 2.32(m, 1H), 2.49, 2.60 (2dd, J=12.4, 6.9 Hz, 12.6, 6.9 Hz, 1H), 3.10, 3.24 (2m, 2H), 3.40 (m, 1H), 3.72 (s, 3H), 3.73, 3.75 (2s, 3H), 3.76, 3.78 (2s, 3H), 4.03 (m, 1H), 4.88 (m, 1H), 6.65 (d, J=8.4 Hz, 2H), 7.18 (m, 2H), 7.28(m, 3H)

Diastereomers B: 500 MHz $^1$H NMR (CDCl$_3$): δ 0.88, 0.93 (2d, J=6.4 Ha, 6.5 Hz, 3H), 1.41, 1.45 (2s, 3H), 1.70, 2.04 (m, 1H), 1.91, 2.05 (m, 1H), 2.38(m, 1H), 3.10, 3.24 (2m, 2H), 3.360 (m, 1H), 3.72 (s, 3H), 3.73, 3.75 (2s, 3H), 3.76, 3.78 (2s, 3H), 4.04(m, 1H), 4.88 (m, 1H), 6.65 (d, J=8.4 Hz, 2H), 7.18 (m, 2H), 7.28(m, 3H).

Step B. N-(2,4-Dimethyl-2-tetrahydrofuroyl)-(L)-4-(2',6'-dimethoxyphenyl)phenylalanine Base hydrolyses (methanolic sodium hydroxide) of N-(2,4-dimethyl-2-tetrahydrofuroyl)-(L)-4-(2',6'-dimethoxyphenyl)phenylalanine, methyl ester (diastereomers A and B from Step A, separate experiments) were carried out as described in Examples 28 and 29, Step B to give two compounds C and D. Each contained a pair of diastereomers which could not be separated by chromatography.

Compound C: 500 MHz $^1$H NMR (CD$_3$OD): δ 0.96, 0.99 (2d, J=6.5 Ha, 6.6 Hz, 3H), 1.23, 1.27 (2s, 3H), 1.35, 1.79 m, 1H), 2.00, 2.45(m, 1H), 2.30 (m, 1H), 3.10, 3.28 (2m, 2H), 3.38 (m, 1H), 3.66 (4s, 6H), 4.01 (m, 1H), 4.64 (m, 1H), 6.68 (d, J=8.4 Hz, 2H), 7.10–7.28 (m, 5H)

Compound D: 500 MHz $^1$H NMR (CD$_3$OD): δ 0.82, 0.88 (2d, J=6.4 Ha, 6.5 Hz, 3H), 1.32, 1.38 (2s, 3H), 1.52, 1.80 (m, 1H), 1.98 (m, 1H), 2.30(m, 1H), 3.10, 3.24 (2m, 2H), 3.37 (m, 1H), 3.67 (4s, 6H), 3.98(m, 1H), 4.70 (m, 1H), 6.68 (d, J=8.4 Hz, 2H), 7.12–7.28 (m, 5H)

The following compounds were prepared according to the procedures described in Example 105 substituting the appropriate substituted tetrahydrofuroic acid derivative in Step A.

| Ex. No. | Name | MS* |
|---|---|---|
| 106 | N-(2-methyl-4-methylene-2-tetrahydrofuroyl)-(L)-4-(2',6'-dimethoxyphenyl)-phenylalanine. | 426 |
| 107 | N-(2-methyl-4-(pyrrolidine-1-carbonyloxymethyl)-2-tetrahydrofuroyl)-(L)-4-(2',6'-dimethoxyphenyl)-phenylalanine | 541 |
| 108 | N-(2-methyl-4-benzoylaminomethyl-2-tetrahydro-furoyl)-(L)-4-(2',6'-dimethoxyphenyl)phenylalanine | 547 |
| 109 | N-(2-methyl-4-benzenesulfonylaminomethyl-2-tetrahydrofuroyl)-(L)-4-(2',6'-dimethoxy-phenyl)phenylalanine | 583 |

*m/e, (M$^+$) or (M + H$^+$) or (M + NH$_4^+$).

EXAMPLE 110

Methyl-4-hydroxymethyl-2-tetrahydrofuroyl)-(L)-4-(2',6'-dimethoxyphenyl)phenylalanine N-(2-Methyl-4-hydroxymethyl-2-tetrahydrofuroyl)-(L)-4-(2',6'-dimethoxyphenyl)phenylalanine, Methyl Ester (65193-285)

N-(2-methyl-4-methylene-2-tetrahydrofuroyl)-(L)-4-(2',6'-dimethoxy-phenyl)phenylalanine, methyl ester (23 mg, 0.052 mmole) was dissolved in 0.25 mL of tetrahydrofuran, cooled to 0° C., and borane-tetrahydrofuran complex (0.115 mL of a 1.0 M solution in tetrahydrofuran) was added dropwise via a hypodermic syringe. The ice bath was removed and the reaction mixture was allowed to stir at room temperature for 1 h when TLC (1/1 hexane/ethyl acetate) indicated almost complete disappearance of the starting material. The mixture was cooled to 0° C. again and treated with 0.029 mL of 30% aqueous hydrogen peroxide. After being stirred for 20 min at room temperature, the reaction mixture was diluted with ethyl acetate and washed with 5% sodium bicarbonate. The phases were separated and the aqueous phase was reextracted with ethyl acetate. The organic layers were combined and washed with water and brine and dried over anhydrous sodium sulfate. The crude product obtained after filtration and removal of volatiles was chromatographed (gradient elution using 1/0.5–3 hexane/ethyl acetate) to give two pairs of diastereomers, A (42%) and B (29%).TLC: Rf=0.1 (1:1 hexane:ethyl acetate), Mass Spectrum: ESI m/e 458 (M+1)$^+$.

Diastereomers A: 500 MHz $^1$H NMR (CDCl$_3$): δ 1.43, 1.45 (2s, 3H), 1.70(br, 1H), 1.86(dd, J=13.2, 8.7 Hz, 1H), 2.00 (dd, J=13.1, 3.1 Hz, 1H), 2.40(m, 1H), 2.92 (m, 1H), 2.98 (m, 1H), 3.10 (m, 1H), 3.42 (m, 1H), 3.53 (m, 1H), 3.72 (2s,3H), 3.74 (2s, 3H), 3.81 (2s, 3H), 3.95 (m, 1H), 4.90 (m, 1H), 6.67 (d, J=8.5 Hz, 2H), 7.14–7.35 (m, 5H)

Diastereomers B: 500 MHz $^1$H NMR (CDCl$_3$): δ 1.36, 1.37 (2s, 3H), 1.66(br, 1H), 1.95(dd, J=13.3, 6.7 Hz, 1H), 2.20 (dd, J=13.5, 4.8 Hz, 1H), 2.55(m, 1H), 3.14 (m, 1H), 3.24 (m, 1H), 3.45 (m, 1H), 3.52 (m, 1H), 3.75 (m, 1H), 3.72 (s,3H), 3.73(s, 3H), 3.77 (2s, 3H), 4.02 (m, 1H), 4.84 (m, 1H), 6.66 (d, J=8.5 Hz, 2H), 7.16–7.34 (m, 5H)

Step B. N-(2-Methyl-4-hydroxymethyl-2-tetrahydrofuroyl)-(L)-4-(2',6'-dimethoxyphenyl)phenylalanine Base hydrolyses (methanolic sodium hydroxide) of N-(2-methyl-4-hydroxymethyl-2-tetrahydrofuroyl)-(L)-4-(2',6'-dimethoxyphenyl)phenylalanine, methyl ester (diastereomers A and B from Step A, separate experiments) were carried out as described in Examples 28 and 29 Step B to give two pairs of diastereomers A and B. TLC: Rf=0.2 (10:1 dichloromethane:methanol), Mass Spectrum: ESI m/e 444 (M+1)$^+$ for both diastereomeric pairs.

Diastereomers A: 500 MHz $^1$H NMR (CDCl$_3$): δ 1.43, 1.46 (2s, 3H), 1.89 (dd, J=13.3, 8.5 Hz, 1H), 2.06 (dd, J=13.2, 4.1 Hz, 1H), 2.42 (m, 1H), 2.92 (m, 1H), 3.02 (m, 1H), 3.312 (m, 1H), 3.50 (m, 2H), 3.71–3.73 (4s,6H), 3.94 (dd, J=8.7, 6.8 Hz, 1H), 4.3 (br, 2H), 4.80 (m, 1H), 6.67 (d, J=8.4 Hz, 2H), 7.20–7.40 (m, 5H)

Diastereomers B: 500 MHz $^1$H NMR (CDCl$_3$): δ 1.24, 1.25(2s, 3H), 1.95(m,1H), 2.00–2.80(m br, 4H), 3.15 (m, 1H), 3.30 (m, 1H), 3.50–3.60 (m, 3H), 3.70 (2s,6H), 3.98 (m, 1H), 4.75 (m, 1H), 6.66 (d, J=8.5 Hz, 2H), 7.14–7.40 (m, 5H)

EXAMPLE 111

N-(2(R)-Methyl-2-tetrahydrofuroyl)-(L)-4-(2',6'-diethoxyphenyl)phenylalanine

Step A. 2,6-Diethoxybenzeneboronic Acid

This reaction was carried out according to the method of Kaliakoudas et al. (Helv. Chim. Acta, 1990, 73, 48). At 0° C., to a solution of 1,3-diethoxybenzene (598 mg, 3.6mmole) dissolved in anhydrous ether (18 mL) was added dropwise 2 mL of 1.8M solution of phenyllithium in cyclohexane/ether (70/30, from Aldrich Chemical Co.). Upon completion of addition, the ice bath was removed and the mixture allowed to stir t room temperature for 24 h. The reaction mixture was cooled to 0° C. again and trimethylborate (561 mg, 5.4 mmole) was added dropwise. After being stirred at room temperature overnight the reaction mixture was acidified with 2N aquous HCl until pH 3 was reached. Phases were separated. The aqueous layer was extracted with ethyl acetate 2 times. The organic layers were combined and washed with 2N HCl, brine, and dried over anhydrous magnesium sulfate. The crude obtained after filtration and removal of volatiles was flash chromatographed through 60 mL silica gel (gradient elution, 204/1 hexane/ethyl acetate) to provide 455 mg (60%) of the title compound as a white solid, homogeneous by TLC (Rf=0.1 in 10:1 hexane:ethyl acetate), mass spectrum: ESI, m/e 210.9 (M+1)$^+$.

500 MHz $^1$H NMR (CDCl$_3$): δ 1.49, (t, J=7.0 Hz, 3H), 4.14 (q, J=7.1 Hz, 2H), 6.60(d, J=8.5 Hz, 2H), 7.34 (t, J=8.3 Hz, 1H).

Step B. N-(2(R)-Methyl-2-tetrahydrofuroyl)-(L)-4-iodophenylalanine, Methyl Ester.

2(R)-Methyl tetrahydrofuran-2-carboxylic acid (from Reference Example 10) and (L)-4-iodophenylalanine, methyl ester hydrochloride were coupled according to the procedure of Example 28 and 29, Step A. After flash chromatography (SiO2, 10–3/1 hexane/ethyl acetate), the title compound was obtained in quantitative yield (2.2 g) as a clear oil, homogenoues by TLC (Rf=0.45 in 1:1 hexane-:ethyl acetate), mass spectrum: ESI m/e 418.3 (M+1)$^+$.

500 MHz $^1$H NMR (CDCl$_3$): δ 1.36 (s, 3H), 1.72–1.95 (m, 3H), 2.32(m, 1H), 3.00 (dd, J=13.9, 6.7 Hz, 1H), 3.13(dd, J=13.9, 5.7 Hz, 1H), 3.73(s, 3H), 3.90 (m, 2H), 4.82(m, 1H), 6.88 (d, J=8.3 Hz, 2H), 7.20 (br d, 1H), 7.61 (d, J=8.4 Hz, 2H)

Step C. N-(2(R)-Methyl-2-tetrahydrofuroyl)-(L)-4-(2',6'-diethoxyphenyl)phenylalanine, Methyl Ester.

N-($^2$(R)-Methyl-2-tetrahydrofuroyl)-(L)-4-iodophenylalanine, methyl ester was coupled to 2,6-diethoxybenzeneboronic acid mediated by tetrakis-triphenyl-phosphine palladium(0) as described in Reference Example 2, Step B to provide the title compound as an oil in 94% yield after flash chromatographic purification (SiO2, gradient elution, 10–3/1 hexne/ethyl acetate), homogenious by TLC (Rf=0.25 in 2:1 hexane:ethyl acetate), mass spectrum: ESI, m/e 456.4 (M+1)$^+$.

500 MHz $^1$H NMR (CDCl$_3$): δ 1.24 (t, J=6.9 Hz, 6H), 1.39 (s, 3H), 1.76(m, 1H), 1.88 (m, 2H), 2.38(m, 1H), 3.14 (dd, J=13.8, 6.8 Hz, 1H), 3.19(dd, J=14, 6 Hz, 1H), 3.73(s, 3H), 3.90 (m, 2H), 3.96 (q, J=6.9 Hz, 4H), 4.87 (m, 1H), 6.63 (d, J=8.3 Hz, 2H), 7.14 (d, J=8.1 Hz, 2H), 7.22 (t, J=8.3 Hz, 1H), 7.25 (br d, 1H), 7.33 (d, J=8.1 Hz, 2H)

Step D. N-(2(R)-Methyl-2-tetrahydrofuroyl)-(L)-4-(2',6'-diethoxyphenyl)phenylalanine.

The title compound was obtained from N-(2(R))-methyl-2-tetrahydro-furoyl)-(L)-4-(2',6'-diethoxyphenyl)phenylalanine, methyl ester according to the procedure of Example 28 and 29 Step B. Homogeneous by TLC (Rf=0.2 in 10:1 dichloromethane:methanol), mass spectrum: ESI m/e 442.4 (M+1)$^+$.

500 MHz $^1$H NMR (CDCl$_3$): δ 1.23 (t, J=6.9 Hz, 6H), 1.38 (s, 3H), 1.77(m, 1H), 1.85 (m, 2H), 2.36(m, 1H), 3.19 (dd, J=14.1, 7.7 Hz, 1H), 3.30(dd, J=14.2, 5.1 Hz, 1H), 3.81 (m, 1H), 3.88 (m, 1H), 3.96 (q, J=6.9 Hz, 4H), 4.85 (m, 1H), 6.62 (d, J=8.4 Hz, 2H), 7.16–7.38 (m, 5H)

The following compounds were prepared in solution by the procedures described in Example 111 substituting the appropriate alkoxybenzene in Step A:

| Ex. No. | Name | Mass Spectrum* |
|---|---|---|
| 112 | N-(2(R)-methyl-2-tetrahydrofuroyl)-(L)-4-(2'-benzyloxy-phenyl)phenylalanine | 460.4 |
| 113 | N-(2(R)-methyl-2-tetrahydrofuroyl)-(L)-4-(2'-n-propoxy-phenyl)phenylalanine | 412.4 |
| 114 | N-(2(R)-methyl-2-tetrahydrofuroyl)-(L)-4-(2'-methoxy-6'-n-propoxy-phenyl)phenylalanine | 442.5 |
| 115 | N-(2(R)-methyl-2-tetrahydrofuroyl)-(L)-4-(2'-methoxy-6'-(cyclopropylmethoxy)-phenyl)phenylalanine | 454.5 |
| 116 | N-(2(R)-methyl-2-tetrahydrofuroyl)-(L)-4-(2'-methoxy-6'-(cyclobutylmethoxy)-phenyl)phenylalanine | 468.5 |
| 117 | N-(2(R)-methyl-2-tetrahydrofuroyl)-(L)-4-(2'-methoxy-6'-(cyclohexylmethoxy)-phenyl)phenylalanine | 496.6 |
| 118 | N-(2(R)-methyl-2-tetrahydrofuroyl)-(L)-4-(2'-methoxy-6'-ethoxyphenyl)phenylalanine | 428.5 |
| 119 | N-(2(R)-methyl-2-tetrahydrofuroyl)-(L)-4-(2',6'-bis(n-propoxy)phenyl)phenylalanine | 470.5 |
| 120 | N-(2(R)-methyl-2-tetrahydrofuroyl)-(L)-4-(2',6'-bis-(cyclopropoxy)phenyl)phenylalanine | 466.5 |
| 121 | N-(2(R)-methyl-2-tetrahydrofuroyl)-(L)-4-(2'-ethoxy-6'-n-butyloxyphenyl)phenylalanine | 470.5 |

*m/e, (M$^+$) or (M + H$^+$) or (M + NH$_4^+$).

EXAMPLE 122

N-(2(R)-Methyl-2-tetrahydrofuroyl)-3-(2-(2,6-dichlorophenyl)-1,3-benzoxazol-5-yl)alanine.

Step A. N-(2(R)-Methyl-2-tetrahydrofuroyl)-3-(2-(2,6-dichlorophenyl)-1,3-benzoxazol-5-yl)alanine, tert-Butyl Ester The title compound was prepared by reacting 2(R)-methyltetrahydro-furan-2-carboxylic acid from Reference Example 10 and 3-(2-(2,6-dichlorophenyl)-1,3-benzoxazol-6-yl)alanine, tert-butyl from Reference Example 22 by the procedure described in Example 28 and 29, Step A. $^1$H-NMR showed two sets of signals suggesting a 3:1 mixture of diastereomers.

$^1$HNMR (500 MHz, CD$_3$OD) (major isomer) δ 7.67 (1H, d, J=1.5 Hz), 7.65 (1H, d, J=8.5 Hz), 7.63–7.60 (3H, m), 7.39 (1H, dd, J=8.5, 1.5 Hz), 4.60 (1H, dd, J=9.0, 5.5 Hz), 3.92–3.84 (2H, m), 3.36 (1H, dd, J=14.0, 5.5 Hz), 3.22 (1H, dd, J=14.0, 9.0 Hz 2.24–2.18 (1H, m), 1.94–1.70 (3H, m), 1.44 (9H, s), 1.21 (3H, s). LC-MS: calculated for C$_{26}$H$_{28}$Cl$_2$N$_2$O$_5$, 518; found m/e 519 (M+H$^+$).

Step B. N-(2(R)-Methyl-2-tetrahydrofuroyl)-3-(2-(2,6-dichlorophenyl)-1,3-benzoxazol-5-yl)alanine.

To a solution of the ester from Step A (105 mg, 0.23 mmol) in 1 mL of methylene chloride was added 1 mL of trifluoroacetic acid. After stirring at room temperature for 3 h, the mixture was diluted with heptane, and was concentrated to dryness. The residue was further azeotroped with 1 M HCl in ether/heptane to give the final product (100 mg, 100%). $^1$H-NMR showed two sets of signals suggesting a 3:1 mixture of diastereomers.

$^1$HNMR (500 MHz, CD$_3$OD) (major isomer) δ 7.68 (1H, d, J=1.5 Hz), 7.64 (1H, d, J=8.5 Hz), 7.62–7.59 (3H, m), 7.39 (1H, dd, J=8.5, 2.0 Hz), 4.73 (1H, dd, J=9.0, 5.0 Hz), 3.92–3.84 (2H, m), 3.45 (1H, dd, J=14.0, 5.0 Hz), 3.25 (1H, dd, J=14.0, 9.0 Hz 2.21 (1H, m), 1.94–1.68 (3H, m), 1.20 (3H, s); LC-MS: calculated for C$_{22}$H$_{20}$Cl$_2$N$_2$O$_5$, 462; found m/e 463 (M+H$^+$).

EXAMPLE 123

N-(2-Methyl-4-(N-pyrrolidino)-2-tetrahydrofuroyl)-(L)-4-(2',6'-dimethoxyphenyl)phenylalanine Step A. N-[2-Methyl-4-oxo-2-tetrahydrofuroyl]-(L)-4-(2',6'-dimethoxy-phenyl)phenylalanine, t-Butyl Ester The title compound was obtained by coupling of 2-methyl-4-oxo-2-tetrahydrofuroic acid (Reference Example 21) and the hydrochloride salt of 4-(2',6'-dimethoxyphenyl)phenylalanine, t-butyl ester (obtained from coupling of N-(Boc)-(L)-4-iodo-phenylalanine t-butyl ester and 2,6-dimethoxyboronic acid as described in Reference Example 2, Step B and subsequent removal of the (Boc) group by hydrogen chloride in ethyl acetate) according to the procedure of Example 28 and 29, Step A. This provided the desired compound as an inseparable mixture of 2 diastereomers in 76% yield; homogeneous by TLC (Rf= 0.6, 1/1 hexane/ethyl acetate). Mass spectrum (LC/MS) m/e 484 (M+1)$^+$.

NMR: 500 MHz $^1$H NMR (CDCl$_3$) δ 1.44, 1.50 (2s, 9 H), 1.52, 1.61 (2s, 3H), 2.36 (m, 1H), 2.96–3.32 (m, 3H), 3.56–4.15 (m, 2H), 3.72, 3.73 (2s, 6H), 4.68, 4.78 (2m, 1H), 6.66 (m, 2H), 7.12–7.32 (m, 5H)

Step B. N-[2-Methyl-4-(N-pyrrolidino)-2-tetrahydrofuroyl]-(L)-4-(2',6'-dimethoxyphenyl)phenylalanine, t-Butyl Ester A solution of 2-methyl-4-oxo-tetrahydrofuroyl-(L)-4-(2',6'-dimethoxyphenyl)phenylalanine, t-butyl ester (20 mg, 0.414 mmol, obtained from Step A) and 1,2-dichloroethane (0.13 mL) was treated with pyrrolidine (2.90 mg) followed by sodium triacetoxyborohydride (12 mg). After being stirred at room temperature for 4 h, the reaction mixture was diluted with ethyl acetate and quenched with 1N NaOH. The aqueous phase was extracted twice more with ethyl acetate. The organic layers were combined, washed with brine, and dried over anhydrous sodium sulfate. The crude product obtained after filtration and removal of volatiles was chromatographed over a plug of silica gel, eluting with 0–8% methanol in dichloromethane. This provided 18 mg (82%) of the desired product as a clear foam, homogeneous by TLC (Rf=0.5 in 5% methanol/dichloromethane). The diastereomeric pairs were not separable by TLC.

Mass spectrum (LC/MS) m/e 539 (M+1)+. NMR: 500 MHz $^1$H NMR (CDCl$_3$) δ 1.37, 1.40 (2s, 9 H), 1.40, 1.43, 1.45 (3s, 3H), 1.64–1.84 (m, 5H), 2.02–2.10 (m, 1H), 2.30–2.70 (m, 4H), 2.84–3.14 (m, 3H), 3.75–4.02 (m, 2H), 3.71, 3.72 (2s, 6H), 4.68, 4.72(2m, 1H), 6.65 (m, 2H), 7.18–7.32 (m, 5H), 7.41, 7.49(2d, J=7.9, 8.0 Hz,1H)

Step C. N-[2-Methyl-4-(N-pyrrolidino)-2-tetrahydrofuroyl]-(L)-4-(2',6'-dimethoxyphenyl)phenylalanine The title compound was obtained by treating 2-methyl-4-(N-pyrrolidino)-2-tetrahydrofuroyl)-(L)-4-(2',6'-dimethoxyphenyl)phenylalanine, t-butyl ester (obtained from Step B) with excess 1/1 trifluoroacetic acid/dichloromethane at 0° C. After being stirred at room temperature for 2 h, excess trifluoroacetic acid was removed via a stream of nitrogen and the residue was purified using a silica gel SepPak cartridge, eluting with 0.5–16% methanol in dichloromethane, providing 2 pairs of diastereomers (Rf=0.6 and 0.4 in 60/40 acetonitrile/water).

Mass spectrum (LC/MS) m/e 483 (M+1)+.

Isomer A NMR: 500 MHz $^1$H NMR (CD$_3$OD) δ 1.42, 1.48, (2s, 3H), 1.85–2.10 (m, 5H), 2.28–2.58 (m, 2H), 2.65–2.80 (m, 1H), 3.20 (m, 7H), 3.67, 3.71 (2s, 6H), 3.80,3.85 (2m, 1H), 4.05, 4.21 (2m, 1H), 6.68 (m, 2H), 7.15–7.30 (m, 5H) Isomer B NMR: 500 MHz $^1$H NMR (CD$_3$OD) δ 1.37, 1.40, (2s, 3H), 1.96–2.06 (m, 4H), 2.20 (m 1H), 2.55–2.65 (m, 2H), 3.10–3.30 (m, 6H), 3.66, 3.67 (2s, 6H), 3.90, 4.20 (2m, 2H), 4.00,4.42 (2m, 1H), 6.68 (m, 2H), 7.06–7.28 (m, 5H)

The following compounds were prepared according to the procedures described in Example 123, substituting morpholine for pyrrolidine in Step B.

| Example No. | Name | MS* |
|---|---|---|
| 124 | N-[2-Methyl-4-(N-morpholinyl)-2-tetrahydrofuroyl)]-(L)-4-(2',6'-dimethoxyphenyl)phenylalanine (Isomers A & B) | 499 |
| 125 | N-[2-Methyl-4-(N-morpholinyl)-2-tetrahydrofuroyl)]-(L)-4-(2',6'-dimethoxyphenyl)phenylalanine (Isomers C & D) | 499 |

The following compound was prepared according to the procedures described in Example 123, substituting the appropriate boronic acid in Step A.

| Example No. | Name | MS* |
|---|---|---|
| 126 | N-(2-Methyl-4-(N-pyrrolidinyl)-2-tetrahydrofuroyl)-(L)-4-(2',6'-dimethoxy-4'-(1-pyrrolidinylmethyl)phenyl)-phenylalanine | 794 |

The following compound was prepared according to the procedures described in Example 111 substituting the appropriate alkoxybenzene in Step A.

| Example No. | Name | MS* |
|---|---|---|
| 127 | N-(2-Methyl-2-tetrahydrofuroyl)-(L)-4-(1,3-dimethoxy-2-naphthyl)phenylalanine | 464 |

EXAMPLE 128

N-(2,5-Dimethyl-3-oxo-2-tetrahydrofuroyl)-(L)-4-(2',6'-dimethoxyphenyl)phenylalanine Step A. N-(2,5-dimethyl-3-oxo-2-tetrahydrofuroyl)-(L)-4-(2',6'-dimethoxyphenyl)phenylalanine, t-Butyl Ester The title compound was obtained by the procedure of Example 122 Step A, using 2,5-dimethyl-3-oxo-2-tetrahydrofuroic acid (Reference Example 23) as the acid component. This provided the desired compound cleanly as a gum (95%), homogeneous by TLC (Rf=0.5 1/1 Hexane/ethyl acetate).

Mass spectrum (LC/MS) m/e 498 (M+1)+. NMR: 400 MHz $^1$H NMR (CDCl$_3$) δ 1.36, 1.47 (2d, J=6H, 3H), 1.40, 1.48, (2s, 9H), 1.50, 1.60 (2s, 3H), 2.06, 2.31 (2dd, J=17.6, 10.2 Hz, 1H), 2.54, 2.64 (2dd, J=18, 5.9 Hz, 1H), 3.04, 3.26 (m,1H), 3.72 (s, 6H), 4.28, 4.46(m, 1H), 4.74(m, 1H), 6.66 (dd, J=8.4, 1.4 Hz, 2H), 7.06–7.36 (m, 5H)

Step B. N-(2,5-Dimethyl-3-oxo-2-tetrahydrofuroyl)-(L)-4-(2',6'-dimethoxyphenyl)phenylalanine The title compound was obtained from N-(2,5-dimethyl-3-oxo-2-tetrahydrofuroyl)-(L)-4-(2',6'-dimethoxyphenyl) phenylalanine, t-butyl ester (Step A) according to the procedure of Example 123, Step C. Mass spectrum (LC/MS) m/e 441 (M+1)+.

NMR: 500 MHz $^1$H NMR (CD$_3$OD) δ 1.31, 1.38 (2d, J=6H, 3H), 1.33, 1.37 (2s, 3H), 1.90–2.28 (m, 1H), 2.32–2.62 (m, 1H), 3.05–3.25 (m,2H), 3.64, 3.65 (2s, 6H), 4.31, 4.37(m, 1H), 4.67(m, 1H), 6.66 (d, J=8.5 Hz, 2H), 7.03–7.28 (m, 5H), 7.65,7.72 (2d, J=8.0 Hz, 1H)

The following compound was prepared according to the procedures described in Example 128 substituting the appropriate substituted tetrahydrofuroic acid in Step A.

| Example No. | Name | MS* |
|---|---|---|
| 129 | N-(5-Benzyl-2-methyl-3-oxo-2-tetrahydrofuroyl)-(L)-4-(2',6'-dimethoxyphenyl)phenylalanine | 518 |
| 130 | N-(2-Methyl-3-oxo-5-phenyl-2-tetrahydrofuroyl)-(L)-4-(2',6'-dimethoxyphenyl)phenylalanine | 504 |
| 131 | N-(3-Hydroxy 2-methyl-5-phenyl-2-tetrahydrofuroyl)-(L)-4-(2',6'-dimethoxyphenyl)phenylalanine (Isomer A) | 444 |
| 132 | N-(3-Hydroxy 2-methyl-5-phenyl-2-tetrahydrofuroyl)-(L)-4-(2',6'-dimethoxyphenyl)phenylalanine (Isomer B) | 444 |
| 133 | N-(3-Hydroxy 2-methyl-5-phenyl-2-tetrahydrofuroyl)-(L)-4-(2',6'-dimethoxyphenyl)phenylalanine (Isomer C) | 444 |
| 134 | N-(3-Methoxycarbonylmethyl-2-methyl-5-phenyl-2-tetrahydrofuroyl)-(L)-4-(2',6'-dimethoxyphenyl)-phenylalanine | 500 |

EXAMPLE 135

N-(2,5-Dimethyl-3-(4-methoxybenzylamino)-2-tetrahydrofuroyl)-(L)-4-(2',6'-dimethoxyphenyl) phenylalanine Step A. N-(2,5-Dimethyl-3-(4-methoxybenzylamino)-2-tetrahydrofuroyl)-(L)-4-(2',6'-dimethoxyphenyl) phenylalanine, t-Butyl Ester The title compound was obtained by treating a solution of N-(2,5-dimethyl-3-oxo-2-tetrahydrofuroyl)-(L)-4-(2',6'-dimethoxyphenyl)phenylalanine, t-butyl ester (64 mg, 0.129 mmole, Example 128, Step A) in 0.4 mL of 1,2-dichloroethane with sodium triacetoxyborohydride (39 mg) and glacial acetic acid (7.7 mg) and 4-methoxybenzylamine according to the procedure of Example 122, Step B. Two fractions were isolated after chromatography. Mass spectrum (LC/MS) m/e 619 (M+1)+.

Fraction A NMR: 500 MHz $^1$H NMR (CDCl$_3$) δ 1.24, 1.44 (d, J=6H, 3H), 1.39, 1.45, (2, 3H), 1.42 (s, 9H), 1.90–2.50 (m, 2H), 3.03–3.25(m, 3H), 3.73 (s, 6H), 3.80 (m, 2H), 4.11 (m, 1H), 4.78 (m, 1H), 6.65 (m, 3H), 6.85 (m, 1H), 7.20–7.35(m, 7H), 7.55(m, 1H) Fraction B NMR: 500 MHz $^1$H NMR (CDCl$_3$) δ 1.24–1.50 (m, 6H), 1.41 (s, 9H), 1.70–2.50 (m, 2H), 3.03–3.25(m, 3H), 3.73 (s, 6H), 3.80 (m, 2H), 4.11 (m, 1H), 4.78 (m, 1H), 6.65 (m, 2H), 6.85 (m, 2H), 7.20–7.35(m, 7H), 7.55(m, 1H)

Step B. N-(2,5-Dimethyl-3-(4-methoxybenzylamino)-2-tetrahydrofuroyl)-(L)-4-(2',6'-dimethoxyphenyl)phenylalanine The title compound was obtained from N-(2,5-dimethyl-benzylamino)-2-tetrahydrofuroyl)-(L)-4-(2',6'-dimethoxyphenyl)phenylalanine, t-butyl ester (Step A) according to the procedure of Example 123, Step C. Mass spectrum (LC/MS) m/e 562 (M+1)$^+$. NMR: 500 MHz $^1$H NMR (CD$_3$OD) δ 1.12–1.55 (m, 6H), 2.38–2.48 (m, 2H), 3.10–3.40 (m, 3H), 3.65 (s, 6H), 3.80 (m, 2H), 4.0–4.3(m, 1H), 4.65–4.75(m, 1H), 6.66 (m, 2H), 6.95(m, 2H), 7.1–7.5 (m, 5H)

EXAMPLE 136

N-(3-Amino-2,5-dimethyl-2-tetrahydrofuroyl)-(L)-4-(2',6'-dimethoxyphenyl)phenylalanine Step A. N-(3-Amino-2.5-dimethyl-2-tetrahydrofuroyl)-(L)-4-(2'6'-dimethoxy-phenyl)phenylalanine, t-Butyl Ester The title compound was obtained by transfer hydrogenolysis of N-(2,5-dimethyl-3-(4-methoxybenzyl)-2-tetrahydrofuroyl)-(L)-4-(2',6'-dimethoxyphenyl)phenylalanine, t-butyl ester (Example 135, Step A) overnight in refluxing methanol, using palladium hydroxide and excess ammonium formate. After being cooled to room temperature, the reaction mixture was filtered over a pad of cetlite, washed with methanol and pumped to dryness. Silica gel purification via SepPak provided a 65% yield of the desired product, homogeneous by TLC (Rf=0.1, 1/1 hexane/ethyl acetate), Mass spectrum (LC/MS) m/e 499 (M+1)$^+$.

NMR: 500 MHz $^1$H NMR (CDCl$_3$) δ 1.20–1.35 (m, 3H), 1.40–1.50 (m, 12H), 2.25–2.45(m, 1H), 2.60 (br s, 2H), 3.13 (m, 2H), 3.20(m, 1H), 3.40(m, 1H), 3.70(s, 6H), 4.15 (m, 1H), 4.75 (m, 1H), 6.65 (m, 2H), 7.20–7.35(m, 5H)

Step B. N-(3-Amino-2,5-dimethyl-2-tetrahydrofuroyl)-(L)-4-(2',6'-dimethoxy-phenyl)phenylalanine The title compound was obtained from N-(3-amino-2,5-dimethyl-2-tetrahydrofuroyl)-(L)-4-(2',6'-dimethoxyphenyl)phenylalanine, t-butyl ester (Step A) according to the procedure of Example 123, Step C. Mass spectrum (LC/MS) m/e 443 (M+1)$^+$.

NMR: 500 MHz $^1$H NMR (CD$_3$OD) δ 1.20–1.35 (m, 3H), 1.40–1.50 (m, 3H), 2.25–2.45(m, 1H), 2.60 (br s, 2H), 3.13 (m, 2H), 3.20(m, 1H), 3.35(m, 1H), 3.65, 3.68(2s, 6H), 4.22 (m, 1H), 4.68–4.86 (m, 1H), 6.65 (m, 2H), 7.20–7.35(m, 5H)

EXAMPLE 137

N-(2-(2-Hydroxyethyl)-2-tetrahydrofuroyl)-(L)-4-2',6'-dimethoxyphenyl)phenylalanine Step A. 2-(2-tert-Butyl-dimethylsilyloxyethyl)-2-tetrahydrofuroic Acid, Benzyl Ester.

To a solution of N,N-diisopropylamine (4 mL, 34 mmol) in THF (30 mL) at 0° C. was added n-butyllithium (14 ml, 34 mmol, 2.5 M/Hex). After stirring the mixture for 30 min, it was cooled to −78° C. and 2-tetrahydrofuroic acid, benzyl ester (5.8 g, 28.3 mmol) in THF (20 mL) was added, followed by HMPA (5.9 mL, 34 mmol). After 1 hr at −78° C., 2-tert-butyl-dimethylsilyloxyethyl iodide (16 g, 56.6 mmol) was added and the reaction mixture was allowed to warm to room temperature slowly over night. The reaction mixture was partitioned between ethyl acetate (200 mL) and NH$_4$Cl (sat. 200 mL). The aqueous layer was extracted with ethyl acetate (2×200 mL). The combined organic layers was washed with NH$_4$Cl, H$_2$O and brine, dried over anhydrous MgSO4, filtered, and concentrated. The residue was purified by column chromatography on silica gel eluted with ethyl acetate/hexane=5:95 to afford the desired product as an oil (2.3 g).

400 MHz $^1$H NMR (CDCl$_3$) δ 7.35 (m, 5H); 5.18 (s, 2H); 3.96 (m, 2H); 3.75 (m, 1H); 3.65 (m, 1H); 2.24 (m, 2H); 1.92 (m, 4H); 0.87 (s, 9H); 0.028 (s, 6H).

Step B. 2-(2-tert-Butyl-dimethylsilyloxyethyl)-2-tetrahydrofuroic Acid.

To a solution of 234 mg (0.643 mmol) of 2-(2-tert-butyl-dimethylsilyl-oxyethyl)-2-tetrahydrofuroic acid, benzyl ester from Step A in ethanol (5ml) was added NaHCO$_3$ (108 mg, 1.29 mmol) and Pd on carbon (10%, 10 mg). Hydrogenation was carried out under 40 PSI of hydrogen at room temperature for 3 hr. The reaction mixture was filtered, concentrated in vacuo and used directly in the next reaction without further purification.

Step C. N-(2-(2-tert-Butyldimethylsiloxyethyl)-2-tetrahydrofuroyl)-(L)-4-(2',6'-dimethoxyphenyl)phenylalanine, tert-Butyl Ester The procedure described in Example 28, Step A was applied to 23 mg of 2-(2-tert-butyl-dimethylsilyloxyethyl)-2-tetrahydrofuroic acid from Step B and (L)-4-(2',6'-dimethoxyphenyl)phenylalanine, tert-butyl ester hydrochloride (from Reference Example 26) to give 31 mg of the title compound as an oil.

400 MHz $^1$H NMR (CDCl$_3$) δ 7.27 (m, 5H); 6.66 (m, 2H); 4.72 (m, 1H); 3.91 (m, 1H); 3.80 (m, 1H); 3.72 (s, 3H); 3.71 (s, 3H); 3.19 (m, 1H); 3.03 (m, 1H); 2.25 (m, 0.5H); 1.99–1.62 (m, 4.5H); 1.45 (s, 4.5H); 1.37(s, 4.5H); 0.88 (s, 9H); 0.045 (s, 6H).

Step D. N-(2-(2-Hydroxyethyl)-2-tetrahydrofuroyl)-(L)-4-(2',6'-dimethoxyphenyl)phenylalanine, tert-Butyl Ester.

To a solution of 6 mg (0.01 mmol) of N-(2-(2-tert-butyldimethylsiloxy-ethyl)-2-tetrahydrofuroyl)-(L)-4-(2',6'-dimethoxyphenyl)phenylalanine, tert-butyl ester hydrochloride from Step C in THF (0.2 mL) was added tetra-butylammonium fluoride (0.02 mL, 0.0196 mmol) at room temperature. After 1 hr, the reaction mixture was partitioned between water and ethyl acetate. The organic layer was washed with brine and dried over anhydrous MgSO4, filtered, concentrated in vacuo to give the desired product (8 mg).

400 MHz $^1$H NMR (CDCl$_3$) δ 7.27 (m, 5H); 6.66 (m, 2H); 4.77 (m, 1H); 3.91–3.75 (m, 8H); 3.48–3.20 (m, 3H); 3.05 (m, 1H); 2.24 (m, 1H); 2.19 (m, 0.5H); 1.91–1.59 (m, 4.5H); 1.47 (s, 4.5H); 1.39 (s, 4.5H).

Step E. N-(2-(2-Hydroxyethyl)-2-tetrahydrofuroyl)-(L)-4-(2',6'-dimethoxy-phenyl)phenylalanine.

The procedure described in Reference Example 1, Step D was applied to 8 mg of N-(2-(2-hydroxyethyl)-2-tetrahydrofuroyl)-(L)-4(2',6'-dimethoxyphenyl)phenylalanine, tert-butyl ester from Step D above to give 6 mg of the title compound.

400 MHz $^1$H NMR (CDCl$_3$) δ 7.27 (m, 5H); 6.66 (m, 2H); 4.84 (m, 1H); 4.48–4.22 (m, 2H); 3.91–3.78 (m, 1H); 3.52–3.43 (m, 1H); 3.32–3.02 (m, 2H); 2.33 (m, 1H); 2.01–1.34 (m, 5H).

The following compound was prepared according to the procedures described in Example 137 substituting 3-tertbutyl-dimethylsilyloxypropyl iodide for 2-tert-butyl-dimethylsilyloxyethyl iodide in Step A:

| Ex. No. | Name | MS* |
|---|---|---|
| 138 | N-(2-(3-Hydroxypropyl)-2-tetrahydrofuroyl)-(L)-4-(2',6'-dimethoxyphenyl)phenylalanine | 458 |

EXAMPLE 139

N-(2-Acetoxyethyl-2-tetrahydrofuroyl)-(L)-4-(2'6'-dimethoxyphenyl)phenylalanine)

Step A. N-(2-(2-Acetoxyethyl)-2-tetrahydrofuroyl)-(L)-4-(2',6'-dimethoxy-phenyl)phenylalanine), tert-Butyl Ester.

To a solution of 20 mg (0.04 mmol) of N-(2-(2-hydroxyethyl)-2-tetrahydrofuroyl)-(L)-4(2',6'-dimethoxyphenyl)phenylalanine, tert-butyl ester from Example 137, Step D in pyridine (0.5 mL) at 0° C. was added acetic anhydride (0.014 mL, 0.16 mmol). The reaction mixture was allowed to warm to room temperature and stirred over night. It was partitioned between ethyl acetate and 0.5 N HCl. The organic phase was washed with brine, dried with anhydrous MgSO4, concentrated and dried in vacuo. The residue was purified by preparative TLC on silica gel eluting with 1:1 ethyl acetate/hexane to give 23 mg of the product.

400 MHz $^1$H NMR (CDCl$_3$) δ 7.30–7.18 (m, 5H); 6.65 (d, J=8 Hz, 2H); 4.75 (m, 1H); 4.22–3.82 (m, 4H); 3.71 (s, 6H); 3.28–3.04 (m, 2H); 2.33–2.15 (m, 2H); 2.06 (s, 1.5H); 2.01 (s, 1.5H); 1.93–1.65 (m, 4H); 1.46 (s, 4.5H); 1.40 (s, 4.5H).

Step B. N-(2-(2-Acetoxyethyl)-2-tetrahydrofuroyl)-(L)-4-(2',6'-dimethoxy-phenyl)phenylalanine)

The procedure described in Reference Example 1, Step D was applied to 23 mg of N-(2-(2-acetoxyethyl)-2-tetrahydrofuroyl)-(L)-4-(2',6'-dimethoxyphenyl)phenylalanine), tert-butyl ester from Step A above to give 20 mg of the title compound.

400 MHz $^1$H NMR (CD$_3$OD) δ 7.27–7.13 (m, 5H); 6.68 (d, J=8 Hz, 2H); 4.78 (m, 0.5H); 4.66 (m, 0.5H); 4.07–3.74 (m, 4H); 3.65 (s, 6H); 3.39–3.08 (m, 2H); 1.95 (s, 1.5H); 1.85 (s, 1.5H); 1.86–1.75 (m, 4H).

The following compound was prepared according to the procedures described in Example 139 substituting N-(2-(3-hydroxypropyl)-2-tetrahydrofuroyl)-(L)-4-(2', 6'dimethoxyphenyl)phenylalanine, tert-butyl ester for N-(2-(2-hydroxyethyl)-2-tetrahydrofuroyl)-(L)-4-(2',6'-dimethoxyphenyl)phenylalanine, tert-butyl ester in Step A:

| Ex. No. | Name | MS* |
|---|---|---|
| 140 | N-(2-(3-Acetoxypropyl)-2-tetrahydrofuroyl)-(L)-4-(2',6'-dimethoxyphenyl)phenylalanine | 500 |

EXAMPLE 141

N-(2-(2-Methoxyethyl)-2-tetrahydrofuroyl)-(L)-4-(2',6'-dimethoxyphenyl)phenylalanine Step A. N-(2-(2-Methoxyethyl)-2-tetrahydrofuroyl)-(L)-4-(2',6'-dimethoxy-phenyl)phenylalanine, tert-Butyl Ester.

To a solution of 40 mg (0.08 mmol) of N-(2-(2-hydroxyethyl)-2-tetrahydrofuroyl)-(L)-4-(2',6'-dimethoxyphenyl)phenylalanine, tert-butyl ester from Example 137, Step D in dichloromathane (1 mL) at 0° C. was added 2,6-lutidine (0.045 mL, 0.2 mmol) and methyl trifluoromethanesulfonate (0.023 miL, 0.16 mmol). The cooling bath was removed after addition. The reaction mixture was allowed to stir overnight at room temperature. The reaction mixture was then partitioned between ethyl acetate (20 mL) and 0.5 N HCl (20 mL). The aqueous layer was extracted with fresh ethyl acetate (20 mL). Combined organic portions were washed with brin'e and dried over anhydrous MgSO4. The mixture was filtered, concentrated in vacuo and the residue was purified by preparative TLC on silica gel eluting with 1:1 ethyl acetate/hexane to give 26 mg of the desired product.

300 MHz $^1$H NMR (CDCl$_3$) δ 7.27 (m, 5H); 6.66 (d, J=6 Hz, 2H); 4.73 (m, 1H); 3.91 (m, 1H); 3.80 (m, 0.5H); 3.69 (s, 6H); 3.63 (m, 0.5H); 3.51–3.33 (m, 2H); 3.27 (s, 1.5H); 3.22 (s, 1.5H); 3.19–3.01 (m, 2H) 2.22 (m, 2H); 1.85 (m, 4H); 1.43 (s, 4.5H); 1.36 (s, 4.5H).

Step B. N-(2-(2-Methoxyethyl)-2-tetrahydrofuroyl)-(L)4-(2',6'-dimethoxy-phenyl)phenylalanine.

The procedure described in Reference Example 1, Step D was applied to 26 mg of N-(2-(2-methoxyethyl)-2-tetrahydrofuroyl)-(L)-4-(2',6'-dimethoxy-phenyl)phenylalanine, tert-butyl ester from Step A above to give 26 mg of the title compound.

400 MHz $^1$H NMR (CD$_3$OD) δ 7.27–7.13 (m, 5H); 6.68 (d, J=8 Hz, 2H); 4.75 (m, 0.5H); 4.67 (m, 0.5H); 3.66 (s, 6H); 3.50–3.00 (m, 7H); 2.21–1.74 (m, 6H).

The following compound was prepared according to the procedures described in Example 141 substituting N-(2-(3-hydroxypropyl)-2-tetrahydrofuroyl)-(L)-4-(2',6'-dimethoxyphenyl)phenylalanine, tert-butyl ester or N-(2-(4-hydroxybutyl)-2-tetrahydrofuroyl)-(L)-4-(2', 6'dimethoxyphenyl)phenylalanine, tert-butyl ester for N-(2-(2-hydroxyethyl)-2-tetrahydrofuroyl)-(L)-4-(2', 6'methoxyphenyl)phenylalanine, tert-butyl ester in Step A:

| Ex. No. | Name | MS* |
|---|---|---|
| 142 | N-(2-(3-methoxypropyl)-2-tetrahydrofuroyl)-(L)-4-(2',6'-dimethoxyphenyl)phenylalanine | 473 |
| 143 | N-(2-(4-methoxybutyl)-2-tetrahydrofuroyl)-(L)-4-(2',6'-dimethoxyphenyl)phenylalanine | 487 |

EXAMPLE 144

N-(2-(2-Aminoethyl)-2-tetrahydrofuroyl)-(L)-4-(2'6'-dimethoxyphenyl)phenylalanine Step A. N-(2-(2-Azidoethyl)-2-tetrahydrofuroyl)-(L)-4-(2,6'-dimethoxy-phenyl)phenylalanine, tert-Butyl Ester.

To a solution of 55 mg (0.11 mmol) of N-(2-(2-hydroxyethyl)-2-tetrahydrofuroyl)-(L)-4-(2',6'-dimethoxyphenyl)phenylalanine, tert-butyl ester from Example 137, Step D in toluene/dichloromethane (1 mL/1 ml) at 0° C. was added triethyl amine (0.015 mL, 0.11 mmol) and methyl methanesulfonyl chloride (0.009 mL, 0.11 mmol). Precipitation was observed immediately. After 30 min, another portion of triethyl amine and methanesulfonyl chloride was added in order to achieve complete consumption of starting material. Then tetrabutyl ammonium bromide ((35 mg, 0.11 mmol) and sodium azide (60 mg, 0.94 mmol) was added and the reaction mixture was heated at 60° C. over 3 days. It was then partitioned between dilute acetic acid and ether and extracted with ether once more. The combined extracts were washed with brine, dried over anhydrous MgSO4, concentrated and dried in vacuo. The residue was purified by preparative TLC on silica gel eluting with 1:1 ethyl acetate/hexane to give 12 mg of the desired product.

400 MHz $^1$H NMR (CDCl$_3$) δ 7.30–7.18 (m, 5H); 6.65 (d, J=8 Hz, 2H); 4.75 (m, 1H); 3.96 (m, 1.5H); 3.83 (m, 0.5H); 3.72 (s, 3H); 3.71 (s, 3H); 3.69–3.02 (m, 2.51–2.18 (m, 2H); 2.06–1.78 (m, 3H); 1.64–1.55 (m, 1H);1.48 (s, 4.5H); 1.42 (s, 4.5H).

Step B. N-(2-(2-Aminoethyl)-2-tetrahydrofuroyl)-(L)-4-(2', 6'-dimethoxy-phenyl)phenylalanine, tert-butyl ester.

To a solution of 12mg of N-(2-(2-azidoethyl)-2-tetrahydrofuroyl)-(L)-4-(2',6'-dimethoxyphenyl) phenylalanine, tert-butyl ester from Step A above in methanol (1 mL) was added Pd on carbon (10 mg, 10%). Hydrogenation was carried out under 40 psi of hydrogen overnight. It was filtered, concentrated and purified by preparative TLC on silica gel eluting with 9:1 dichloromethane/methanol to give 3 mg of the desired product.

400 MHz $^1$H NMR (CDCl$_3$) δ 7.38–7.18 (m, 5H); 6.65 (m, 2H); 4.88 (m, 1H); 4.67 (m, 1H); 4.03 (m, 1H); 3.94 (m, 0.5H); 3.77 (s, 3H); 3.71 (s, 3H); 3.72–3.69 0.5H); 3.36–3.26 (m, 1H); 3.14–3.00 (m, 1.5H); 2.68 (m, 0.5H); 2.38–2.11 (m, 1.49 (s, 9H).

Step C. N-(2-(2-Aminoethyl)-2-tetrahydrofuroyl)-(L)-4-(2'6'-dimethoxyphenyl)phenylalanine.

The procedure described in Reference Example 1, Step D was applied to 3 mg of N-(2-(2-aminoethyl)-2-tetrahydrofuroyl)-(L)-4-(2',6'-dimethoxyphenyl) phenylalanine, tert-butyl ester from Step B above to give 3 mg of the title compound.

400 MHz $^1$H NMR (CDCl$_3$) δ 7.34–7.24 (m, 5H); 6.68 (m, 2H); 4.76 (m, 0.5H); 4.60 (m, 0.5H); 3.83 (m, 1H); 3.70 (m, 1H); 3.72 (s, 3H); 3.70 (s, 3H); 3.48 (m, 1H); 3.18 (m, 1H); 3.05–2.86 (m, 1H); 2.38–2.07 (m, 2H); 1.94–1.69 (m, 4H).

The following compound was prepared according to the procedures described in Example 144 substituting N-(2-(3-hydroxypropyl)-2-tetrahydrofuroyl)-(L)-4-(2',6'-dimethoxyphenyl)phenylalanine, tert-butyl ester for N-(2-(2-hydroxyethyl)-2-tetrahydrofuroyl)-(L)-4-(2',6'-dimethoxyphenyl)phenylalanine, tert-butyl ester in Step A:

| Ex. No. | Name | MS* |
|---|---|---|
| 145 | N-(2-(3-Aminopropyl)-2-tetrahydrofuroyl)-(L)-4-(2',6'-dimethoxyphenyl)phenylalanine. | 473 |

EXAMPLE 146

N-(2-Allyl-2-tetrahydrofuroyl)-(L)-4-(2',6 methoxyphenyl)phenylalanine

Step A. 2-Allyl-2-tetrahydrofuroic Acid, Methyl Ester.

The procedure described in Example 137, Step A was applied to 2-tetrahydrofuroic acid, methyl ester and ally bromide to give 5.5 g (56% yield) of the product after flash column chromatography on silica gel eluted with 5:95 ethyl acetate/hexane.

400 MHz $^1$H NMR (CDCl$_3$) δ 5.78 (m, 1H); 5.09 (m, 2H); 3.93 (m, 2H); 3.72 (s, 3H); 2.45 (m, 1H); 2.25 (m, 1H); 1.89 (m, 4H).

Step B. 2-Allyl-2-tetrahydrofuroic Acid.

Base hydrolysis (methanolic sodium hydroxide) of 2-allyl-2-tetrahydrofuroic acid, methyl ester (100 mg, 0.588 mmol) was carried out as described in Example 28, Step B to give 98 mg of the desired acid which was used in the next step without further purification.

Step C. N-(2-Allyl-2-tetrahydrofuroyl)-(L)-4-(2',6'-dimethoxyphenyl)phenylalanine, tert-Butyl Ester.

The procedure described in Example 28, Step A was applied to 98 mg of 2-allyl-2-tetrahydrofuroic acid from step B above to give 204 mg of the desired product after flash column chromatography on silica gel eluted with ethyl acetate/hexane 20:80.

400 MHz $^1$H NMR (CDCl$_3$) δ 7.30–7.64 (m, 5H); 6.65 (d, J=8 Hz, 2H); 5.82–5.69 (m, 1H); 5.13–5.03 (m, 2H); 4.75 (m, 1H); 3.94 (m, 0.5H); 3.71 (s, 6H); 3.65 (m, 0.5H); 3.21 (dd, J=12, 4 Hz, 0.5H); 3.10–3.03 (m, 1.5H); 2.62 (m, 1H); 2.35 (m, 2.18 (m, 0.5H); 1.89–1.81 (m, 2.5H); 1.45 (s, 4.5H); 1.40 (s, 4.5H).

Step D. N-(2-Allyl-2-tetrahydrofuroyl)-(L)-4(2',6'-dimethoxyphenyl)phenylalanine.

The procedure described in Reference Example 1, Step D was applied to 44 mg of N-(2-allyl-2-tetrahydrofuroyl)-(L)-4-(2',6'-dimethoxyphenyl)phenylalanine, tert-butyl ester from Step C above to give 46 mg of the title compound.

400 MHz $^1$H NMR (CDCl$_3$) δ 7.33–7.16 (m, 5H); 6.65 (d, J=8 Hz, 2H); 5.77 (m, 1H); 5.58 (m, 1H); 5.06 (m, 2H); 4.83 (m, 1H); 3.89 (m, 0.5H); 3.72 (s, 6H); 3.55 (m, 0.5H); 3.43 (dd, J=14, 5 Hz, 0.5H); 3.32 (dd, J=14, 5 Hz, 0.5H); 3.16–3.04 (m, 1H); 2.66 (dd, J=6.8, 14 Hz, 0.5H); 2.55 (dd, J=14, 7.6 Hz, 0.5H); 2.40–2.29 (m, 2H); 2.14 (m, 0.5H); 1.89–1.71 (m, 2H); 1.49 (m, 0.5H).

The following compounds were prepared according to the procedures described in Example 146 substituting n-butyl iodide, isopropyl iodide, or isobutyl iodide for allyl bromide in Step A:

| Ex. No. | Name | MS* |
|---|---|---|
| 147 | N-(2-butyl-2-tetrahydrofuroyl)-(L)-4-(2',6'-dimethoxyphenyl)phenylalanine (Isomer A) | 457 |
| 148 | N-(2-butyl-2-tetrahydrofuroyl)-(L)-4-(2',6'-dimethoxyphenyl)phenylalanine (Isomer B) | 457 |
| 149 | N-(2-isopropyl-2-tetrahydrofuroyl)-(L)-4-(2',6'-dimethoxyphenyl)phenylalanine | 443 |
| 150 | N-(2-isobutyl-2-tetrahydrofuroyl)-(L)-4-(2',6'-dimethoxyphenyl)phenylalanine | 457 |

EXAMPLE 151

N-(2-(2-Methylaminoethyl)-2-tetrahydrofuroyl)-(L)-4-(2 ',6'dimethoxyphenyl)phenylalanine Step A. (2-(2-Oxoethyl)-2-tetrahydrofuroic acid, methyl ester.

Ozone was bubbled into a solution of 500 mg (2.94 mmol) of 2-allyl-2-tetrahydrofuroic acid, methyl ester in a 1:1 mixture of dichloromethane/methanol (10 mL) at –78° C. until a light blue color appeared. Excess ozone was removed by passing a stream of nitrogen into the reaction mixture for approximately 10 min. The ozonide was decomposed by addition of dimethylsulfide (1 mL). The reaction mixture was concentrated and the desired product used in the next step without further purification.

Step B. 2-(2-(N-Benzylmethylamino)ethyl)-2-tetrahydrofuroic Acid, Methyl Ester.

The crude, 2-(2-oxoethyl)-2-tetrahydrofuroic acid, methyl ester (1.18 mmol) from Step A above, diisopropyl ethyl amine (0.411 mL, 2.36 mmol) and N-benzylmethylamine (0.152 mL, 1.18 mmol) were combined at room temperature in dichloromethane (10 mL). After stirring for 10 min, it was cooled to 0 °C., NaHB(OAc)₃ (375 mg, 1.77 mmol) was added and it was allowed to warm to room temperature. After stirring over night it was then quenched with NaHCO₃ (sat. 20 mL) and extracted with ethyl acetate (2×25 mL). The combined organic layers was washed with brine, dried over anhydrous MgSO4, filtered, concentrated. The residue was purified on silica gel eluting with 1:2 ethyl acetate/ hexane to give 113 mg of the product.

400 MHz $^1$H NMR (CDCl₃) δ 7.33 (m, 5H); 3.97 (m, 2H); 3.70 (s, 3H); 3.56 (m, 2H); 2.62 (m, 1H); 2.44 (m, 1H); 2.22 (m, 2H); 1.94 (m, 2H); 1.59 (m, 2H).

Step C. 2-(2-(N-benzylmethylamino)ethyl)-2-tetrahydrofuroic Acid.

Base hydrolysis (methanolic sodium hydroxide) of 2-(2-(N-benzyl-methylamino)ethyl)-2-tetrahydrofuroic acid, methyl ester (113 mg, 0.408 mmol) was performed as described in Example 28, Step B to give 100 mg of the corresponding acid which was used in the next step without any further purification.

Step D. N-(2-(2-(N-Benzylmethylamino)ethyl)-2-tetrahydrofuroyl)-(L)-4-(2',6'-dimethoxyphenyl)phenylalanine, tert-Butyl Ester.

The procedure described in Example 28, Step A was applied to 67 mg of 2-(2-(N-benzylmethylamino)ethyl)-2-tetrahydrofuroic acid from Step C above and (L)-4-(2',6'-dimethoxyphenyl)phenylalanine, tert-butyl ester hydrochloride (from Reference Example 26) to give 48 mg of the desired product.

400 MHz $^1$H NMR (CDCl₃) δ 7.30–7.15 (m, 5H); 6.67 (dd, J=8, 2 Hz, 2H); 4.12 (m, 0.5H); 4.57 (m, 0.5H); 3.92 (m, 1H); 3.80 (m, 0.5H); 3.72 (m, 0.5H); 3.71 (s, 6H); 3.65 (s, 6H); 3.65–3.36 (m, 3H); 3.32 (s, 3H); 3.29 (m, 1H); 2.23 (m, 1H); 2.70–2.35 (m, 2H); 2.23–2.17 (m, 2H); 1.93–1.85 (m, 2H); 1.47 (s, 4.5H); 1.43 (s, 4.5H)

Step E. N-(2-(2-methylaminoethyl)-2-tetrahydrofuroyl)-(L)-4(2',6'-dimethoxy-phenyl)phenylalanine, tert-Butyl Ester.

To a solution of 52 mg of N-(2-(2-(N-benzylmethylamino)ethyl)-2-tetrahydrofuroyl)-(L)-4-(2',6'-dimethoxyphenyl)phenylalanine, tert-butyl ester in ethanol (5 mL) was added Pd on carbon (10 mg, 10%). Hydrogenation was carried out under 40 psi of hydrogen overnight. After filtration and removal of the solvents, the residue was purified by preparative TLC eluted with 9:1 dichloromethane: methanol to give 20 mg of the desired product.

400 MHz $^1$H NMR (CD₃OD) δ 7.27–7.15 (m, 5H); 6.70 (dd, J=8, 4 Hz, 2H); 4.64 (m, 1H); 3.93 (m, 2H); 3.83 (m, 0.5H); 3.74 (m, 0.5H); 3.67 (s, 3H); 3.66 (s, 3H); 3.42–3.25 (m, 2H); 3.16 (m, 0.5H); 3.01 (m, 0.5H); 2.42 (s, 1.5H); 2.27 (s, 1.5H); 2.17–2.04 (m, 4H); 1.87 (m, 1H); 1.75 (m, 1H); 1.49 (s, 4.5H); 1.45 (s, 4.5H).

Step F. N-((2-(N-Methyl)-2-amino-ethy)-2-tetrahydrofuroyl)-(L)4-(2',6'-dimethoxyphenyl)phenylalanine.

The procedure described in Reference Example 1, Step D was applied to 20 mg of N-(2-((N-methyl)-2-aminoethyl)-2-tetrahydrofuroyl)-(L)-4-(2',6'dimethoxyphenyl)phenylalanine, tert-butyl ester from Step E above to give 20 mg of the title compound.

400 MHz $^1$H NMR (CD₃OD) δ 8.10 (m, 1H); 7.29–7.17 (m, 5H); 6.70 (m, 2H); 3.93 (m, 1H); 3.76 (m, 0.5H); 3.69 (s, 3H); 3.66 (s, 3H); 3.65 (m, 0.5H); 3.42 (m, 1H); 3.16 (m, 1H); 3.04 (m, 1H); 2.85 (s, 1.5S1); 2.48 (s, 1.5H); 2.72 (m, 1H); 2.10 (m, 1H); 1.90–1.74 (m, 4H).

The following compound was prepared by the procedures described in Example 151 substituting pyrrolidine for N-methyl-benzylamine in Step B:

| Example No. | Name | Mass Spectrum* |
|---|---|---|
| 152 | N-(2-(2-(1-pyrrolidinyl)ethyl)-2-tetrahydrofuroyl)-(L)-4-(2',6'-dimethoxy-4'-(1-pyrrolidinyl)methyl-phenyl)-phenylalanine | 580 |

EXAMPLE 153

N-(2-(Morpholino4-carbonyl)-2-tetrahydrofuroyl)-(L)-4-(2 ',6'dimethoxyphenyl)phenylalanine)

Step A. 2-Benzyloxycarbonyl-2-tetrahydrofuroic Acid, Methyl Ester.

The procedure described in Example 137, Step A was applied to 2-tetrahydrofuroic acid, methyl ester (1.04 g, 8.02 mmol) and benzyl chloroformate (1.7 mL, 12.2 mmol) to give 876 mg of the title compound.

400 MHz $^1$H NMR (CDCl₃) δ 7.34 (m, 5H); 5.23 (d, J=1.3 Hz, 2H); 4.06 (m, 2H); 3.72 (s, 3H); 2.46 (m, 2H); 2.02 (m, 2H).

Step B. 2-Methoxycarbonyl-2-tetrahydrofuroic Acid.

To a solution of 26 mg of 2-benzyloxycarbonyl-2-tetrahydrofuroic acid, methyl ester from Step A above in ethyl acetate (5 mL) was added Pd on carbon (10 mg, 10%). Hydrogenation was carried out under 40 psi of hydrogen for 30 min. It was filtered, concentrated and dried in vacuo. The crude product was used directly in the next reaction without further purification.

Step C. N-(2-Methoxycarbonyl-2-tetrahydrofuroyl)-(L)4-(2',6'-dimethoxy-phenyl)phenylalanine), tert-Butyl Ester.

The method of Example 28, Step A was applied to 40 mg of 2-methoxycarbonyl-2-tetrahydrofuroic acid and 55 mg of (L)-4-(2',6'-dimethoxy-phenyl)phenylalanine, tert-butyl ester hydrochloride (from Reference Example 26) to give 48 mg of the title compound.

400 MHz $^1$H NMR (CDCl₃) δ 7.30–7.18 (m, 5H); 6.65 (m, 2H); 4.77 (m, 1H); 4.04 (m, 1H); 3.93 (m, 0.5H); 3.79 (m, 0.5H); 3.78 (s, 1.5H); 3.77 (s, 1.5H); 3.72 (s, 6H); 3.24–3.11 (m, 2H); 2.70–2.59 (m, 1H); 2.42–2.35 (m, 0.5H); 2.23–2.15 (m, 0 5H); 2.05–1.87 (m, 2H); 1.46 (s, 4.5H); 1.40 (s, 4.5H).

Step D. N-(2-Carboxy-2-tetrahydrofuroyl)-(L)-4-(2',6'-dimethoxyphenyl)phenylalanine), tert-Butyl Ester.

Base hydrolysis (methanolic sodium hydroxide) of N-(2-methoxy-carbonyl-2-tetrahydrofuroyl)-(L)-4-(2',6'-dimethoxyphenyl)phenylalanine), tert-butyl ester (48 mg, 0.0936 mmol) was performed as described in Example 28, Step B to give 43 mg of the corresponding acid which was used in the next step without any further purification.

Step E. N-(2-(Morpholino-4-carbonyl)-2-tetrahydrofuroyl)-(L)-4-(2',6'-dimethoxyphenyl)phenylalanine, tert-Butyl Ester.

The procedure described in Example 28, Step A was applied to 43 mg (0.0982 mmol) of N-(2-carboxy-2-tetrahydrofuroyl)-(L)-4-(2',6'-dimethoxyphenyl)phenylalanine, tert-butyl ester from Step D above, 42 mg of bromotris(dimethyl-amino)phosphonium hexafluorophosphate (in place of PyBOP), and 0.017 mL (0.196 mmol) of morpholine to give 35 mg of the title compound.

400 MHz $^1$H NMR (CDCl₃) δ 7.33–7.27 (m, 2H); 7.24–7.18 (m, 5H); 6.90 (m, 1H); 6.65 (d, J=8 Hz, 1H); 4.83 (m, 0.5H); 4.75 (m, 0.5H); 4.13 (m, 0.5H); 3.96–3.88 (m, 1.5H); 3.73 (s, 1.5H); 3.72 (s, 1.5H); 3.66 (m, 1H); 3.58 (m, 2H); 3.35 (m, 1H); 3.24–3.03 (m, 4H); 1.99 (m, 2H); 1.89 (m, 1H); 1.71 (m, 1H); 1.47 (s, 4.5H); 1.45 (s, 4.5H).

Step F. N-(2-(Morpholino-4-carbonyl)-2-tetrahydrofuroyl)-(L)-4-(2',6'-dimethoxyphenyl)phenylalanine The procedure described of Reference Example 1, Step D was applied to 35 mg of N-(2-(morpholino-4-carbonyl)-2-tetrahydrofuroyl)-(L)-4-(2',6'-dimethoxyphenyl) phenylalanine), tert-butyl ester from Step E above to give 31 mg of the title compound.

400 MHz $^1$H NMR (CDCl$_3$) δ 7.35–7.18 (m, 4H); 7.94 (dd, J=8, 18 Hz, 1H); 6.65 (d, J=8 Hz, 2H); 4.93 (m, 0.5H); 4.93 (m, 0.5H); 4.83 (m, 0.5H); 4.07 (m, 0.5H); 3.95–3.85 (m, 1.5H); 3.75 (s, 3H); 3.73 (s, 3H); 3.68–3.57 (m, 4H); 3.43 (m, 1H); 3.29 (m, 1H); 3.12–3.03 (m, 4H); 1.99 (m, 2H); 2.48 (s, 1.5H); 1.83 (m, 1H); 1.64 (m, 1H).

The following compounds were prepared by the procedures described in Example 153 substituting the appropriate amino acid derivative in Step C and substituting the appropriate amine derivative for morpholine in Step E:

| Example No. | Name | Mass Spectrum* |
|---|---|---|
| 154 | N-(2-benzylaminocarbonyl-2-tetrahydrofuroyl)-(L)-4-(2'-methoxyphenyl)phenylalanine | 503 |
| 155 | N-(2-(N,N-diethylaminocarbonyl)-2-tetrahydrofuroyl)-(L)-4-(2'-methoxyphenyl)phenylalanine (Isomer A) | 469 |
| 156 | N-(2-(N,N-diethylaminocarbonyl)-2-tetrahydrofuroyl)-(L)-4-(2'-methoxyphenyl)phenylalanine (Isomer B) | 469 |
| 157 | N-(2-(N,N-dibenzylaminocarbonyl)-2-tetrahydrofuroyl)-(L)-4-(2'-methoxyphenyl)phenylalanine | 593 |
| 158 | N-(2-(pyrrolidinyl-1-carbonyl)-2-tetrahydrofuroyl)-(L)-4(2'-methoxyphenyl)phenylalanine | 467 |
| 159 | N-(2-(4-morpholino-4-carbonyl)-2-tetrahydrofuroyl)-(L)-4-(2'-methoxyphenyl)phenylalanine | 483 |
| 160 | N-(2-(4-methyl-piperazinyl-1-carbonyl)-2-tetrahydrofuroyl)-(L)-4-(2'-methoxyphenyl)phenylalanine | 496 |

EXAMPLE 161

N(2-(1-Hydroxy-2-methyl-propyl)-2-tetrahydrofuroyl)-L)4-(2',6'-dimethoxy-)phenylalanine).

A. 2-(1-Hydroxy-2-methyl-propyl)-2-tetrahydrofuroic Acid, Methyl Ester

This procedure was adapted from J. Chem. Soc. Perkin Trans. I. 1997, p 771. To a solution of N,N-diisopropylamine (1 mL, 7.69 mmol) in THBF (13 mL) at 0° C. as added n-butyllithium (4.2 mL, 8.46 mmol, 2 M in hexanes). After stirring the mixture for 30 min, it was cooled to –78° C. and 2-tetrahydrofuroic acid, methyl ester (1 g, 7.69 mmol) in THF (13 mL) was added. The reaction mixture was stirred at the same temperature for 15 min and then warmed to –40° C. Isobutyraldehyde (1 mL, 11.5 mmol) was added and stirring was continued for 1 hr and –40° C. The reaction mixture was then warmed to 0° C. and stirred for 1 hr before it was quenched HCl (30 mL, 1M). Extracted with 2×50 mL of ethyl acetate, washed with brine, dried over anhydrous magnesium sulfate. Filtration and evaporation gave the crude product 2.63 g as an oil. Flash column chromatography on silica gel eluted with 15:85 ethyl acetate/hexane gave the desired product (688 mg, 44% yield).

400 MHz $^1$H NMR (CDCl$_3$) δ 4.02 (m, 2H); 3.75 (s, 3H); 3.68 (dd, J=3.7, 10 Hz, 1H); 2.38 (m, 1H); 2.22 (m, 1H); 2.06–1.84 (m, 3H); 1.70 (m, 1H); 0.99 (d,J=6.9 Hz, 3H); 0.96 (d, J=6.9 Hz, 3H).

Step B. 2-(1-Hydroxy-2-methyl-propyl)-2-tetrahydrofuroic Acid.

Base hydrolysis (methanolic sodium hydroxide), 2-(1-hydroxy-2-methyl-propyl)-2-tetrahydrofuroic acid, methyl ester was performed as described in Example 28, Step B to give 250 mg of the desired acid which was used in the next step without further purification.

Step C. N-(2-(1-Hydroxy-3-methyl-propyl)-2-tetrahydrofuroyl)-(L)4-(2',6'-dimethoxyphenyl) phenylalanine, tert-Butyl Ester.

The procedure described in Example 28, Step A was applied to 120 mg (0.636 mmol) of 2-(1-hydroxy-2-methyl-propyl)-2-tetrahydrofuroic acid from Step B and (L)-4-(2',6'-dimethoxyphenyl)phenylalanine, tert-butyl ester hydrochloride (from Reference Example 26) to give 178 mg of the title compound as an oil (53% yield).

400 MHz $^1$H NMR (CDCl$_3$) δ 7.30–7.18 (m, 5H); 6.66 (d, J=8 Hz, 2H); 4.77 (m, 1H); 3.99 (m, 1H); 3.85 (m, 0.5H); 3.72 (s, 6H); 3.71 (s, 3H); 3.70 (m, 1.5H); 3.25 (dd, J=6, 10 Hz, 0.5H); 3.12 (m, 1H); 3.06 (dd, J=8, 10 Hz, 0.5H); 2.32 (m, 1H); 2.22 (m, 1H); 1.86 (m, 2H); 1.73 (m, 1H); 1.46(s, 4.5H); 1.42(s, 4.5H); 0.98 (d, J=6.8 Hz, 3H); 0.931 (d, J=6.8 Hz, 3H).

Step D. N-(2-(1-Hydroxy-3-methyl-propyl)-2-tetrahydrofuroyl)-(L)-4(2',6'-dimethoxyphenyl) phenylalanine.

The procedure described in Reference Example 1, Step D was applied to 15 mg (0.028 mmol) of N-(2-(1-hydroxy-3-methyl-propyl)-2-tetrahydrofuroyl)-(L)-4-(2',6'-dimethoxyphenyl)phenylalanine, tert-butyl ester from Step C above to give 6 mg of the title compound as a faster moving diastereomer after preparative TLC on silica gel eluted with 95:5:0.5 dichloromethane/methanol/acetic acid.

400 MHz $^1$H NMR (CD$_3$OD) δ 7.24–7.14 (m, 5H); 6.68 (d, J=8.8 Hz, 2H); 4.88 (m, 1H); 4.48–4.22 (m, 2H); 3.85 (m, 1H); 3.66 (s, 6H); 3.61 (m, 1H); 3.37 (m, 1H); 3.08 2.18 (m, 1H); 1.81 (m, 2H); 1.70 (m, 1H); 1.42 (m, 1H); 0.928 (d, J=6.8 Hz, 3H); 0.900(d, J=6.8 Hz, 3H).

EXAMPLE 162

N-(2-(1-Methoxy-2-methylpropyl)-2-tetrahydrofuroyl)-(L)-4-(2,6dimethoxyphenyl) phenylalanine).

Step A. N-(2-(1-Methoxy-2-methylpropyl)-2-tetrahydrofuroyl)-(L)-4-(2',6'-dimethoxyphenyl) phenylalanine, tert-Butyl Ester.

At 0° C., to a solution of N-(2-(1-hydroxy-2-methyl-propyl-2-tetrahydrofuroyl)-(L)-4-(2',6'-dimethoxyphenyl) phenylalanine, tert-butyl ester (40 mg, 0.0759 mmol) and 2,6-lutidine (0.043 mL, 0.190 mmol) in dichloromethane was added methyl trifluoromethanesulfonate (0.017 mL, 0.152 mmol). The reaction mixture was allowed to warm to room temperature and stirred overnight. TLC showed no product formation. It was then heated to 40° C. for 6 hr to achieve complete consumption of starting material. It was partitioned between HCl (0.5 N, 20 mL) and ethyl acetate and extracted with ethyl acetate once more. The organic extracts were washed with brine, dried over anhydrous magnesium sulfate, concentrated and dried in vacuo. The crude product was purified by preparative TLC on silica gel eluted with 1:1 ethyl acetate/hexanes to give 15 mg of the title compound.

400 MHz $^1$H NMR (CDCl$_3$) δ 7.30–7.18 (m, 5H); 6.65 (d, J=8 Hz, 2H); 4.75 (m, 1H); 3.94; (m, 2H); 3.71 (s, 6H); 3.66 (m, 1H); 3.56 (s, 1.5H); 3.51 (s, 1.5H); 3.25–3.01 (m, 2H); 2.19 (m, 1H); 2.02–1.75 (m, 2H); 1.52 (m, 1H); 1.45(s, 4.5H); 1.41 (s, 4.5H); 0.95 (m, 6H).

Step B. N-(2-(I-Methoxy-2-methylpropyl)-2-tetrahydrofuroyl)-(L)-4-(2',6'-dimethoxyphenyl) phenylalanine.

The procedure described in Reference Example 1, Step D was applied to 15 mg (0.028 mmol) of N-(2-(1-methoxy-2- methyl-propyl)-2-tetrahydrofuroyl)-(L)-4-(2',6'-dimethoxyphenyl)phenylalanine), tert-butyl ester from Step A above to give 7 mg each of the title compound as a pair of diastereomers after preparative TLC on silica gel eluted with 97.5:2.5:0.25 dichloromethane/methanol/acetic acid. Less polar diastereomer 400 MHz $^1$H NMR (CD$_3$OD) δ 7.32–7.17 (m, 5H); 6.65 (d, J=8.8 Hz, 2H); 4.80 (m, 1H); 3.81 (m, 1H); 3.71 (s, 6H); 3.52 (m, 4H); 3.45 (m, 1H); 3.01 (m, 1H); 3.11 (m, 1H); 2.04 (m, 2H); 1.88 (m, 1H); 1.76 (m, 1H); 1.40 (m, 1H); 0.98(m, 6H). More polar diastereomer 400 MHz $^1$H NMR (CD$_3$OD) δ 7.37–7.17 (m, 5H); 6.65 (d, J=8.8 Hz, 2H); 4.80 (m, 1H); 3.91 (m, 1H); 3.85 (m, 1H); 3.71 (s, 6H); 3.53 (m, 3H); 3.29 (m, 2H); 3.19 (m, 1H); 2.07 (m, 2H); 1.88 (m, 1H); 1.82 (m, 1H); 1.69 (m, 1H); 0.87 (m, 6H).

EXAMPLE 163

N-(2-(1-Oxo-2-Methyl-propyl)-2-tetrahydrofuroyl)-(L)-4-(2',6 '-dimethoxyphenyl)phenylalanine Step A. N-(2-(1-Oxo-2-methyl-propyl)-2-tetrahydrofuroyl)-(L)-4-(2',6'-dimethoxyphenyl)phenylalanine, tert-Butyl Ester.

To a solution of N-(2-(1-hydroxy-2-methyl-propyl)-2-tetrahydrofuroyl)-(L)-4-(2',6'-dimethoxyphenyl)phenylalanine, tert-butyl ester (62 mg, 0.118 mmol), sodium acetate (58 mg, 0.706 mmol) and 4 Å molecular sieves (41 mg) in dichloromethane (1 mL) was added pyridinium chlorochromate (76 mg, 0.353 mmol) at room temperature and stirred overnight. The reaction mixture was partitioned between water and ethyl acetate. The resultant emulsion was filtered through a pad of celite. The organic layer was separated and the aqueous layer was extracted once more with ethyl acetate. The combined organic extracts were washed with brine, dried over anhydrous magnesium sulfate, filtered and concentrated in vacuo. The crude product mixture was purified by preparative TLC on silica gel eluted with 2:1 hexanes/ethyl acetate to give 46 mg of the title compound.

400 MHz $^1$H NMR (CDCl$_3$) δ 7.30–7.18 (m, 5H); 6.65 (d, J=8 Hz, 2H); 4.78 (m, 1H); 4.08 (m, 0.5H); 3.95 (m, 0.5H); 3.84 (m, 1H); 3.72 (s, 6H); 3.44 (m, 0.5H); 3.15–3.01 (m, 2.5H); 2.56 (m, 1H); 2.22 (m, 0.5H); 2.02 (m, 0.5H); 1.90 (m, 1H); 1.75 (m, 1H); 1.46(s, 4.5H); 1.30(s, 4.5H)1.04 (m, 6 H).

Step B. N-(2-(1-Oxo-2-methyl-propyl)-2-tetrahydrofuroyl)-(L)-4-(2',6'-dimethoxyphenyl)phenylalanine.

The procedure described in Reference Example 1, Step D was applied to 46 mg (0.0876 mmol) of N-(2-(1-oxo-2-methyl-propyl)-2-tetrahydrofuroyl)-(L)-4-(2',6'-dimethoxyphenyl)phenylalanine, tert-butyl ester from Step A above to give 19 and 17 mg of the title compounds as a pair of diastereomer after preparative TLC on silica gel eluted with 97.5:2.5:0.25 dichloromethane/methanol/acetic acid three times.

Less polar diastereomer:

400 MHz $^1$H NMR (CD$_3$OD) δ 7.32–7.17 (m, 5H); 6.66 (d, J=8 Hz, 2H); 4.88 (m, 1H); 3.84 (m, 1H); 3.76 (m, 1H); 3.73 (s, 6H); 3.43 (m, 1H); 3.10 (m, 2H); 2.51 (m, 1H); 2.01 (m, 1H); 1.75 (m, 1H); 1.63 (m, 1H); 1.05(m, 6H).

More polar diastereomer:

400 MHz $^1$H NMR (CD$_3$OD) δ 7.32–7.17 (m, 5H); 6.66 (d, J=8 Hz, 2H); 4.88 (m, 1H); 4.01 (m, 1H); 3.93 (m, 1H); 3.72 (s, 6H); 3.33 (m, 1H); 3.17 (m, 1H); 2.97 (m, 1H); 2.52 (m, 1H); 2.26 (m, 1H); 1.87 (m, 2H); 0.97(m, 6H).

EXAMPLE 164

N-(2-Methyl-1,1-dioxo-2-tetrahydrothienoyl)-(L)-4-(2',6'-dihydroxy-phenyl)phenylalanine Step A. N-(2-Methyl-1,1-dioxo-2-tetrahydrothienoyl)-(L)-4-(2',6'-dimethoxy-phenyl)phenylalanine, Methyl Ester.

The method of Example 28, Step A was applied to 45 mg (0.254 mmol) of 2-methyl-1,1-dioxo-tetrahydrothiophene-2-carboxylic acid and (L)-4-(2',6'-dimethoxyphenyl)phenylalanine, methyl ester to give 126 mg (100% yd) of the title compound.

400 MHz $^1$H NMR (CDCl$_3$) δ 7.51 (bd, J=8 Hz, 1H); 7.30–7.18 (m, 4H); 6.66 (d, J=8.4 Hz, 2H); 4.99 (m, 0.5H); 4.99 (m, 0.5H); 4.82 (m, 0.5H); 3.79 (s, 3H); 3.72 (s, 6H); 3.34–2.75 (m, 5H); 2.14 (m, 1H); 1.91 (m, 3H); 1.59(s, 1.5H); 1.45(s, 1.5H).

Step B. N-(2-Methyl-1,1-dioxo-2-tetrahydrothienoyl)-(L)-4-(2',6'-hydroxy-phenyl)phenylalanine.

At −78° C., to a solution of N-(2-methyl-1,1-dioxo-2-tetrahydro-thienoyl)-(L)-4-(2',6'-dimethoxyphenyl)phenylalanine, methyl ester (126 mg, 0.265 mmol) in dichloromethane (3 nL) was added boron tribromide (1.3 mL, 1.32 mmol, 1M/CH$_2$Cl$_2$) dropwise. The reaction mixture was allowed to warm up to 0 ° C. slowly overnight. The ice bath was removed to allow the reaction to warm to room temperature. Water (20 mL) was added and the mixture was stirred for 10 min. It was extracted with ethyl acetate (2×25 mL), washed with brine, dried over anhydrous magnesium sulfate, filtered and concentrated in vacuo to give 108 mg of the title compound.

400 MHz $^1$H NMR (CD$_3$OD) δ 7.88 (bd, J=7.6 Hz, 0.5H); 7.78 (bd, J=7.6 Hz, 0.5H); 7.29–7.22 (m, 5H); 6.93 (t, J=8.4 Hz, 2H); 6.38 (d, J=8.4 Hz, 2H); (m, 2.5H); 2.67–2.55(m, 1H); 2.09–1.91 (m, 4H); 1.54(s, 1.5H); 1.49(s, 1.5H).

EXAMPLE 165

N-(2-(3-Methylamino-propyl)-2-tetrahydrofuroyl)-(L)-4-(2',6'-dimethoxyphenyl)phenylalanine Step A. N-2-(3-Oxo-propyl)-(L)-4-(2',6'-dimethoxyphenyl)phenylalanine, tert-Butyl Ester In the main reaction flask, oxalyl chloride (40 μL, 0.46 mmol) was cooled to −78° C. in (0.6 mL) CH$_2$CL$_2$. A solution of DMSO (49 μL, .67 mmol) in CH$_2$Cl$_2$ (0.6 mL) was added to this solution. After 15 minutes, a solution of N-(2-(3-hydroxypropyl)-2-tetrahydrofuroyl)-(L)-4-(2',6'-dimethoxyphenyl)phenylalanine, tert-butyl ester (120.6 mg, 0.23 mmol) from Example 138 in CH$_2$Cl$_2$ (0.8 mL) was added. The reaction was allowed to stir for one hour at −78° C. TEA (148 μL, 1.1 mmol) was then added and the dry ice/acetone bath removed for one hour. The reaction mixture was then poured into 30 mL H$_2$O, and extracted with EtOAc (2×50 mL). The EtOAc was washed with 0.5N HCl (50 mL), saturated NaHCO$_3$ (50 mL), and brine (50 mL). After drying over anhydrous MgSO$_4$ and concentrating in vacuo, 120 mg of the desired aldehyde was obtained and used in the next step without further purification.

500 MHz $^1$H NMR (CDCl$_3$) δ 9.30 (s, 0.5H); 9.65 (s, 0.5H); 7.30–7.20 (m, 7H); 6.66 (d, J=8.5, 1H); 4.80 (m, 1H); 3.90 (m, 1H); 3.80–3.70 (m, 1H); 3.71 (s, 6H); 3.22–3.10 (m, 1H); 2.40–2.20 (m, 4H); 2.0–1.50 (m, 6H); 1.46 (s, 4.5H); 1.42 (s, 4.5H)

Step B. N-(2-(3-(N-benzyl-N-methyl-amino)propyl)-2-tetrahydrofuroyl)-(L)-4-(2',6'-dimethoxyphenyl)phenylalanine, tert-Butyl Ester The product (60 mg, 0.1 mmol) from the above step was combined with N,N-methyl-benzylamine(12.3 μL, 0.1 mmol) and diisopropylethlyamine (33 μL, 0.19 mmol) in CH$_2$Cl$_2$ (1.3 mL) at room temperature for approximately 15 minutes. The reaction was then cooled to 0° C. and NaBH(OAc)$_3$ (61.6 mg, 0.284 mmol) was added. The reaction was allowed to come to room temperature overnight. Saturated NaHCO$_3$ (50 mL) was added to the reaction mixture and was extracted with EtOAc (2×50 mL). The EtOAc was then washed with brine (30 mL) and dried with NaSO$_4$. The residue was purified by preparative TLC on silica gel eluting with 9:1 methylene chloride/methanol to give 52 mg of the product.

500MHz $^1$H NMR (CDCl$_3$) δ 7.27 (m, 12H); 6.66 (d, J=8.0, 1H); 4.76 (m, 1H); 3.91 (m, 1H); 3.80 (m, 0.5H); 3.71 (s, 6H); 3.62 (m, 0.5H); 3.51 (m, 2H); 3.20 (m, 1H); 3.07 (m, 1H); 2.38 (m, 3H); 2.19 (m, 3.5H); 1.87 (m, 3H); 1.76 (m, 1.5H); 1.57 (m, 4H); 1.46 (s, 4.5H); 1.41 (s, 4.5H)

Step C. N-(2-(3-Methylaminopropyl)-2-tetrahydrofuroyl)-(L)-4-(2',6'-dimethoxyphenyl)phenylalanine, tert-Butyl Ester The procedure described in Example 151, Step E was applied to 51 mg of N-(2-(3-(N-benzyl-N-methyl-amino) propyl)-2-tetrahydrofuroyl)-(L)4-(2',6'-dimethoxyphenyl) phenylalanine, tert-butyl ester to give 32.4 mg of the desired product.

500 MHz $^1$HNMR (CDCl$_3$) δ 7.27 (m, 7H); 6.67 (m, 2H); 4.76 (m, 1H); 3.91 (m, 1H); 3.8 (m, 0.5H); 3.72 (d, J=11.5, 6 h); 3.62 (m, 0.5H); 3.22 (m, 1H); 3.12 (m, 1H); 2.3 (m, 0.5H); 2.16 (m, 0.5H); 2.0–1.7 (m, 10H); 1.58 (m, 4H); 1.46 (s, 4.5H); 1.41 (s 4.5H)

Step D. N-(2-(3-methylaminopropyl)-2-tetrahydrofuroyl)-(L)-4-(2',6'-dimethoxyphenyl)phenylalanine The procedure described in Reference Example 1, Step D was applied to 32 mg of N-(2-(3-methylaminopropyl)-2-tetrahydrofuroyl)-(L)-4-(2',6'-dimethoxy-phenyl) phenylalanine, tert-butyl ester from Step C above to give 29 mg of the title compound.

500 MHz $^1$HNMR (CDCl$_3$) δ 7.32 (m, 7H); 6.67 (m, 2H); 4.70 (m, 1H); 3.79 (m, 1.5H); 3.68 (s, 6H); 3.62 (m, 0.5H); 3.40 (m, 2H); 2.20–1.85 (m, 5H); 1.80–1.30 (m, 10H)

The following compound was prepared by the procedures described in Example 165 substituting dimethylamine for N-methyl-benzyl amine in Step B:

| Example No | Name | Mass Spectrum* |
|---|---|---|
| 166 | N-(2-(3-dimethylaminopropyl)-2-tetrahydrofuroyl)-(L)-4-2',6'-dimethoxyphenyl)phenylalanine | 486 |

EXAMPLE 167

N-(2-(Ethylaminocarbonyl)methyl-2-tetrahydrofuroyl)-(L)-4-(2',6'-dimethoxyphenyl)phenylalanine Step A. 2-(tert-Butoxycarbonyl)methyl)-2-tetrahydrofuroic Acid, Benzyl Ester.

The procedures described in Example 137, Step A with 2-tetrahydrofuroic acid, benzyl ester(1 gm) and substituting tert-butyl bromoacetate (1.1 mL) for 2-tert-butyldimethylsilyloxyethyl iodide were employed to afford the title product (612 mg).

500 MHz $^1$HMNR (CDCl$_3$) δ 7.37 (m, 5H); 5.22 (m, 2H); 4.03 (m, 2H); 2.96 (d, J=16, 1H); 2.73 (d, J=16, 1H); 2.31 (m, 2H); 1.97 (m, 2H); 1.43 (s, 9H)

Step B. 2-(Carboxymethyl)-2-tetrahydrofuroic Acid, Benzyl Ester.

The procedure described in Reference Example 1, Step D was applied to 2-(tert-butoxycarbonyl)methyl)-2-tetrahydrofuroic acid, benzyl ester (290 mg) to afford 309 mg of the title compound.

500 MHz1HNMR (CDCl$_3$) δ 7.36 (m, 5H); 5.23 (m, 2H); 4.09 (m, 2H); 3.11 (d, J=16, 1 h); 2.80 (d, J=16, 1H); 2.31 (m, 1H); 2.02 (m, 3H

Step C. N-(2-((Ethylaminocarbonyl)methyl)-2-tetrahydrofuroic Acid, Benzyl Ester.

The procedure described in Example 28, Step A was applied to 118 mg of 2-(carboxymethyl)-2-tetrahydrofuroic acid, benzyl ester from Step B and ethylamine to give 41.3 mg of the title compound.

500 MHz $^1$HMNR (CDCl$_3$) δ 7.37 (m, 5H); 6.38 (br s, 1H); 5.18 (s, 2H); 4.07 (m, 2H); 3.21 (m, 2H); 2.92 (d, J=15, 1H); 2.65 (d, J=15.5, 11); 2.30 (m, 1 h); 2.00 (m, 3H); 1.07 (t, J=7.5, 3H)

Step D. N-(2-((Ethylaminocarbonyl)methyl)-2-tetrahydrofuroic Acid

The procedure described in Example 137, Step B was applied to 41.3 mg of N-(2-((ethylaminocarbonyl)methyl)-2-tetrahydrofuroic acid, benzyl ester from Step C above to give 32.7 mg of the title compounds.

500 MHZ $^1$HNMR (CDCl$_3$) δ 6.21 (br s, 1H); 4.07 (m, 2H); 3.31 (m, 2H); 2.86 (d, J=15, 1 h); 2.72 (d, J=15, 1H); 2.3 (m, 1H); 2.00 (m, 3H); 1.11 (t, J=7.5, 3H)

Step E. N-(2-((Ethylaminocarbonyl)methyl)-2-tetrahydrofuroyl)-(L)4-(2',6'-dimethoxyphenyl) phenylalanine, tert-Butyl Ester.

The procedure described in Example 28, Step A was applied to 32.7 mg of N-(2-((ethylaminocarbonyl)methyl)-2-tetrahydrofuroic acid and (L)-4-(2',6'-dimethoxyphenyl) phenylalanine, tert-butyl ester to give 40.3 mg of the title compound.

500 MHz $^1$HNMR (CDCl$_3$) δ 7.20 (m, 7H); 6.61 (d, J=8, 2H); 4.70 (m, 1H); 3.93 (m, 1.5H); 3.75 (m, 0.5H); 3.70 (s, 6H); 3.20 (m, 2.5H); 3.1 (m, 1.5H); 2.79 (m, 0.5H); 2.68 (m, 1.5H); 1.80–1.30 (m, 4H); 1.44 (s, 4.5H); 1.39 (s, 4.5H); 1.11 (m, 3H)

Step F. N-(2-((Ethylaminocarbonyl)methyl)-2-tetrahydrofuroyl)-(L)-4-(2',6'-dimethoxyphenyl) phenylalanine.

The procedure described in Reference Example, 1 Step D was applied to 40.3 mg of N-(2-((ethylaminocarbonyl) methyl)-2-tetrahydrofuroyl)-(L)-4-(2',6'-dimethoxyphenyl) phenylalanine, tert-butyl ester from Step E above to give 11 mg of the title compound.

500 MHz $^1$HNMR (CD$_3$OD) δ 7.25 (m, 7H); 6.67 (m, 2H); 4.80 (m, 1H); 3.80 (m, 2H); 3.64 (s, 6H); 3.34–3.17 (m, 4H); 2.78–2.25 (m, 2H); 2.20 (m, 0.5H); 2.10–1.70 (M, 3.5H); 1.11 (m, 3H)

The following compound was prepared by the procedures described in Example 167substituting morpholine for ethylamine in Step C:

| Example No, | Name | Mass Spectrum |
|---|---|---|
| 168 | N-(2-((4-morpholino-carbonyl)methyl)-2-tetrahydro-furoyl)-(L)-4-(2',6'-dimethoxyphenyl)phenylalanine | 528 |

EXAMPLE 169

N-(2-(3-Acetamidopropyl)-2-tetrahydrofuroyl)-(L)-4-(2',6'-dimethoxyphenyl)phenylalanine Step A. N-(2-(3-Acetamidopropyl)-2-tetrahydrofuroyl)-(L)-4-(2',6'-dimethoxyphenyl)phenylalanine, tert-butyl ester.

The tert-butl ester of Example 145 (34 mg) was treated with equal portions of acetic anhydride and TEA at room temperature according to the procedures described in Example 139, Step A to form the title compound (30.3 mg).

500 MHz $^1$HMNR (CDCl$_3$) δ 7.30 (m, 7H); 6.67 (m, 2H); 4.81 (m, 0.5H); 4.75 (m, 0.5H): 3.8 (m, 1.5H); 3.70 (s, 6H);

3.62 (m, 0.5H); 3.3–3.0 (m, 4H); 2.3 (m, 2.19 (m, 0.5H); 2.0–1.7 (m, 6H); 1.6–1.3 (m, 4H); 1.49 (s, 9H)

Step B. N-(2-(3-Acetamidopropyl)-2-tetrahydrofuroyl)-(L)-4-(2',6'-dimethoxyphenyl)phenylalanine The procedure described in Reference Example 1, Step D was applied to 30.3 mg of N-(2-(3-acetamidopropyl)-2-tetrahydrofuroyl)-(L)4-(2',6'-dimethoxy-phenyl)phenylalanine, tert-butyl ester to give 19.7 of the title compound.

500MHz $\delta^1$HNMR (CDCl$_3$) $\delta$ 7.26 (m, 7H); 6.69 (m, 2H): 4.70 (m, 1H); 3.89 (m, 20 1.5H); 3.76 (m, 0.5H); 3.66 (s, 6H); 3.30 (m, 2H); 3.12 (m,2H); 2.20 (m, 0.5H); 1.91–1.78 (m, 6.5H); 1.46 (m, 3H); 1.19 (m, 1H)

The following compound was prepared from the tert-butyl ester from Example 165, Step C by the procedures described in Example 169:

| Example No, | Name | Mass Spectrum |
|---|---|---|
| 170 | N-(2-(3-(N-methylacetamido)-propyl)-2-tetrahydrofuroyl)-(L)-4-(2',6'-dimethoxyphenyl)phenylalanine | 514 |

The following compounds were prepared from the appropriately substituted 2-tetrahydrofuroic acid derivative (described in Reference Examples 14, 27–31) and (L)-4-(2',6'-dimethoxyphenyl)phenylalanine, tert-butyl ester from Reference Example 26 or (L)-4-(2',6'-dichlorobenzoylamino)phenylalanine, methyll ester from Reference Example 31 by the coupling procedures described in Example 28, Step A. The tert-butyl ester was hydrolyzed by the procedure described in Reference Example 1, Step D.

| Example No, | Name | Mass Spectrum |
|---|---|---|
| 171 | N-(2-cyclohexane-2-tetrahydrofuroyl)-(L)-4-(2',6'-dimethoxyphenyl)phenylalanine (Isomer A) | 452.3 |
| 172 | N-(2-cyclohexane-2-tetrahydrofuroyl)-(L)-4-(2',6'-dimethoxyphenyl)phenylalanine (Isomer B) | 452.4 |
| 173 | N-(2-(3-nitro-4-chlorophenyl)-2-tetrahydrofuroyl)-(L)-4-(2',6'-dimethoxyphenyl)phenylalanine | 555.27 |
| 174 | N-(2-(3-nitrophenyl)-2-tetrahydrofuroyl)-(L)-4-(2',6'-dimethoxyphenyl)phenylalanine (Isomer A) | 521.19 |
| 175 | N-(2-(3-nitrophenyl)-2-tetrahydrofuroyl)-(L)-4-(2',6'-dimethoxyphenyl)phenylalanine (Isomer B) | 521.18 |
| 176 | N-(2-(4-methoxyphenyl)-2-tetrahydrofuroyl)-(L)-4-(2',6'-dimethoxyphenyl)phenylalanine | 506.2 |
| 177 | N-(2-(3,5-dimethoxyphenyl)-2-tetrahydrofuroyl)-(L)-4-(2',6'-dimethoxyphenyl)phenylalanine | 536.2 |
| 178 | N-(2-(4-benzoxazole)-2-tetrahydrofuroyl)-(L)-4-(2',6'-dimethoxyphenyl)phenylalanine | 517.11 |
| 179 | N-(2-(4-methyl-2-thiazole)-2-tetrahydrofuroyl)-(L)-4-(2',6'-dimethoxyphenyl)phenylalanine | 497.12 |

EXAMPLE 180

N-(2-methyl-1,1-dioxo-2-tetrahydrothienoyl)-(L)-4-((4-tert-butoxycarbonyl)-1-piperzinylcarbonyl)phenylalanine The title compound was prepared according to the procedures described in Example 28, Steps A and B from 2-methyl-1,1-dioxo-tetrahydrothiophene-2-carboxylic acid (Reference Example 15) and (L)4-((tert-carbonyl)-piperazinyl-carbonyl)-phenylalanine (Reference Example 32). Mass spectrum: m/e=454.3 (M$^+$).

EXAMPLE 181

N-(2(R)-Methyl-2-tetrahydrofuroyl)-(L)-4-(2,6-dimethoxy-4-((4-tert-butoxycarbonyl-piperazin-1-yl)methyl)phenyl)phenylalanine Step A. N-(2(R)-Methyl-2-tetrahydrofuroyl)-)-4-(2,6-dimethoxy-4-((4-tert-butoxycarbonylpiperazin-1-yl)methyl)phenyl)phenylalanine, Methyl Ester To 152 mg (0.292 mmol) of N-(2(R)-methyl-2-tetrahydrofuroyl)-(L)-(4-(2,6-dimethoxy-4-bromomethyl)phenyl)phenylalanine, methyl ester (from Reference Example 34, Step C) dissolved in 5 mL CH$_2$Cl$_2$, 71 mg (0.379 mmol) of tert-butyl-1-piperazinecarboxylate and 41 $\mu$L (0.350 mmol) of 2,6-lutidine were added. The reaction mixture was stirred overnight. The reaction mixture was concentrated in vacuo and the residue was purified by preparative TLC on silica gel eluted with 2% CH$_3$OH in CH$_2$Cl$_2$ to give 153.1 mg of the desired product. MS m/e=626.4 (M+H$^+$)

Step B. N-(2(R)-Methyl-2-tetrahydrofuroyl)-(L)-4-(2,6-dimethoxy-4-((4-tert-butoxycarbonylpiperazin-1-yl)methyl)phenyl)phenylalanine.

To 150 mg (0.239 mmol) of N-(2(R)-methyl-2-tetrahydrofuroyl)-(L) 4-(2,6-dimethoxy-4-((4-tert-butoxycarbonylpiperazin-1-yl)methyl)phenyl)phenylalanine, methyl ester in 5 mL of CH$_3$OH was treated with 623 $\mu$L (0.311 mmol) of 0.5 N NaOH. The mixture was stirred overnight. The mixture was acidified with 5% citric acid (pH=2–3). The mixture was extracted with ethyl acetate (3×). The organic layer was washed with brine and dried over MgSO$_4$. The mixture was filtered and concentrated in vacuo and the residue was purified by preparative TLC on silica gel eluted with 1% AcOH, 5% CH$_3$OH in CH$_2$Cl$_2$ to give 101.2 mg of the desired product.

MS m/e=612.38 (+H$^+$) 500 MHz $^1$H NMR (CD$_3$OD): $\delta$ 1.26 (s, 3H); 1.45 (s, 9H); 1.74 (m, 3H); 2.24 (m, 1H); 2.70 (m, 4H); 3.10 (m, 1H); 3.28 (m, 1H); 3.51 (m, 4H); 3.65 (m, 10H); 3.77 (m, 2H); 3.88 (m, 1H); 6.73 (s, 2H); 7.10 (m, 2H); 7.16 (m, 2H).

EXAMPLE 182

N-(2(R)-Methyl-2-tetrahydrofuroyl)-(L)-4-(2,6-dimethoxy-4-(piperazinylmethyl hydrochloride)phenyl)phenylalanine To 96.2 mg (0.157 mmol) of N-(2(R)-methyl-2-tetrahydrofuroyl)-(L)-4-(2,6-dimethoxy-4-((4-tert-butoxycarbonylpiperazinylmethyl))phenyl)phenylalanine (from Example 181, Step B) dissolved in 2.5 mL of ethyl acetate, 1.96 mL (7.86 mmol) of HCl (4.0 M in ethyl acetate) was added. The mixture was stirred for three hours. The mixture was concentrated in vacuo to afford a quantitative yield of the desired product.

MS m/e=548.37 (M+H$^+$) 500 MHz $^1$H NMR (CD$_3$OD): $\delta$ 1.23 (s, 3H); 1.79 (m, 3H); 2.24 (m, 1H); 3.10 (m, 1H); 3.28 (m, 1H); 3.63 (m, 8H); 3.74 (s, 6H); 3.87 (m, 2H); 4.47 (s, 2H); 4.69 (m, 1H); 7.00 (m, 2H); 7.13 (m, 2H); 7.19 (m, 2H).

EXAMPLE 183

N-(2(R)-Methyl-2-tetrahydrofuroyl)-(L)-4-(2,6-dimethoxy-4-(4-methyl-1-piperidinyl-methyl))phenyl)phenylalanine Step A. N-(2(R)-Methyl-2-tetrahydrofuroyl)-(L)-4-(2.6-dimethoxy-4-(4-methyl-1-piperidinylmethyl)phenyl)phenylalanine, Methyl Ester To 106.7 mg (0.205 mmol) of N-(2(R)-methyl-2-tetrahydrofuroyl)-(L)-4-(2,6-dimethoxy-4-(bromomethyl)

phenyl)phenylalanine, methyl ester (from Reference Example 34, Step C) dissolved in 5 mL of CH$_2$Cl$_2$, 31.8 μL (0.287 mmol) of 1-methylpiperazine and 13 mg (0.102 mmol) of 4-(dimethylamino)pyridine (DMAP) were added. The reaction mixture was stirred for four hours. The reaction mixture was concentrated in vacuo and the residue was purified by preparative TLC on silica gel elued with 5% CH$_3$OH in CH$_2$Cl$_2$ to give 68 mg of the desired product. MS m/e=540.39 (M+H$^+$)

Step B. N-(2(R)-Methyl-2-tetrahydrofuroyl)-(L)-4-(2,6-dimethoxy-4-((4-methylpiperidinylmethyl))phenyl)phenylalanine To 64 mg (0.118 mmol) of N-(2(R)-methyl-2-tetrahydrofuroyl)-(L)-4-(2,6-dimethoxy-4-((4-methylpiperidinylmethyl))phenyl)phenylalanine, methyl ester dissolved in 5 mL of CH$_3$OH, 356 μL (0.178 mmol) of 0.5 N NaOH was added. The mixture was stirred overnight. The mixture was quenched with a few drops of acetic acid. The mixture was concentrated in vacuo and the residue was purified by preparative TLC on silica gel eluted with 2:1 v:v 10% CH$_3$OH/CH$_2$Cl$_2$:4% NH$_4$OH/CH$_3$OH to give 57.1 mg of the desired product.

MS m/e=526.5 (M+H$^+$) 500 MHz $^1$H NMR (CD$_3$OD): δ 1.30 (s, 3H); 1.75 (m, 3H); 2.26 (m, 1H); 2.61 (s, 3H); 2.68 (m, 4H); 2.93 (m, 4H); 3.08 (dd, 1H); 3.22 (dd, 1H); 3.61 (s, 6H); 3.63 (s, 2H); 3.90 (m, 2H); 4.50 (m, 1H); 6.66 (m, 2H); 7.07 (d, 2H, J=7.80); 7.16 (, 2H, J=8.10).

EXAMPLE 184

N-(2(R)-Methyl-2-tetrahydrofuroyl)-(L)-4-(2,4-dimethoxy-5-pyrimidinyl)-phenylalanine Coupling of 200 mg (0.479 mmol) of N-(2(R)-methyl-2-tetrahydrofuroyl)-(L)-4-iodophenylalanine, methyl ester (from Example 111, Step B) with 106 mg (0.575 mmol) of 2,4-dimethoxypyrimidine-5-boronic acid mediated by Pd(PPh$_3$)$_4$ was carried out as described in Reference Example 2, Step B. The reaction was acidified with a few drops of saturated HCl in ethyl acetate. The solvents were removed in vacuo and the residue was purified by preparative TLC on silica gel eluted with 1% AcOH in 5% CH$_3$OH/CH$_2$Cl$_2$ to give 167.8 mg of the desired product.

MS m/e=416.22 (M+H$^+$) 500 MHz $^1$H NMR (CD$_3$OD): δ 1.24 (s, 3H); 1.70–1.90 (m, 3H), 2.22 (m, 1H), 3.11 (m, 1H); 3.27 (m, 1H); 3.88 (m, 2H); 4.01 (m, 6H); 4.68 (brs, 1H); 7.25 (d, 2J=8.00); 7.41 (d, 2H, J=8.00); 8.11 (bd, 1H); 8.22 (brs, 1H).

EXAMPLE 185

N-(2(R)-Methyl-2-tetrahydrofuroyl)-(L)-4-(2,6-dimethoxy-4-(1 ,2,4-triazol-1-yl-methyl)phenyl)phenylalanine Step A. N-(2(R)-Methyl-2-tetrahydrofuroyl)-(L)-4-(2,6-dimethoxy-4-(1,2,4-triazol-1-yl-methyl)phenyl)phenylalanine, methyl ester To 246 mg (0.472 mmol) of N-(2(R)-methyl-2-tetrahydrofuroyl)-(L)-4-(2,6-dimethoxy-4-(bromomethyl)phenyl)phenylalanine, methyl ester (from Reference Example 34, Step C) dissolved in 5 mL of DMF and 2.5 mL of CH$_2$Cl$_2$, 65 mg (0.708 mmol) of 1,2,4-triazole sodium salt was added. The reaction mixture was stirred for two hours. The reaction mixture was concentrated in vacuo and the residue was purified by preparative TLC on silica gel eluted with 3% CH$_3$OH/CH$_2$Cl$_2$ to give 195 mg of the desired product.

MS m/e=509.32 (M+H$^+$)

Step B. N-(2(R)-Methyl-2-tetrahydrofuroyl)-(L)-4-(2,6-dimethoxy-4-(1,2,4-triazol-1-yl-methyl)phenyl)phenylalanine To 190 mg (0.373 mmol) of N-(2(R)-methyl-2-tetrahydrofuroyl)-(L)-4-(2,6-dimethoxy-4-((1,2,4-triazol-1-yl-methyl))phenyl)phenylalanine, methyl ester dissolved in 5 mL of methanol, 1.12 mL (0.560 mmol) of 0.5 N NaOH was added. The mixture was stirred for four hours. The mixture was quenched with a few drops of 10% citric acid. The mixture was concentrated in vacuo and the residue was purified by preparative TLC o silica gel eluted with 1% AcOH in 5% CH$_3$OH/CH$_2$Cl$_2$, to give 140.1 mg of the desired product.

MS m/e=495.31 (M+H$^+$) 500 MHz $^1$H NMR (CD$_3$OD): δ 1.24 (s, 3H); 1.73 (m, 1H); 1.82 (m, 2H); 2.23 (m, 1H); 3.10 (m, 1H); 3.26 (m, 1H); 3.63 (s, 6H), 3.86 (m, 2H); 4.67 (brs, 1H); 2H); 6.66 (s, 2H); 7.10 (d, 2H, J=7.60); 7.16 (d, 2H, J=7.50); 8.04 (brs, 1H); 8.61 (brs, 1H).

EXAMPLE 186

N-(2(R)-Methyl-2-tetrahydrofuroyl)-(L)-4-(2,6-dimethoxy-(4-((4-tert-butoxycarbonyl-1-piperazinocarbonyloxy)methyl))phenyl)phenylalanine Step A. N-(2(R)-Methyl-2-tetrahydrofuroyl)-(L)-4-(2,6-dimethoxy-4-((4-nitrophenyloxycarbonyloxymethyl))phenyl)phenylalanine, Methyl Ester To 362 mg (0.791 mmol) of N-(2(R)-methyl-2-tetrahydrofuroyl)-(L)-4-(2,6-dimethoxy-4-(hydroxymethyl)phenyl)phenylalanine, methyl ester (from Reference Example 34, Step B) dissolved in 2.5 mL of CH$_2$Cl$_2$ and 2.5 mL of THF, 167.4 mg (0.831 mmol) of 4-nitrophenyl chloroformate and 96 μL (1.18 mmol) of pyridine were added. The reaction mixture was stirred for five hours. The mixture was concentrated in vacuo and the residue was purified by preparative TLC on silica gel eluted with 50% hexanes/ethyl acetate to give 399 mg of the desired product.

MS m/e=623.30 (M+H$^+$)

Step B. N-(2(R)-Methyl-2-tetrahydrofuroyl)-(L)-4-(2,6-dimethoxy-4-((4-tert-butoxycarbonyl-1-piperazinocarbonyloxymethyl))phenyl)phenylalanine, Methyl Ester N-(2(R)-Methyl-2-tetrahydrofuroyl)-(L)-4-(2,6-dimethoxy-4-((4-nitrophenyloxycarbonyloxymethyl))phenyl)phenylalanine, methyl ester and tert-butyl-1-piperazinecarboxylate were coupled according to the procedure described in example 28, Step A. The product was purified by preparative TLC on silica gel eluted with 50% hexanes/ethyl acetate to afford 159.9 mg of the desired product. MS m/e=670.3(M+H$^+$)

Step C. N-(2(R)-Methyl-2-tetrahydrofuroyl)-(L)-4-(2,6-dimethoxy-4-((4-tert-butoxycarbonyl-1-piperazinocarbonyloxymethyl))phenyl)phenylalanine N-(2(R)-Methyl-2-tetrahydrofuroyl)-(L)-4-(2,6-dimethoxy-4-((4-tert-butoxycarbonyl-1-piperazinocarbonyloxymethyl))phenyl)phenylalanine, methyl ester was hydrolyzed according to the procedure described in example 185, Step B. The product was purified by preparative TLC on silica gel eluted with CH$_2$Cl$_2$:CH$_3$OH:AcOH to afford 145.4 mg of the desired product.

MS m/e=656.43 (M+H$^+$); 500 MHz $^1$H NMR (CD$_3$OD): δ 1.24 (s, 3H); 1.45 (s, 9H); 1.74 (m, 1H); 1.83 (m, 2H); 2.24; (m, 1H); 3.11 (m, 1H); 3.28 (m, 1H); 3.43–3.49 (m, 8H); 3.66 (s,6H); 3.87 (m, 2H); 4.67 (m, 1H); 5.14 (s, 2H); 6.70 (s, 2H); 7.14 (m, 4H).

EXAMPLE 187

N-(2(R)-Methyl-2-tetrahydrofuroyl)-(L)-4-(2,6-dimethoxy-4-(piperazinylcarbonyloxy-methyl)phenyl)phenylalanine, Hydrochloride The t-Boc protecting group of N-(2(R)-methyl-2-tetrahydrofuroyl)-(L)-4-(2,6-dimethoxy-4-((4-tertbutoxycarbonyl-(piperazinylcarbonyloxymethyl))phenyl) phenylalanine (from Example 186, Step C) was removed according to the procedure described in Example 182 to give a quantitative yield of the desired product.

MS m/e=556.38 (M+H$^+$); 500 MHz $^1$H NMR (CD$_3$OD): δ 1.24 (s, 3H); 1.73 (m, 1H); 1.83 (m, 2H); 2.24 (m, 1H); 3.10 (m, 1H); 3.23 (m, 5H); 3.67 (s, 6H); 3.76 (brs, 4H); 3.87 (m, 2H); 1H); 5.17 (s, 2H); 6.73 (s, 2H); 7.15 (m, 4H).

The following compounds were prepared according to the procedure described in the Example 186, Steps B and C substituting the appropriate amine derivative in Step B for 4-Boc-piperazine:

| Example No. | Name | MS* |
|---|---|---|
| 188 | N-(2(R)-Methyl-2-tetrahydrofuroyl)-(L)-4-(2,6-dimethoxy-4-(1-pyrrolidinyl-carbonyloxymethyl)phenyl)-phenylalanine | 541.31 |
| 189 | N-(2(R)-Methyl-2-tetrahydrofuroyl)-(L)-4-(2,6-dimethoxy-4-(dimethylamino-carbonyloxymethyl)phenyl)-phenylalanine | 515.37 |

*Mass spectrum (M + H$^+$)

EXAMPLE 190

N-(2(R)-Methyl-2-tetrahydrofuroyl)-(L)-4-(2,6-dimethoxy-4-(1-pyrrolidinylmethyl)-phenyl) phenylalanine Step A. N-(Boc)-(L)-4-(2.6-dimethoxy-4-(tert-butyldiphenylsilyloxymethyl) phenyl)phenylalanine, tert-Butyl Ester N-(Boc)-(L)-4-iodophenylalanine, tert-butyl ester (from Example 104, Step A) was coupled with 3,5-dimethoxy-4-((tert-butyldiphenylsilyl)oxymethyl)-phenylboronic acid (from Reference example 33) in the presence of Pd(PPh$_3$)$_4$ as described in reference example 2, Step B to provide 2.9 g of the desired product after flash column chromatography on silica gel eluted with 3–10% hexanes/ethyl acetate.

500 MHz $^1$H NMR (CD$_3$OD): δ 1.10 (s, 9H); 1.39–1.42 (m, 18H); 2.98 (m, 2H); 3.60 (s, 6H); 4.26 (m, 1H); 4.81 (s, 2H); 6.64 (s, 2H); 7.17 (m, 3H); 7.39 (m, 8H); 7.70 (m, 4H).

Step B. (L)-4-(2,6-dimethoxy-4-(tert-butyldiphenylsilyloxymethyl)phenyl) phenylalanine, tert-butyl ester hydrochloride To 2.87 g (3.95 mmol) of N-(Boc)-(L)-4-(2,6-dimethoxy-4-(tert-butyldiphenylsilyloxy methyl)phenyl)phenylalanine, tert-butyl ester in 10 mL ethyl acetate cooled to 0° C., 7.0 nL of HCl (4 M in ethyl acetate) was added drop-wise over three hours. The mixture was warmed to room temperature and stirred for two hours. The mixture was concentrated in vacuo to give a quantitative yield of the desired product.

MS m/e=626.42 (M+H$^+$).

Step C. N-(2(R)-Methyl-2-tetrahydrofuroyl)-(L)-4-(2,6-dimethoxy-4-(tert-butyldiphenylsilyloxymethyl)phenyl) phenylalanine, tert-Butyl Ester 2(R)-Methyl tetrahydrofuran -2-carboxylic acid (from Reference Example 10 and (L)-4-(2,6-dimethoxy-4-(tert-butyldiphenylsilyloxymethyl)phenyl) phenylalanine, tert-butyl ester hydrochloride were coupled according to the procedure of example 28, Step A. The product was purifed by flash column chromatography on silica gel eluted with 25% hexanes/ethyl acetate to afford 750 mg of the desired product.

MS m/e=738.58 (M+H$^+$).

Step D. N-(2(R)-Methyl-2-tetrahydrofuroyl)-(L)-4-(2,6-dimethoxy-4-(hydroxymethyl)phenyl)phenylalanine, tert-Butyl Ester N-(2(R)-Methyl-2-tetrahydrofuroyl)-(L)-4-(2,6-dimethoxy-4-(tert-butyldiphenylsilyloxy methyl)phenyl) phenylalanine, tert-butyl ester was deprotected according to the procedure described in reference example 34, Step B to give 461.2 mg of the desired product.

MS m/e=500.42 (M+H$^+$).

Step E. N-(2(R)-Methyl-2-tetrahydrofuroyl)-(L)-4-(2,6-dimethoxy-4-(bromo methyl)phenyl)phenylalanine, tert-Butyl Ester N-(2(R)-Methyl-2-tetrahydrofuroyl)-(L)-4-(2,6-dimethoxy-4-(hydroxymethyl)phenyl)phenylalanine, tert-butyl ester was reacted with Ph$_3$PBr$_2$ according to the procedure described in reference example 2, Step C. After flash chromatography eluting with 25% hexanes/ethyl acetate gave 111 mg of the desired product.

MS m/e=564.40 (M+H$^+$).

Step F. N-(2(R)-Methyl-2-tetrahydrofuroyl)-()-4-(2,6-dimethoxy-4-(pyrrolidinylmethyl)phenyl)phenylalanine, tert-Butyl Ester N-(2(R)-Methyl-2-tetrahydrofuroyl)-(L)-4-(2,6-dimethoxy-4-(bromomethyl)phenyl) phenylalanine, tert-butyl ester and pyrrolidine were coupled according to the procedure described in Example 181, Step A to yield 48.5 mg of the desired product.

MS m/e=553.65 (M+H$^+$).

Step G. N-(2(R)-Methyl-2-tetrahydrofuroyl)-(L)-4-(2,6-dimethoxy-4-(pyrrolidinylmethyl)phenyl)phenylalanine To 45.5 mg (0.0823 mmol) of N-(2(R)-methyl-2-tetrahydrofuroyl)-(L)-4-(2,6-dimethoxy-4-(pyrrolidinylmethyl)phenyl)phenylalanine, tert-butyl ester dissolved in 5 mL of CH$_2$Cl$_2$, 253 μL (3.29 mmol) of trifluoroacetic acid was added. The reaction mixture was stirred overnight. The mixture was concentrated in vacuo to give a quantitative yield of the desired product.

MS m/e=497.46 (M+H$^+$); 500 MHz $^1$H NMR (CD$_3$OD): δ 1.23 (s, 3H); 1.73 (m, 1H); 1.84 (m, 2H); 2.05 (m, 2H); 2.21 (m, 3H); 3.10 (m, 1H); 3.24 (m, 3H); 3.55 (m, 2H); 3.72 (s, 6H); 3.88 (t, 2H); 4.37 (s, 2H); 4.70 (m, 1H); 6.84 (s, 2H); 7.12 (d, 2H, J=8.20); 7.19 (d, 2H, J=8.20); 7.82 (d, 1H, J=8.70).

The following compound was prepared according to the procedure described in Example 190 substituting morpholine for pyrrolidine in Step F.

| Example No. | Name | MS* |
|---|---|---|
| 191 | N-(2(R)-Methyl-2-tetrahydrofuroyl)-(L)-4-(2,6-dimethoxy-4-(morpholinylmethyl)phenyl)-phenylalanine | 513.42 |

*Mass spectrum, m/e (M + H$^+$)

EXAMPLE 192

N-(2(R)-Methyl-2-tetrahydrofuroyl -(L)-4-(2,6-dimethoxy-4-(aminomethyl)phenyl)phenylalanine Step A. N-(2(R)-Methyl-2-tetrahydrofuroyl)-(L)-4-(2,6-dimethoxy-4-(methyl azide)phenyl)phenylalanine, tert-Butyl Ester To 100 mg (0.018 mmol) of N-(2(R)-methyl-2-tetrahydrofuroyl)-(L)-4-(2,6-dimethoxy-4-(bromomethyl) phenyl)phenylalanine, tert-butyl ester (from Example 190, Step F) dissolved in 3 mL of DMF, 17.3 mg (0.267 mmol) of sodium azide was added. The mixture was stirred for 48 hours. The mixture was concentrated in vacuo and the residue was purified by preparative TLC on silica gel eluted with 50% hexanes/ethyl acetate to give 81 mg of the desired product.

MS m/e=525.26 (M+H$^+$).

Step B. N-(2(R)-Methyl-2-tetrahydrofuroyl)-(L)-4-(2,6-dimethoxy-4-(amino methyl)phenyl]phenylalanine, tert-Butyl Ester To 78 mg (0.148 mmol) of N-(2(R)-methyl-2-tetrahydrofuroyl)-(L)-4-(2,6-dimethoxy-4-(methylazide) phenyl)phenylalanine, tert-butyl ester dissolved in 2.5 mL of THF, 40 mg of triphenylphosphine was added over 10 minutes. The mixture was stirred for two hours. 4 µL (0.223 mmol) of H$_2$O was added, and the mixture was stirred overnight. The mixture was concentrated in vacuo and the residue was purified by preparative TLC on silica gel eluted with 10% CH$_3$OH/CH$_2$Cl$_2$ to afford 63 mg of the desired product.

MS m/e=499.6 (M+H$^+$).

Step C. N-(2(R)-Methyl-2-tetrahydrofuroyl)-(L)-4-(2,6dimethoxy-4-(amino methyl)phenyl)phenylalanine N-(2(R)-Methyl-2-tetrahydrofuroyl)-(L)-4-(2,6-dimethoxy-4-(aminomethyl)phenyl)phenylalanine, tert-butyl ester was hydrolyzed according to the procedure described in reference example 190, Step G. The residue was purified by preparative TLC on silica gel eluted with 20% CH$_3$OH/CH$_2$Cl$_2$ to afford 33.6 mg of the desired product.

MS m/e=443.23 (M+H$^+$); 500 MHz $^1$H NMR (CD$_3$OD): δ 1.24 (s, 3H); 1.67–1.87 (m, 3H); 2.22 (m, 1H); 3.10 (brs, 1H); 3.30 (m, 1H); 3.70 (s, 6H); 3.88 (m, 2H); 4.12 (s, 2H); 6.79 (s, 2H); 7.11–7.18 (m, 4H).

EXAMPLE 193

N-(2-(4-Chlorophenyl)-2-tetrahydrofuroyl)-(L)-4-(2,6-dimethoxy-4-(pyrrolidinyl-methyl)phenyl)phenylalanine Step A. N-(2-(4-Chlorophenyl)-2-tetrahydrofuroyl)-(L)-4-(2,6-dimethoxy-4-(tert-butyldiphenylsilyloxymethyl)phenyl)phenylalanine, tert-Butyl Ester 2-(4-Chlorophenyl)-2-tetrahydrofuroic acid (from Reference Example 14) and (L)-4-(2,6-dimethoxy-4-(tert-butyldiphenylsilyloxymethyl)phenyl) phenylalanine, tert-butyl ester hydrochloride (from Example 190, Step B) were coupled according to the procedure of Example 28, Step A. The product was purified by flash column chromatography on silica gel eluted with 12.5% hexanes/ethyl acetate to afford 974 mg of the desired.

500 MHz $^1$H NMR (CDCl$_3$): δ 1.15 (s, 9H); 1.42(d, 9H); 1.71–1.85 (m, 1H); 1.91–2.14 (m, 2H); 2.71–2.87 (m, 1H); 2.95–3.26 (m, 3H); 3.68 (d, 6H); 3.81–3.96 (m, 1H); 4.02–4.10 (m, 1H); 4.66 (m, 1H); 4.83 (s, 2H); 6.66 (s, 2H); 6.95 (d, 1H); 7.19 (m, 2H); 7.27–7.55 (m, 12H); 7.73–7.75 (m, 4H).

Step B. N-(2-(4-Chlorophenyl)-2-tetrahydrofuroyl)-(L)-4-(2,6-dimethoxy-4-(hydroxymethyl)phenyl)phenylalanine, tert-Butyl Ester N-(2-(4-Chlorophenyl)-2-tetrahydrofuroyl)-(L)-4-(2,6-dimethoxy-4-(tert-butyldiphenylsilyloxymethyl)phenyl) phenylalanine, tert-butyl ester was reacted with tetrabutyammonium fluoride according to the procedure described in Reference Example 34, Step B to give 378.5 mg of the desired product.

MS m/e=596.1 (M+H$^+$).

Step C. N-(2-(4-Chlorophenyl)-2-tetrahydrofuroyl)-(L)-4-(2,6-dimethoxy-4-(bromomethyl)phenyl)phenylalanine, tert-Butyl Ester N-(2-(4-Chlorophenyl)-2-tetrahydrofuroyl)-(L)-4-(2,6-dimethoxy-4-(hydroxymethyl) phenyl)phenylalanine, tert-butyl ester was reacted according to the procedure described in Reference Example 34, Step C to give 105 mg of the desired product.

MS m/e=661.6 (M+H$^+$).

Step D. N-(2-(4-Chlorophenyl)-2-tetrahydrofuroyl)-(L)-4-(2,6-dimethoxy-4-(pyrrolidinylmethyl)phenyl)phenylalanine, tert-Butyl Ester N-(2-(4-Chlorophenyl)-2-tetrahydrofuroyl)-(L)-4-(2,6-dimethoxy-4-(bromomethyl) phenyl)phenylalanine, tert-butyl ester and pyrrolidine were coupled according to the procedure described in Example 181, Step A to give 80.7 mg of the desired product.

MS m/e=649.50 (M+H$^+$).

Step E. N-(2-(4-Chlorophenyl)-2-tetrahydrofuroyl)-(L)-4-(2,6-dimethoxy-4-(pyrrolidinylmethyl)phenyl)phenylalanine N-(2-(4-Chlorophenyl)-2-tetrahydrofuroyl)-(L)-4-(2,6-dimethoxy-4-(pyrrolidinylmethyl)phenyl)phenylalanine, tert-butyl ester was hydrolyzed according to the procedure described in Example 181, Step B to give a quantitative yield of the desired product.

MS m/e=593.32 (M+H$^+$); 500 MHz $^1$H NMR (CD$_3$OD): δ 1.57 (m, 1H); 1.90–2.10 (m, 4H); 2.21 (m, 2H); 2.52 (m, 1H); 3.05 (m, 1H); 3.17–3.25 (m, 2H); 3.34 (m, 1H); 3.56 (m, 2H); 3.73 (d, 6H); 3.81–4.09 (m, 2H); 4.38 (d, 2H); 4.65 (m, 1H); 6.86 (m, 2H); 6.93–7.00 (m, 2H); 7.13–7.28 (m, 4H); 7.36–7.50 (m, 2H); 7.99–8.07 (m, 1H).

EXAMPLE 194

N-(2-(4-Chlorophenyl)-2-tetrahydrofuroyl)-(L)-4-(2,6-dimethoxy-4-(1,2,4-triazolylmethyl)phenyl)phenylalanine Step A. N-(2-(4-Chlorophenyl)-2-tetrahydrofuroyl)-(L)-4-(2,6-dimethoxy-4-(1,2,4-triazolylmethyl)phenyl)phenylalanine, tert-Butyl Ester N-(2-(4-Chlorophenyl)-2-tetrahydrofuroyl)-(L)-4-(2,6-dimethoxy-4-(bromomethyl) phenyl)phenylalanine, tert-butyl ester (from Example 193, Step C) and 1,2,4-triazole sodium salt were coupled according to the procedure described in Example 185, Step A to give 91 mg of the desired product.

MS m/e=647.6 (M+H$^+$);

Step B. N-(2-(4-Chlorophenyl)-2-tetrahydrofuroyl)-L)-4-(2,6-dimethoxy-4-(1,2,4-triazolylmethyl)phenyllphenylalanine.

N-(2-(4-Chlorophenyl)-2-tetrahydrofuroyl)-(L)-4-(2,6-dimethoxy-4-(1,2,4-triazolylmethyl)phenyl)phenylalanine, tert-butyl ester was hydrolyzed according to the procedure described in reference example 190, Step G to give a quantitative yield of the desired product which was purified by preparative TLC on silica gel eluted with 1%AcOH in 5% CH$_3$OH/CH$_2$Cl$_2$ with multiple-elutions to isolate the two diastereomers (34.5 mg and 29.3 mg).

Less polar diastereomer:
MS m/e=591.4 (M+H$^+$);
500 MHz $^1$H NMR (CD$_3$OD): δ 1.59 (m, 1H); 1.74 (m, 1H); 2.01 (m, 1H); 2.52 (m, 1H); 3.05 (m, 1H); 3.32 (m, 1H); 3.64 (s, 6H); 3.77 (m, 1H); 3.85 (m,1H); 4.65 (brs, 1H); 5.41 (s, 2H); 6.67 (s, 2H); 7.13 (m, 4H); 7.24 (d, 2H, J=8.20); 7.47 (d, 2H, J=8.30); 8.02 (m, 2H); 8.58 (brs, 1H).

More polar diastereomer:
MS m/e=591.4 (M+H$^+$); 500 MHz $^1$H NMR (CD$_3$OD): δ 1.89 (m, 2H); 2.05 (m, 1H); 2.71 (m, 1H); 3.05 (m, 1H); 3.13 (m, 1H); 3.63 (s, 6H); 3.95 (m, 1H); 4.04 (m, 1H); 4.60 (brs, 1H); 5.42 (s, 2H); 6.67 (s, 2H); 6.89 (m, 2H); 6.96 (m, 2H); 7.20 (d, 2H, J=8.50); 7.36 (d, 2H, J=8.50); 7.92 (brs, 1H); 8.02 (brs, 1H); 8.58 (brs, 1H).

EXAMPLE 195

N-(2-(4-Chlorophenyl)-2-tetrahydrofuroyl)-(L)-4-(2,6-dimethoxy-4-(hydroxymethl)-phenyl)phenylalanine N-(2-(4-Chlorophenyl)-2-tetrahydrofuroyl)-(L)-4-(2,6-dimethoxy-4-(hydroxymethyl)phenyl)phenylalanine, tert-butyl ester (from Example 193, Step B) was hydrolyzed according to the procedure described in Example 104, Step D. The residue was purified by preparative TLC on silica gel eluted with 1%AcOH in 5% CH$_3$OHICH$_2$Cl$_2$ with multiple-elutions to isolate the two diastereomers (10 mg and 12 mg). Less polar diastereomer:

MS m/e=540.4 (M+H$^+$); 500 MHz $^1$H NMR (CD$_3$OD): δ 1.60 (m, 1H); 1.74 (m, 1H); 2.00 (m, 1H); 2.52 (m, 1H); 3.07 (brs, 2H); 3.67 (s, 6H); 3.77 (m, 1H); 3.86 (m, 1H); 4.62 (s, 2H); 4.85 (brs, 1H); 6.70 (s, 2H); 7.14–7.25 (m, 6H); 7.48 (d, 2H).

More polar diastereomer:

MS m/e=540.4 (M+H$^+$); 500 MHz $^1$H NMR (CD$_3$OD): δ 1.88 (brs, 2H); 2.08 (m, 1H); 2.70 (m, 1H); 3.15 (m, 2H); 3.66 (s, 6H); 3.96 (m, 1H); 4.05 (brs, 1H); 4.63 (s, 2H); 4.89 (m, 1H); 6.71 (s, 2H); 6.88 (brs, 2H); 6.99 (brs, 2H); 7.22 (d, 2H, J=8.20); 7.37 (d, 2H, J=8.20).

EXAMPLE 196

N-(2-(4-Chlorophenyl)-2-tetrahydrofuroyl)-(L)-4-(2,6-dimethoxy-4-(methoxymethyl)phenyl) phenylalanine Step A. N-(2-(4-Chlorophenyl)-2-tetrahydrofuroyl)-(L)-4-(2,6-dimethoxy-4-(methoxymethyl)phenyl)phenylalanine, tert-butyl ester To 167 mg (0.280 mmol) of N-(2-(4-chlorophenyl)-2-tetrahydrofuroyl)-(L)-4-(2,6-dimethoxy-4-(hydroxymethyl) phenyl)phenylalanine, tert-butyl ester (from Example 193, Step B) in 10 mL of CH$_2$Cl$_2$ cooled to 0° C., 52 μL of tetrafluoroboric acid and 280 μL (3.36 mmol) of (trimethylsilyl)diazomethane (2.0 M in hexanes) were added. The mixture was warmed to room temperature and stirred for four hours. The mixture was concentrated in vacuo, and the residue was purified by preparative TLC on silica gel eluted with 2/1 hexanes/ethyl acetate to give 92.5 mg of the desired product.

MS m/e=610.26 (M+H$^+$);

Step B. N-(2-(4-Chlorophenyl)-2-tetrahydrofuroyl)-(L)-4-(2,6-dimethoxy-4-(methoxymethyl)phenyl)phenylalanine N-(2-(4-Chlorophenyl)-2-tetrahydrofuroyl)-(L)-4-(2,6-dimethoxy-4-(methoxymethyl)phenyl)phenylalanine, tert-butyl ester was hydrolyzed according to the procedure described in Example 190, Step G to give a quantitative yield of the desired product.

MS m/e=554.32 (M+H$^+$); 500 MHz $^1$H NMR (CD$_3$OD): δ 1.62 (m, 1H); 1.94–2.10 (m, 2H); 2.49–2.71 (m, 1H); 3.03–3.17 (m, 2H); 3.42 (d, 3H); 3.68 (d, 6H); 3.78–4.08 (m, 2H); 4.48 (d, 2H); 4.62–4.69(m, 1H); 6.69 (m, 2H); 6.92 (m, 1H); 7.01 (m, 1H); 7.16 (m, 2H); 7.24 (m, 7.37 (m, 1H); 7.48 (m, 1H).

EXAMPLE 197

N-(2-(4-Chlorophenyl)-2-tetrahydrofuroyl)-(L)-4-(2,6-dimethoxy-4-(N,N-dimethyl-aminocarbonyloxymethyl)phenyl)phenylalanine Step A. N-(2-(4-Chlorophenyl)-2-tetrahydrofuroyl)-(L)-4-(2,6-dimethoxy-4-(4-nitrophenyloxycarbonyloxymethyl) phenyl)phenylalanine, tert-Butyl Ester N-(2-(4-Chlorophenyl)-2-tetrahydrofuroyl)-(L)-4-(2,6-dimethoxy-4-(hydroxymethyl) phenyl)phenylalanine, tert-butyl ester (from Example 193, Step B) was reacted with nitrophenylchloroformate according to the procedure described in Example 186, Step A to give a quantitative yield of the desired product.

MS m/e=761.30 (M+H$^+$).

Step B. N-(2-(4-Chlorophenyl)-2-tetrahydrofuroyl)-(L)-4-(2,6-dimethoxy-4-(N,N-dimethylaminocarbonyloxymethyl) phenyl)phenylalanine, tert-Butyl Ester To 170 mg (0.223 mmol) of N-(2-(4-chlorophenyl)-2-tetrahydro-furoyl)-(L)-4-(2,6-dimethoxy-4-(4-nitrophenyloxycarbonyloxymethyl)phenyl)phenylalanine, tert-butyl ester in 5 mL of CH$_2$Cl$_2$, 27 mg (0.335 mmol) of N,N-dimethylamine hydrochloride, 52 μL of 2,6-lutidine, and 14 mg of DMAP were added. The mixture was stirred for 48 hours. The mixture was concentrated in vacuo and the residue was purified by preparative TLC on silica gel eluted with 50% hexanes/ethyl acetate to give 130 mg of the desired product.

MS m/e=667.5 (M+H$^+$).

Step C. N-(2-(4-Chlorophenyl)-2-tetrahydrofuroyl)-(L)-4-(2,6-dimethoxy-4-(N,N-dimethylaminocarbonyloxymethyl) phenyl)phenylalanine N-(2-(4-Chlorophenyl)-2-tetrahydrofuroyl)-(L)-4-(2,6-dimethoxy-4-(N,N-dimethylaminocarbonyloxymethyl) phenyl)phenylalanine, tert-butyl ester was hydrolyzed according to the procedure described in Example 190, Step G to give 88 mg of the desired product.

MS m/e=611.17 (M+H$^+$); 500 MHz $^1$H NMR (CD$_3$OD): δ 1.53–1.74 (m, 1H); 1.89–2.11 (m, 2H); 2.53–2.71 (m, 1H); 2.93 (d, 61); 3.04–3.16 (m, 2H); 3.68 (d, 6H); 3.79–4.07 (m, 2H); 4.63 (m, 1H); 5.11 (d, 2H); 6.72 (m, 2H); 6.91 (d, 1H); 7.00 (d, 1M); 7.15 (m, 2H); 7.26 (m, 2H); 7.38 (m, 1H); 7.48 (m, 1H); 7.94–8.01 (m, 1H).

EXAMPLE 198

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 mg/ml) for 2 hours at room temperature and washed twice with phosphate buffered saline (PBS). The albumin coating was next derivatized with 10 mg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 mg/ml and allowed to react for 2 hours at room temperature. The plates were washed twice with PBS and stored at 4∞ C.

Step B. Preparation of Fluorescently Labeled Jurkat Cells.

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 mg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of 2×10$^6$ cells/ml in PBS containing a 1 mM concentration of a fluorogenic esterase substrate (2',7'-bis-(2-carboxyethyl)-5-(and -6)-carboxyfluorescein, acetoxymethyl ester; BCECF-AM; Molecular Probes Inc., Eugene, Oregon; catalog #B-1150) for 30–60 minutes at 37∞ C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C. Assay Procedure.

Compounds of this invention were prepared in DMSO at 100× the desired final assay concentration. Final concentrations were selected from a range between 0.001 nM–100 mM. Three mL of diluted compound, or vehicle alone, were premixed with 300 mL of cell suspension in 96-well polystyrene plates with round bottom wells. 100 mL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 199

Antagonism of VLA4 Dependent Binding to VCAM-Ig Fusion Protein

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAAT-TCTT ACAGCCTGCC-3';

5'-PCR primer:
5'-ATAGGAATTCCAGCTGCCACCATGCCTGGGAA-GATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:

MPGKMVVILGASNILW MFAASQAFKIETTPESRY-LAQIGDSVSLTCSTTGCES PFFSWRTQID-SPLNGKVTNEGTTSTLTMNPVSFGNEH-SYLCTATCESRKLEKGI QVEIYSFPKDPEIHSGPLEAGK-PITVKCSVADVYPFDRLEIDLLKGDHLMKSQ EFLEDADRKSLETKSLEVTFT-PVIEDIGKVLVCRAKLHIDEMDSVPTVRQAVK EL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neoNVCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B. Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C. VCAM-IG Binding Assay.

Compounds of this invention were prepared in DMSO at 100× the desired final assay concentration. Final concentrations were selected from a range between 0.001 nM–100 μM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration~100 pM); (iii) 2.5 μL of compound solution or DMSO; (iv) and 0.5×10$^6$ cells in a volume of 30 mL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 200

Antagonism of $\alpha_4\beta_7$ Dependent Binding to VCAM-Ig Fusion Protein

Step A. $\alpha_4\beta_7$ Cell line.

RPMI-8866 cells (a human B cell line $\alpha_4^+\beta_1^-\beta_7^+$; a gift from Prof. John Wilkins, University of Manitoba, Canada)

were grown in RPMI/10% fetal calf serum/100 U penicillin/ 100 μg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step B. VCAM-Ig Binding Assay.

Compounds of this invention were prepared in DMSO at 100× the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 ml/well of binding buffer containing 1.5 mM $MnCl_2$; (ii) 10 ml/well $^{125}$I-VCAM-Ig in binding buffer (final assay concentration <500 pM); (iii) 1.5 ml/well test compound or DMSO alone; (iv) 38 ml/well RPMI-8866 cell suspension ($1.25×10^6$ cells/ well). The plates were incubated at room temperature for 45 minutes on a plate shaker at 200 rpm, filtered on a vacuum box, and washed on the same apparatus by the addition of 100 mL of binding buffer containing 1 mM $MnCl_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1. A method for the treatment of diseases, disorders, conditions or symptoms mediated by cell adhesion in a mammal which comprises administering to said mammal an effective amount of a compound of Formula I:

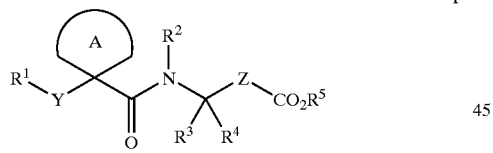

I or a pharmaceutically acceptable salt thereof wherein:

A is a 5-membered monocyclic saturated heterocyclic ring having one O, wherein said heterocyclic ling is optionally substituted with one to four substituents independently selected from oxo, methylene and $R^b$;

Y is 1) a bond,
2) $C_{1-10}$alkylene,
3) $C_{2-10}$alkenylene,
4) $C_{2-10}$alkynylene,
wherein said alkylene, alkenylene and alkynylene are each optionally substituted with one to four substituents selected from $R^a$, Z is 1) a bond, or
2) —C($R^5$)($R^6$)—

$R^1$ is 1) hydrogen,
2) Cy,
3) $OR^5$,
4) $OC(O)R^5$;
5) $OC(O)OR^5$,
6) $OC(O)NR^dR^e$,
7) $SR^5$,
8) $S(O)_mR^5$,
9) $SO_2NR^dR^e$,
10) $C(O)R^5$,
11) $C(O)OR^5$,
12) $C(O)NR^dR^e$,
13) $NR^dR^e$,
14) $NR^dC(O)R^5$,
15) $NR^dC(O)OR^5$,
16) $NR^dC(O)NR^dR^e$,
17) $NR^dSO_2R^5$;
wherein Cy is optionally substituted with one to four substituents independently selected from $R^b$;

$R^2$ is 1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^3$ is 1) $C_{1-10}$alkyl,
2) $Ar^1$,
3) $C_{1-10}$alkyl-$Ar^1$,
4) $Ar^1$—$Ar^2$,
5) $C_{1-10}$alkyl-$Ar^1$—$Ar^2$,
wherein the alkyl group is optionally substituted with one to four substituents selected from $R^a$, and $Ar^1$ and $Ar^2$ are optionally substituted with one to four substituents independently selected from $R^b$, $R^4$ is 1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^5$ is 1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
wherein alkyl, alkenyl and alkynyl are optionally substituted with one to four substituents selected from $R^a$, and Cy is optionally substituted with one to four substituents independently selected from $R^b$;

$R^6$ is 1) hydrogen,
2) a group selected from $R^b$;

$R^a$ is 1) —$OR^d$,
2) $NR^dS(O)_mR^e$,
3) —N2,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$, 18) —OC(O)NR$^d$R$^e$,
19) —NR$^d$C(O)OR$^e$,
20) —NR$^d$C(O)NR$^d$R$^e$,
21) —CR$^d$(N—OR$^e$),
22) CF$_3$,
23) —OCF$_3$,
24) C$_{3-8}$cycloalkyl, or
25) heterocyclyl;
   wherein cycloalkyl and heterocyclyl are optionally substituted with one to four groups independently selected from oxo and R$^c$;
R$^b$ is 1) a group selected from R$^a$,
2) C$_{1-10}$ alkyl,
3) C$_{2-10}$ alkenyl,
4) C$_{2-10}$ alkynyl,
5) Ar$^1$,
6) C$_{1-10}$alky- Ar$^1$,
   wherein alkyl, alkenyl, alkynyl, and Ar$^1$ are optionally substituted with one to four substituents selected from a group independently selected from R$^a$;
R$^c$ is 1) halogen,
2) NR$^f$R$^g$,
3) C(O)OR$^f$,
4) C$_{1-4}$alkyl,
5) C$_{1-4}$alkoxy,
6) aryl,
7) aryl C$_{1-4}$alkyl,
8) hydroxy,
9) CF$_3$,
10) OC(O)C$_{1-4}$alkyl,
11) OC(O)NR$^f$R$^g$,
12) NR$^j$C(O)R$^g$,
13) NR$^j$SO$_2$R$^g$, or
14) aryloxy;
R$^d$ and R$^e$ are independently selected from hydrogen, C$_{1-10}$alkyl,
C$_{2-10}$alkenyl, C$_{2-10}$alkynyl, Cy and Cy C$_{1-10}$alkyl, wherein alkyl, alkenyl, alkynyl and Cy are optionally substituted with one to four substituents independently selected from R$^c$; or
R$^d$ and R$^e$ together with the atom(s) to which they are attached form a heterocyclic ring of 4 to 7 members containing 0–2 additional heteroatoms independently selected from oxygen, sulfur and N—R$^h$;
R$^f$ and R$^g$ are independently selected from hydrogen, C$_{1-10}$alkyl, Cy and Cy—C$_{1-10}$alkyl; or
R$^f$ and R$^g$ together with the carbon to which they are attached form a ring of 5 to 7 members containing 0–2 heteroatoms independently selected from oxygen, sulfur and N—R$^h$;
R$^h$ is hydrogen, C$_{1-10}$alkyl, or C(O)OC$_{1-10}$alkyl;
Cy is selected from cycloalkyl, heterocyclyl and Ar$^1$;
Ar$^1$ and Ar$^2$ are independently selected from aryl and heteroaryl;
m is 1 or 2;
n is an integer from 1 to 10.

2. The method of claim 1 wherein said disease or disorder is selected from asthma, allergic rhinitis, multiple sclerosis, atherosclerosis, and inflammatory bowel disease.

3. A a pharmaceutical composition which comprises a compound of formula I as defined in claim 1 and a pharmaceutically acceptable carrier.

4. A compound having the formula I

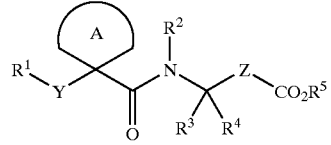

I or a pharmaceutically acceptable salt thereof wherein:
A is a 5-membered monocyclic saturated heterocyclic ring having one O, wherein said heterocyclic ring is optionally substituted with one to four substituents independently selected from oxo, methylene and R$^b$;
Y is 1) a bond,
2) C$_{1-10}$alkylene,
3) C$_{2-10}$alkenylene,
4) C$_{2-10}$alkynylene,
   wherein said alkylene, alkenylene and alkynylene are each optionally substituted with one to four substituents selected from R$^a$,
Z is 1) a bond, or
2) —C(R$^5$)(R$^6$)—
R$^1$ is 1) hydrogen,
2) Cy,
3) OR$^5$,
4) OC(O)R$^5$;
5) OC(O)OR$^5$,
6) OC(O)NR$^d$R$^e$,
7) SR$^5$,
8) S(O)$_m$R$^5$,
9) SO$_2$NR$^d$R$^e$,
10) C(O)R$^5$,
11) C(O)OR$^5$,
12) C(O)NR$^d$R$^e$,
13) NR$^d$R$^e$,
14) NR$^d$C(O)R$^5$,
15) NR$^d$C(O)OR$^5$,
16) NR$^d$C(O)NR$^d$R$^e$,
17) NR$^d$SO$_2$R$^5$;
   wherein Cy is optionally substituted with one to four substituents independently selected from R$^b$;
R$^2$ is 1) hydrogen,
2) C$_{1-10}$alkyl,
3) C$_{2-10}$alkenyl,
4) C$_{2-10}$alkynyl,wherein alkyl, alkenyl and alkynyl are optionally substituted with one to four substituents independently selected from R$^a$;
R$^3$ is 1) C$_{1-10}$alkyl,
2) Ar$^1$,
3) C$_{1-10}$alkyl-Ar$^1$,
4) Ar$^1$—Ar$^2$,
5) C$_{1-10}$alkyl-Ar$^1$—Ar$^2$,
   wherein the alkyl group is optionally substituted with one to four substituents selected from R$^a$, and Ar$^1$ and Ar$^2$ are optionally substituted with one to four substituents independently selected from R$^b$,
R$^4$ is 1) hydrogen,
2) C$_{1-10}$alkyl,
3) C$_{2-10}$alkenyl,
4) C$_{2-10}$alkynyl, wherein alkyl, alkenyl and alkynyl are optionally substituted with one to four substituents independently selected from R$^a$; R$^5$ is 1) hydrogen,
2) C$_{1-10}$alkyl,
3) C$_{2-10}$alkenyl, 4) $C_{2-10}$alkynyl,
5) Cy,
6) Cy—$C_{1-10}$alkyl,
wherein alkyl, alkenyl and alkynyl are optionally substituted with one to four substituents selected from $R^a$, and Cy is optionally substituted with one to four substituents independently selected from $R^b$;

$R^6$ is 1) hydrogen,
2) a group selected from $R^b$;

$R^a$ is 1) —$OR^d$,
2) $NR^dS(O)_mR^e$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N$—$OR^e)$,
22) $CF_3$,
23) —$OCF_3$,
24) $C_{3-8}$cycloalkyl, or
25) heterocyclyl;
wherein cycloalkyl and heterocyclyl are optionally substituted with one to four groups independently selected from oxo and $R^c$;

$R^b$ is 1) a group selected from $R^a$,
2) $C_{1-10}$ alkyl,
3) $C_{2-10}$ alkenyl,
4) $C_{2-10}$ alkynyl,
5) $Ar^1$,
6) $C_{1-10}$alky—$Ar^1$,
wherein alkyl, alkenyl, alkynyl, and $Ar^1$ are optionally substituted with one to four substituents selected from a group independently selected from $R^a$;

$R^c$ is 1) halogen,
2) $NR^fR^g$,
3) $C(O)OR^f$,
4) $C_{1-4}$alkyl,
5) $C_{1-4}$alkoxy,
6) aryl,
7) aryl $C_{1-4}$alkyl,
8) hydroxy,
9) $CF_3$,
10) $OC(O)C_{1-4}$alkyl,
11) $OC(O)NR^fR^g$,
12) $NR^fC(O)R^g$,
13) $NR^fSO_2R^g$, or
14) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0–2 additional heteroatoms independently selected from oxygen, sulfur and N—$R^h$;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 5 to 7 members containing 0–2 heteroatoms independently selected from oxygen, sulfur and N—$R^h$;

$R^h$ is hydrogen, $C_{1-10}$alkyl, or $C(O)OC_{1-10}$alkyl;

Cy is selected from cycloalkyl, heterocyclyl and $Ar^1$;

$Ar^1$ and $Ar^2$ are independently selected from aryl and heteroaryl;

m is 1 or 2;

n is an integer from 1 to 10;

with the proviso that when $R^1$-Y-X represents H, $R^4$ is H, and $R^3$ is (1) optionally substituted $C_{1-10}$alkyl, (2) phenyl unsubstituited or substituted with methyl, hydroxy, or methoxy, or (3) benzyl unsubstituted or substituted with methyl, hydroxy, or benzyl, then $R^5$ is hydrogen, or a pharmaceutically acceptable salt thereof.

5. A compound of claim 4 wherein A is tetrahydrofuran optionally substituted with one to four groups selected from oxo and a group selected from $C_{1-10}$alky, $Ar^1$, $Ar^1$—$C_{1-10}$alkyl, $C_{1-10}$alkoxy, halogen, —$S(O)_2R^d$, —$S(O)_2NR^dR^e$, —$NR^dR^e$, —$O(CR^fR^g)_nNR^dR^e$, and —$C(O)NR^dR^e$.

6. A compound of claim 4 wherein A is selected from tetrahydrofuran-2-yl, 5-oxo-tetrahydrofuran-2-yl, 4-methyltetrahydrofuran-2-yl, 4-methylenetetrahydrofuran-2-yl, 4-hydroxymethyl-tetrahydrofuran-2-yl, 4-(pyrrolidinecarbonylmethyl)tetrahydrofuran-2-yl, 4-[(benzoylamino)methyl]tetrahydrofuran-2-yl, 4-[(benzenesulfonylamino)methyl]tetrahydrofuran-2-yl, 3-oxo-5-methyltetrahydrofuran-2-yl, 3-oxo-5-benzyltetrahydrofuran-2-yl, 3-oxo-5-phenyltetrahydrofuran-2-yl, 3-hydroxy-5-phenyltetrahydrofuran-2-yl, 5-methyl-3-[(4-methoxy)phenyl]tetrahydrofuran-2-yl, 5-methyl-3-aminotetrahydrofuran-2-yl, 4-(1-pyrrolidinyl)tetrahydrofuran-2-yl, tetrahydrofuran-3-yl and 2,2-dimethyl-5-oxo-tetrahydrofuran-3-yl.

7. A compound of claim 4 wherein A is 2-tetrahydrofuranyl.

8. A compound of claim 4 wherein Y is a bond or $C_{1-5}$alkylene optionally substituted with one to two groups selected from $R^a$.

9. A compound of claim 4 wherein $R^1$ is H, Cy optionally substituted with one to four substituents selected from $R^b$, $OR^5$, $OC(O)R^5$, $NR^dR^e$, $C(O)NR^dR^e$, $C(O)OR^5$, $C(O)NR^dR^e$, $NR^dC(O)R^5$.

10. A compound of claim 4 wherein $R^3$ is $C_{1-5}$alkyl-$Ar^1$ or $C_{1-5}$alkyl-$Ar^1$—$Ar^2$, wherein $Ar^1$ and $Ar^2$ are optionally substituted with one to four groups independently selected from $R^b$.

11. A compound of claim 4 wherein $R^3$ is $C_{1-3}$alkyl-$Ar^1$—$Ar^2$ optionally substituted with one to four groups independently selected from $R^b$.

12. A compound of claim 4 wherein $R^3$ is $CH_2$—$Ar^1$—$Ar^2$ wherein at least one Ar is a phenyl, and wherein $Ar^1$ and $Ar^2$ are substituted with one to three groups selected from $R^b$.

13. A compound of claim/wherein $R^3$ is substituted biphenylmethyl wherein the substituent is one to three groups selected from $R^b$, and one of the substituent is located at the 2'-position of the biphenyl ring.

14. A compound of claim 4 having the formula Ia:

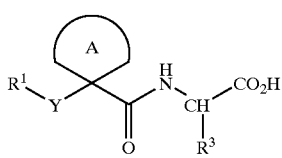

or a pharmaceutically acceptable salt thereof, wherein
A is a 5-membered monocyclic saturated heterocyclic ring having one O, optionally substituted with one to four substituents independently selected from oxo and $R^b$;
Y is (1) a bond, or
  (2) $C_{1-5}$alkylene optionally substituted with one to four groups independently selected from $R^a$;
$R^1$ is (1) H,
  (2) Cy optionally substituted with one to four substituents independently selected from $R^b$;
  (3) $OR^5$,
  (4) $OC(O)R^5$,
  (4) $OC(O)NR^dR^e$,
  (5) $NR^dR^e$,
  (6) $NR^dC(O)R^5$,
  (7) $C(O)R^5$,
  (8) $C(O)OR^5$,
  (9) $C(O)NR^dR^e$;
$R^3$ is 1) $C_{1-10}$alkyl,
  2) $Ar^1$,
  3) $C_{1-10}$alkyl-$Ar^1$,
  4) $Ar^1$—$Ar^2$,
  5) $C_{1-10}$alkyl-$Ar^1$—$Ar^2$,
    wherein the alkyl group is optionally substituted with one to four substituents selected from $R^a$, and $Ar^1$ and $Ar^2$ are optionally substituted with one to four substituents independently selected from $R^b$,
$R^1$, $R^3$, $R^5$, $R^a$, $R^b$, $R^d$, $R^e$, $Ar^1$ and $Ar^2$ are as defined in claim 4.

15. A compound of claim 16 having the formula Ib:

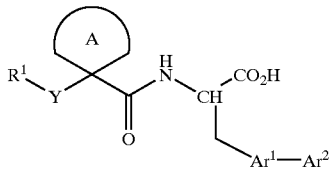

or a pharmaceutically acceptable salt thereof, wherein A, Y $R^1$, Ar1 and Ar2 are as defined in claim 14.

16. A compound of claim 15 wherein A is tetrahydrofuranyl optionally substituted with one or two groups independently selected from $C_{1-5}$alkyl, $CH_2OC(O)NR^dR^e$, $CH_2NR^dC(O)R^e$, $CH_2NR^dSO2R^e$, $CH_2OR^d$, $CH_2$—$Ar^1$ (where $Ar^1$ is optionally substituted with one to two groups selected from $R^a$), $NR^dR^e$, $OR^d$ and oxo.

17. A compound of claim 15 wherein Y- $R^1$ is hydrogen, $C_{1-5}$alkyl, phenyl optionally substituted with one to three groups selected from $R^a$, $C_{1-5}$alkylene-$R^1$ (where $R^1$ is hydroxy, $C_{1-5}$alkoxy, $C_{1-5}$alkanoyloxy, $NR^dR^e$, $C(O)NR^dR^e$, $NR^dC(O)C_{1-5}$alkyl, or phenyl optionally substituted with one to three groups selected from $R^b$), $C(O)NR^dR^e$, $C(O)OR^5$, $C(O)R^5$.

18. A compound of claim 15 wherein $Ar^1$—$Ar^2$ is biphenyl optionally substituted with one to two groups selected from $R^b$.

19. A compound of claim 15 wherein

A is 2-tetrahydrofuranyl optionally substituted with one or two groups independently selected from $C_{1-5}$alkyl, $CH_2OC(O)NR^dR^e$, $CH_2NR^dC(O)R^e$, $CH_2NR^dSO_2R^e$, $CH_2OR^d$, $CH_2$—$Ar^1$ (where $Ar^1$ is optionally substituted with one to two groups selected from $R^a$), $NR^dR^e$, $OR^d$ and oxo;

Y- $R^1$ is hydrogen, $C_{1-5}$alkyl, phenyl optionally substituted with one to three groups selected from $R^a$, $C_{1-5}$alkylene-$R^1$ (where $R^1$ is hydroxy, $C_{1-5}$alkoxy, $C_{1-5}$alkanoyloxy, $NR^dR^e$, $C(O)NR^dR^e$, $NR^dC(O)C_{1-5}$alkyl, or phenyl optionally substituted with one to three groups selected from $R^b$), $C(O)NR^dR^e$, $C(O)OR^5$, $C(O)R^5$;

$Ar^1$—$Ar^2$ is 2'-substituted biphenyl optionally having another substituent, wherein the substituents are selected from $R^b$.

20. A compound of claim 19 wherein A is 2-tetrahydrofuranyl.

21. A compound of claim 19 wherein Y—$R^1$ is hydrogen or methyl.

22. A compound of claim 19 wherein $Ar^1$—$Ar^2$ is 2'-methoxybiphenyl or 2',6'-dimethoxybiphenyl.

* * * * *